US010611824B2

(12) United States Patent
Bregeon

(10) Patent No.: US 10,611,824 B2
(45) Date of Patent: Apr. 7, 2020

(54) SOLID PHASE TGASE-MEDIATED CONJUGATION OF ANTIBODIES

(71) Applicant: Innate Pharma, Marseilles (FR)

(72) Inventor: Delphine Bregeon, Marseilles (FR)

(73) Assignee: Innate Pharma, Marseilles (FR)

( * ) Notice: Subject to any disclaimer, the term of this patent is extended or adjusted under 35 U.S.C. 154(b) by 202 days.

(21) Appl. No.: 14/775,647

(22) PCT Filed: Mar. 14, 2014

(86) PCT No.: PCT/EP2014/055140
§ 371 (c)(1),
(2) Date: Sep. 11, 2015

(87) PCT Pub. No.: WO2014/140300
PCT Pub. Date: Sep. 18, 2014

(65) Prior Publication Data
US 2016/0022833 A1    Jan. 28, 2016

Related U.S. Application Data

(60) Provisional application No. 61/786,856, filed on Mar. 15, 2013.

(51) Int. Cl.
| | |
|---|---|
| *A61K 31/5517* | (2006.01) |
| *C07K 16/00* | (2006.01) |
| *C07K 16/30* | (2006.01) |
| *C07C 217/08* | (2006.01) |
| *C07C 223/02* | (2006.01) |
| *C07C 229/26* | (2006.01) |
| *C07C 233/62* | (2006.01) |
| *C07C 247/04* | (2006.01) |
| *C07C 323/12* | (2006.01) |
| *C07D 225/08* | (2006.01) |
| *C07D 257/08* | (2006.01) |
| *C07D 277/06* | (2006.01) |
| *C07F 9/50* | (2006.01) |
| *C12N 9/10* | (2006.01) |
| *C12P 21/00* | (2006.01) |
| *G01N 33/68* | (2006.01) |
| *A61K 47/68* | (2017.01) |

(52) U.S. Cl.
CPC .............. *C07K 16/00* (2013.01); *A61K 47/68* (2017.08); *A61K 47/6803* (2017.08); *C07K 2317/41* (2013.01)

(58) Field of Classification Search
None
See application file for complete search history.

(56) References Cited

U.S. PATENT DOCUMENTS

| | | | |
|---|---|---|---|
| 4,741,900 A | 5/1988 | Alvarez et al. | |
| 4,816,567 A | 3/1989 | Cabilly et al. | |
| 5,156,956 A | 10/1992 | Motoki et al. | |
| 5,225,539 A | 7/1993 | Winter | |
| 5,229,275 A | 7/1993 | Goroff | |
| 5,252,469 A | 10/1993 | Andou et al. | |
| 5,530,101 A | 6/1996 | Queen et al. | |
| 5,565,332 A | 10/1996 | Hoogenboom et al. | |
| 5,567,610 A | 10/1996 | Borrebaeck et al. | |
| 5,573,905 A | 11/1996 | Lerner et al. | |
| 5,585,089 A | 12/1996 | Queen et al. | |
| 5,693,761 A | 12/1997 | Queen et al. | |
| 5,693,762 A | 12/1997 | Queen et al. | |
| 5,712,120 A | 1/1998 | Rodriguez et al. | |
| 5,714,350 A | 2/1998 | Co et al. | |
| 5,731,183 A | 3/1998 | Kobayashi et al. | |
| 5,736,356 A | 4/1998 | Sano et al. | |
| 5,766,886 A | 6/1998 | Studnicka et al. | |
| 5,770,196 A | 6/1998 | Studnicka | |
| 5,777,085 A | 7/1998 | Co et al. | |
| 5,821,123 A | 10/1998 | Studnicka | |
| 5,821,337 A | 10/1998 | Carter et al. | |
| 5,869,619 A | 2/1999 | Studnicka | |
| 5,877,293 A | 3/1999 | Adair et al. | |
| 5,886,152 A | 3/1999 | Nakatani et al. | |
| 5,895,205 A | 4/1999 | Werner et al. | |
| 5,929,212 A | 7/1999 | Jolliffe et al. | |
| 6,054,297 A | 4/2000 | Carter et al. | |
| 6,162,963 A | 12/2000 | Kucherlapati et al. | |
| 6,180,370 B1 | 1/2001 | Queen et al. | |
| 6,204,388 B1 | 3/2001 | Danishefsky et al. | |
| 6,380,394 B1 | 4/2002 | Nicolaou et al. | |
| 6,387,927 B1 | 5/2002 | Altmann et al. | |

(Continued)

FOREIGN PATENT DOCUMENTS

| | | |
|---|---|---|
| DE | 19907588 A1 | 8/2000 |
| EP | 0555649 A2 | 8/1993 |

(Continued)

OTHER PUBLICATIONS

Deisenhofer et al. (Biochemistry, 1981, 20:2361-2370).*
Wright et al. in 1977 (Biochemical Journal, 1977, 167:661-668).*
Lund et al. (Journal of Immunology, 1996, 157:4963-4969).*
Choie et al., Material, 2016, 9:p. 994, labeled as pp. 1-17.*
Starling et al., "In vivo antitumor activity of a panel of four monoclonal antibody-vinca alkaloid immunoconjugates which bind to three distinct epitopes of carcinoembryonic antigen", Bioconjug Chem. (1992) 3(4):315-322.
U.S. Notice of Allowance dated Mar. 28, 2017 in U.S. Appl. No. 13/725,382, filed Dec. 21, 2012.
U.S. Notice of Allowability/Examiner's Amendment dated Apr. 28, 2017 in U.S. Appl. No. 13/725,382, filed Dec. 21, 2012.
U.S. Office Action dated Jan. 31, 2017 in U.S. Appl. No. 14/367,840, filed Jun. 20, 2014.

(Continued)

*Primary Examiner* — Julie Wu
(74) *Attorney, Agent, or Firm* — Knobbe, Martens, Olson & Bear, LLP

(57) ABSTRACT

Some embodiments described herein relate to solid-support based processes for the functionalization of immunoglobulins through the use of transglutaminase. Also provided are solid support compositions with bound antibody. The methods can be used, for example, in manufacturing processes or in drug screening.

6 Claims, 19 Drawing Sheets

(56) References Cited

U.S. PATENT DOCUMENTS

| | | |
|---|---|---|
| 6,407,213 B1 | 6/2002 | Carter et al. |
| 6,548,640 B1 | 4/2003 | Winter |
| 6,632,927 B2 | 10/2003 | Adair et al. |
| 6,639,055 B1 | 10/2003 | Carter et al. |
| 6,750,325 B1 | 6/2004 | Jolliffe et al. |
| 6,797,492 B2 | 9/2004 | Daugherty et al. |
| 6,881,557 B2 | 4/2005 | Foote |
| 7,087,409 B2 | 8/2006 | Barbas, III et al. |
| 7,090,843 B1 | 8/2006 | Francisco et al. |
| 7,117,096 B2 | 10/2006 | Luo et al. |
| 7,135,174 B2 | 11/2006 | Corvalan et al. |
| 7,338,933 B2 | 3/2008 | DeFrees et al. |
| 7,378,091 B2 | 5/2008 | Gudas et al. |
| 7,393,648 B2 | 7/2008 | Rother et al. |
| 7,498,298 B2 | 3/2009 | Doronina et al. |
| 7,657,380 B2 | 2/2010 | Lazar et al. |
| 7,659,241 B2 | 2/2010 | Senter et al. |
| 7,763,736 B2 | 7/2010 | Sharpless et al. |
| 7,807,619 B2 | 10/2010 | Bertozzi et al. |
| 7,981,843 B2 | 7/2011 | Flynn et al. |
| 7,989,598 B2 | 8/2011 | Steeves et al. |
| 8,133,515 B2 | 3/2012 | Boons et al. |
| 9,340,615 B2 | 5/2016 | Maeda et al. |
| 9,427,478 B2 | 8/2016 | Bregeon et al. |
| 9,676,871 B2 | 6/2017 | Strop et al. |
| 9,717,803 B2 | 8/2017 | Bregeon et al. |
| 9,764,038 B2 | 9/2017 | Dennler et al. |
| 10,036,010 B2 | 7/2018 | Fischer et al. |
| 10,071,169 B2 | 9/2018 | Bregeon et al. |
| 10,434,180 B2 | 10/2019 | Bregeon et al. |
| 2002/0034765 A1 | 3/2002 | Daugherty et al. |
| 2002/0052028 A1 | 5/2002 | Santi et al. |
| 2002/0058286 A1 | 5/2002 | Danishefsky et al. |
| 2002/0062030 A1 | 5/2002 | White et al. |
| 2002/0102208 A1 | 8/2002 | Chinn et al. |
| 2002/0161201 A1 | 10/2002 | Filpula et al. |
| 2003/0153043 A1 | 8/2003 | Carr et al. |
| 2004/0253645 A1 | 12/2004 | Daugherty et al. |
| 2005/0026263 A1 | 2/2005 | Meares et al. |
| 2005/0238646 A1 | 10/2005 | Ledbetter et al. |
| 2005/0238649 A1 | 10/2005 | Doronina et al. |
| 2005/0256030 A1 | 11/2005 | Feng |
| 2006/0073137 A1 | 4/2006 | Adair et al. |
| 2006/0116422 A1 | 6/2006 | de Groot et al. |
| 2007/0122408 A1 | 5/2007 | Barbas, III et al. |
| 2008/0038260 A1 | 2/2008 | Ponath et al. |
| 2009/0028856 A1 | 1/2009 | Chen et al. |
| 2010/0004431 A1 | 1/2010 | Bernett et al. |
| 2011/0184147 A1 | 7/2011 | Kamiya et al. |
| 2011/0256157 A1 | 10/2011 | Howard et al. |
| 2011/0305631 A1 | 12/2011 | Govindan et al. |
| 2012/0322686 A1* | 12/2012 | Lyon ............... A61K 47/48384 506/9 |
| 2013/0122020 A1 | 5/2013 | Liu et al. |
| 2013/0137763 A1 | 5/2013 | van Delft et al. |
| 2013/0189287 A1 | 7/2013 | Bregeon et al. |
| 2013/0230543 A1* | 9/2013 | Pons ............... A61K 47/48369 424/178.1 |
| 2014/0088089 A1 | 3/2014 | Chari |
| 2014/0356385 A1 | 12/2014 | Dennler et al. |
| 2015/0284713 A1 | 10/2015 | Fischer et al. |
| 2015/0346195 A1 | 12/2015 | Belmant et al. |
| 2016/0114056 A1 | 4/2016 | Bregeon et al. |
| 2016/0331842 A1 | 11/2016 | Bregeon et al. |
| 2017/0313787 A1 | 11/2017 | Strop et al. |
| 2018/0071402 A1 | 3/2018 | Bregeon et al. |
| 2018/0193476 A1 | 7/2018 | Dennler et al. |
| 2019/0169601 A1 | 6/2019 | Fischer et al. |

FOREIGN PATENT DOCUMENTS

| | | | |
|---|---|---|---|
| EP | | 1859811 A1 | 11/2007 |
| JP | | 2003199569 A | 7/2003 |
| WO | WO 1992/02190 | | 1/1992 |
| WO | WO 1992/11018 | | 7/1992 |
| WO | WO 1992/22583 | | 12/1992 |
| WO | WO 1993/10102 | | 5/1993 |
| WO | WO 1996/06931 | | 3/1996 |
| WO | WO 1996/22366 | | 7/1996 |
| WO | WO 1998/25929 A1 | | 6/1998 |
| WO | WO 1999/02514 A2 | | 1/1999 |
| WO | WO 1999/07692 A2 | | 2/1999 |
| WO | WO 1999/58534 A2 | | 11/1999 |
| WO | WO 1999/67252 A2 | | 12/1999 |
| WO | WO 1999/67253 A2 | | 12/1999 |
| WO | WO 2000/000485 A1 | | 1/2000 |
| WO | WO 2000/037473 A1 | | 6/2000 |
| WO | WO 2000/049019 A2 | | 8/2000 |
| WO | WO 2000/049020 A2 | | 8/2000 |
| WO | WO 2000/049021 A2 | | 8/2000 |
| WO | WO 2000/057874 A1 | | 10/2000 |
| WO | WO 2000/066589 A1 | | 11/2000 |
| WO | WO 2000/071521 A1 | | 11/2000 |
| WO | WO 2001/027308 A2 | | 4/2001 |
| WO | WO 2001/064650 A2 | | 9/2001 |
| WO | WO 2001/070716 A1 | | 9/2001 |
| WO | WO 2001/073103 A2 | | 10/2001 |
| WO | WO 2001/081342 A2 | | 11/2001 |
| WO | WO 2001/092255 A2 | | 12/2001 |
| WO | WO 2002/008440 A2 | | 1/2002 |
| WO | WO 2002/014323 A2 | | 2/2002 |
| WO | WO 2002/030356 A2 | | 4/2002 |
| WO | WO 2002/032844 A2 | | 4/2002 |
| WO | WO 2002/080846 A2 | | 10/2002 |
| WO | WO 2002/083180 A1 | | 10/2002 |
| WO | WO 2003/074053 A1 | | 9/2003 |
| WO | WO 2004/014919 A1 | | 2/2004 |
| WO | WO 2004/043493 A1 | | 5/2004 |
| WO | WO 2004/043880 A2 | | 5/2004 |
| WO | WO 2005/040219 A1 | | 5/2005 |
| WO | WO 2005/070468 A2 | | 8/2005 |
| WO | WO 2005/085251 A1 | | 9/2005 |
| WO | WO 2007/008603 A1 | | 1/2007 |
| WO | WO 2007/008848 A2 | | 1/2007 |
| WO | WO 2007/020290 A1 | | 2/2007 |
| WO | WO 2008/017122 A1 | | 2/2008 |
| WO | WO 2008/102008 A1 | | 8/2008 |
| WO | WO 2009/067663 A1 | | 5/2009 |
| WO | WO 2009/105969 A1 | | 9/2009 |
| WO | WO 2010/115630 A1 | | 10/2010 |
| WO | WO 2010/136598 A1 | | 12/2010 |
| WO | WO 2011/023883 A1 | | 3/2011 |
| WO | WO 2011/136645 A1 | | 3/2011 |
| WO | WO 2011/085523 A1 | | 7/2011 |
| WO | WO 2011/120053 A1 | | 9/2011 |
| WO | WO 2011/130616 A1 | | 10/2011 |
| WO | WO 2012/041504 A1 | | 4/2012 |
| WO | WO 2012/059882 A2 | | 5/2012 |
| WO | WO 2012/112687 A1 | | 8/2012 |
| WO | WO 2013/092983 A2 | | 6/2013 |
| WO | WO 2013/092998 A1 | | 6/2013 |
| WO | WO 2013/177481 A1 | | 11/2013 |
| WO | WO 2014/009426 A1 | | 1/2014 |
| WO | WO 2014/072482 A1 | | 5/2014 |
| WO | WO 2014/202773 A1 | | 12/2014 |

OTHER PUBLICATIONS

U.S. Response to Office Action dated Apr. 28, 2017 in U.S. Appl. No. 14/367,840, filed Jun. 20, 2014.
U.S. Notice of Allowance dated May 16, 2017 in U.S. Appl. No. 14/367,840, filed Jun. 20, 2014.
Preliminary Amendment dated Jan. 9, 2017 in U.S. Appl. No. 15/214,331, filed Jul. 19, 2016.
U.S. Office Action dated Mar. 31, 2017 in U.S. Appl. No. 14/414,432, filed Jan. 12, 2015.
U.S. Office Action dated Feb. 28, 2017 in U.S. Appl. No. 14/441,157, filed May 6, 2015.
U.S. Response to Office Action dated Apr. 26, 2017 in U.S. Appl. No. 14/441,157, filed May 6, 2015.
U.S. Office Action dated Mar. 31, 2017 in U.S. Appl. No. 14/898,693, filed Dec. 15, 2015.

(56) References Cited

OTHER PUBLICATIONS

U.S. Notice of Allowance dated Feb. 8, 2017 in U.S. Appl. No. 13/883,535, filed May 3, 2013.
U.S. Rule 312 Amendment dated Apr. 3, 2017 in U.S. Appl. No. 13/883,535, filed May 3, 2013.
Sung et al. 2010. Functional glass surface displaying a glutamyl donor substrate for transglutaminase-mediated protein immobilization. *Biotechnology Journal*, 5:456-462.
International Search Report dated Jun. 25, 2014 for International Application No. PCT/EP2014/055140 filed Mar. 14, 2014.
Agard et al., "A Strain-Promoted [3+2] Azide-Alkyne Cyaloaddition for Covalent Modification of Biomolecules in Living Systems", J Am Chem Soc Comm. (2004) 126:15046-15047.
U.S. Response to Office Action dated May 23, 2016 in U.S. Appl. No. 13/725,382, filed Dec. 21, 2012.
U.S. Office Action dated Aug. 8, 2016 in U.S. Appl. No. 13/725,382, filed Dec. 21, 2012.
US. Response to Office Action dated Nov. 9, 2016 in U.S. Appl. No. 13/725,382, filed Dec. 21, 2012.
U.S. Response to Office Action dated Mar. 25, 2016 in U.S. Appl. No. 14/367,840, filed Jun. 20, 2014.
U.S. Office Action dated Jun. 17, 2016 in U.S. Appl. No. 14/367,840, filed Jun. 20, 2014.
U.S. Response to Office Action dated Nov. 14, 2016 in U.S. Appl. No. 14/367,840, filed Jun. 20, 2014.
U.S. Notice of Allowance dated Jun. 6, 2016 in U.S. Appl. No. 14/582,040, filed Dec. 23, 2014.
U.S. Office Action dated Aug. 17, 2016 in U.S. Appl. No. 14/414,432, filed Jan. 12, 2015.
U.S. Response to Office Action dated Nov. 17, 2016 in U.S. Appl. No. 14/414,432, filed Jan. 12, 2015.
U.S. Response dated May 2, 2016 in U.S. Appl. No. 13/883,535, filed May 3, 2013.
U.S. Office Action dated Jul. 5, 2016 in U.S. Appl. No. 13/883,535, filed May 3, 2013.
U.S. Response dated Sep. 1, 2016 in U.S. Appl. No. 13/883,535, filed May 3, 2013.
Chari, Ravi V.J., "Targeted Cancer Therapy: Conferring Specificity to Cytotoxic Drugs", Acc of Chem Res. (Jan. 2008) 41(1):98-107.
Lhospice et al., "Cite-specific conjugation of monomethyl auristatin E to Anti-CD30 antibodies improves their pharmacokinetics and therapeutic index in rodent models", Mol Pharmaceutics (2015) 12:1863-1871.
International Search Report and Written Opinion of the International Searching Authority dated Aug. 20, 2014 for International Application No. PCT/EP2014/063061 filed Jun. 20, 2014.
U.S. Response to Office Action dated Dec. 11, 2015 in U.S. Appl. No. 13/725,382, filed Dec. 21, 2012.
U.S. Office Action dated Feb. 25, 2016 in U.S. Appl. No. 13/725,382, filed Dec. 21, 2012.
U.S. Office Action dated Jan. 29, 2016 in U.S. Appl. No. 14/367,840, filed Jun. 20, 2014.
U.S. Office Action dated Oct. 8, 2015 in U.S. Appl. No. 14/582,040, filed Dec. 23, 2014.
Response to Office Action filed Dec. 8, 2015 in U.S. Appl. No. 14/582,040, filed Dec. 23, 2014.
U.S. Office Action dated Feb. 11, 2016 in U.S. Appl. No. 14/582,040, filed Dec. 23, 2014.
Response to Office Action dated Feb. 29, 2016 in U.S. Appl. No. 14/582,040, filed Dec. 23, 2014.
U.S. Office Action dated Sep. 16, 2015 in U.S. Appl. No. 13/883,535, filed May 3, 2013.
U.S. Response dated Nov. 16, 2015 in U.S. Appl. No. 13/883,535, filed May 3, 2013.
U.S. Office Action dated Dec. 30, 2015 in U.S. Appl. No. 13/883,535, filed May 3, 2013.
Altschul et al., "Gapped BLAST and PSI-BLAST: A new generation of protein database search programs", Nucl Acids Res. (1997) 25(17): 3389-3402.

Altschul et al., "Basic Local Alignment Search Tool", J Mol Biol. (1990) 215:403-410.
Amersham Biosciences, Antibody Purification Handbook, (2002) Publication No. 18-1037-46, Edition AC, 112 pages.
Amsberry et al., "The Lactonization of 2'-Hydroxyhydrocinnamic Acid Amides: A Potential Prodrug for Amines", J. Org Chem ( Apr. 1990) 55:5867-5877.
Ando et al., "Purification and Characteristics of a Novel Transglutaminase Derived from Microorganisms", Agric Biol Chem. (1989) 53(10):2613-2617.
Ausubel et al. (Eds.) Current Protocols in Molecular Biology (1993) John Wiley & Sons, Inc., Table of Contents, 15 pages.
Baeuerle et al., "Bispecific T-cell engaging antibodies for cancer therapy", Cancer Res. (2009) 69(12):4941-4944.
Bernhard et al., "Cysteine analogs of recombinant barley ribosome inactivating protein form antibody conjugates with enhanced stability and potency in vitro", Bioconjugate Chem., (1994) 5(2):126-132.
Brabez et al., "Design, synthesis and biological studies of efficient multivalent melanotropin ligands: tools towards melanoma diagnosis and treatment", J Med Chem. (2011) 54(20):7375-7384.
Carillo et al., "The Multiple Sequence Alignment Problem in Biology", Siam J. Appl Math. (1988) 48(5):1073-1082.
Carter et al., "Improved oligonucleotide site-directed mutagenesis using M13 vectors", Nucl Acids Res. (May 1985) 13(12):4431-4443.
Carter et al., "Humanization of an anti-p185HER2 antibody for human cancer therapy", Proc Natl Acad Sci. USA (1992) 89:4285-4289.
Chapman, Andrew P., "PEGylated antibodies and antibody fragments for improved therapy: a review", Advan Drug Del Rev. (Jan. 2002) 54:531-545.
Chothia et al., "Canonical Structures for the Hypervariable Regions of Immunoglobulins", J Mol Biol. (1987) 196:901-917.
Connolly et al., "In Vivo Inhibition of Fas Ligand-Mediated Killing by TR6, a Fas Ligand Decoy Receptor", J Pharmacol Exp Ther. (Jan. 2001) 298(1):25-33.
De Pascalis et al., "Grafting of "Abbreviated" Complementarity-Determining Regions Containing Specificity-Determining Residues Essential for Ligand Contact to Engineer a Less Immunogenic Humanized Monoclonal Antibody", J Immunol. (2002) 169(6):3076-3084.
Dennler et al., Enzymatic antibody modification by bacterial transglutaminase. Bioconjugate Chemistry, (2013) 1045:205-215.
Dennler et al., Transglutaminase-based chemo-enzymatic conjugation approach yields homogeneous antibody-drug conjugates. Bioconjugate Chemistry, (2014) 25(3):569-578.
Devereux et al., "A comprehensive set of sequence analysis programs for the VAX", Nucl Acids Res. (1984) 12(1):387-395.
Doronina et al., "Development of potent monoclonal antibody Auristatin conjugates for cancer therapy", Nat Biotech. (2003) 21(7):778-784 & Erratum Nat Biotech. (2003) 21(8):941.
Doronina et al., "Enhanced activity of monomethylauristatin F through Monoclonal Antibody Delivery", Bioconjugate Chem. (2006) 17(1):114-124.
Dosio et al., "Immunotoxins and Anticancer Drug Conjugate Assemblies: The Role of the Linkage between Components", Toxins (2011) 3:848-883.
Edelman et al., "The Covalent Structure of an Entire γG Immunoglobulin Molecule", Proc Natl Acad. USA, (1969) 63:78-85.
Folk et al., "Polyamines as Physiological Substrates for Transglutaminases", J. Biol. Chem. (Apr. 1980) 255(8):3695-3700.
GENBANK Reference Sequence NM_024003.2; "*Homo sapiens* L1 cell adhesion molecule (L1CAM), transcript variant 2, mRNA", May 4, 2013; 8 pages.
GENBANK Reference Sequence NM_024003.3; "*Homo sapiens* L1 cell adhesion molecule (L1CAM), transcript variant 2, mRNA", May 26, 2013; 10 pages.
GENBANK Reference Sequence NM_0764493.1; "Neural cell adhesion molecule L1 isoform 2 precursor [*Homo sapiens*]", May 26, 2014; 6 pages.

(56) References Cited

OTHER PUBLICATIONS

Golay et al., "Mechanism of action of therapeutic monoclonal antibodies: Promises and pitfalls of in vitro and in vivo assays", Arch Biochem Biophys (2012) 526:146-153.
Gorman et al., "Transglutaminase Amine Substrates for Photochemical Labeling and Cleavable Cross-linking of Proteins", J Biol Chem. (1980) 255(3):1175-1180.
Green et al., "Antigen-specific human monoclonal antibodies from mice engineered with human Ig heavy and light chain YACs", Nature Gen. (1994) 7:13-21.
Gregson et al., "Linker Length Modules DNA Cross-Linking Reactivity and Cytotoxic Potency of C8/C8' Ether-linked C2-exo-Unsaturated Pyrrolo[2,1-c][1,4]benzodiazepine (PBD) Dimers", J Med Chem (2004) 47:1161-1174.
Gribskov et al., (Eds.) Sequence Analysis Primer; Stockton Press (1991); Table of Contents, 7 pages.
Griffin et al., (Eds.) Methods in Molecular Biology—24: Computer Analysis of Sequence Data; Part I & II; Humana Press, New Jersey (1994) Tables of Contents, 8 pages.
Griffiths et al., "Human anti-self antibodies with high specificity from phage display libraries", EMBO J. (1993) 12(2):725-734.
Griffiths et al., "Isolation of high affinity human antibodies directly from large synthetic repertoires", EMBO J. (1994) 13(14):3245-3260.
Grünberg et al. 2013. DOTA-functionalized polylysine: A high number of DOTA chelates positively influences the biodistribution of enzymatic conjugated anti-tumor antibody chCE7agl. PLOS One, 8(4):e60350.
Hamblett et al., "Effects of Drug Loading on the Antitumor Activity of a Monoclonal Antibody Drug Conjugate", Clin Cancer Res. (Oct. 2004) 10:7063-7070.
Harlow et al., (Eds.), Antibodies—A Laboratory Manual; Table of Contents, Cold Spring Harbor Laboratory Press, Cold Spring Harbor, NY (1988) TOC; 9 pages.
Hay et al., "A 2-nitroimidazole carbamate prodrug of 5-amino-1-(Chloromethyl)-3-[(5,6,7-Trimethoxyindol-2-YL)Carbonyl]-1,2-dihydro-3H-Benz[e]indole (amino-SECO-CBI-TMI) for use with ADEPT and GDEPT", Bioorg Med Chem Lttrs. (Jun. 1999) 9:2237-2242.
Hay et al., "Clinical development success rates for investigational drugs", Nat Biotech. (Jan. 2014) 32(1):40-51.
Higuchi, Russell "Recombinant PCR" Chapter 22 in Part II of PCR Protocols, A Guide to Methods and Applications [Innis et al. (Eds.)], Academic Press, (1990) pp. 177-183.
Ho et al. Site-directed Mutagenesis by Overlap Extension Using the Polymerase Chain Reaction. Gene (1989) 77(1):51-59.
Holliger et al., "Engineered antibody fragments and the rise of single domains", Nature Biotech. (2005) 23(9):1126-1136.
Hu et al., "Rational design of transglutaminase substrate peptides for rapid enzymatic formation of hydrogels", J Am Chem Soc. (Nov. 2003) 125(47):14298-14299.
Ill et al., "Design and construction of a hybrid immunoglobulin domain with properties of both heavy and light chain variable regions", Prot Engineer. (1997) 10(8):949-957.
Ito et al., "A General Method for Introducing a Series of Mutations into Cloned DNA Using the Polymerase Chain Reaction", Gene (Nov. 1991) 102(1):67-70.
Jackman et al., "Development of a two-part strategy to identify a therapeutic human bispecific antibody that inhibits IgE receptor signaling", J Biol Chem. (2010) 285(27):20850-20859.
Jakobovits et al., "Germ-line transmission and expression of a human-derived yeast artificial chromosome", Nature (1993) 362:255-258.
Jeffrey et al., "Development and Properties of beta-Glucuronide Linkers for Monoclonal Antibody-Drug Conjugates", Bioconj Chem. (2006) 17:831-840.
Jeger. Site-Specific Conjugation of Tumour-Targeting Antibodies Using Transglutaminase. Dissertation. ETH Zurich: University of Basel (2009) 1-135.
Jeger et al., "Site-Specific and Stoichiometric Modification of Antibodies by Bacterial Transglutaminase", Angew Chem Int Ed. (2010) 49(51):9995-9997.
Jeger et al., "Site-specific and stoichiometric modification of antibodies by bacterial transglutaminase", Supporting Information. Angewandte Chemie International Edition, Wiley VCH, (2010) 49(51): 46 pages.
Jones et al., "Replacing the complementarity-determining regions in a human antibody with those from a mouse", Nature (1986) 321:522-525.
Josten et al., "Use of microbial transglutaminase for the enzymatic biotinylation of antibodies", J Immunol Meth. (2000) 240:47-54.
Jubala et al., "CD20 Expression in Normal Canine B Cells and in Canine non-Hodgkin Lymphoma", Vet Pathol. (2005) 42:368-476.
Junutula et al., "Site-specific conjugation of a cytotoxic drug to an antibody improves the therapeutic index", Nature Biotech (2008) 26(8):925-932.
Kabat et al., (Eds.) Sequences of Proteins of Immunological Interest, 5th Edition; (1991) Table of Contents; 11 pages.
Kamal et al., "Synthesis of 1,2,3-triazole-linked pyrrolobenzodiazepine conjugates employing 'click' chemistry: DNA-binding affinity and anticancer activity", Bioorg Med Chem Lett. (Feb. 2008) 18(4):1468-1473.
Kämpfer et al., "A numerical classification of the genera *Streptomyces* and *Streptoverticillium* using miniaturized physiological tests", J Gen Microbiol. (Feb. 1991) 137:1831-1891.
Kajiwara et al., "Expression of L1 Cell Adhesion Molecule and Morphologic Features at the Invasive Front of Colorectal Cancer", Anat Pathol. (2011) 136(1):138-144.
Kamiya et al., "S-Peptide as a Potent Peptidyl Linker for Protein Cross-Linking by Microbial Transglutaminase from *Streptomyces mobaraensis*", Bioconj Chem. (2003) 14:351-357.
Kamiya et al., "Site-specific cross-linking of functional proteins by transglutamination", Enzy Micro Tech. (2003) 33:492-496.
Kingsbury et al., "A Novel Peptide Delivery System Involving Peptidase Activated Prodrugs as Antimicrobial Agents. Synthesis and Biological Activity of Peptidyl Derivatives of 5-Fluorouracil", J Med Chem. (Apr. 1984) 27:1447-1451.
Knappik et al., "Fully Synthetic Human Combinatorial Antibody Libraries (HuCAL) Based on Modular Consensus Frameworks and CDRs Randomized with Trinucleotides", J Mol Biol. (2000) 296:57-86.
Knogler et al., "Copper-67 Radioimmunotherapy and Growth Inhibition by Anti-L1-Cell Adhesion Molecule Monoclonal Antibodies in a Therapy Model of Ovarian Cancer Metastasis", Clin Cancer Res (2007) 13(2):603-611.
Kuil et al., "ITAM-derived phosphopeptide-containing dendrimers as multivalent ligands for Syk tandem SH2 domain", Org Biomol Chem. (2009) 7:4088-4094.
Kunkel, Thomas A., "Rapid and efficient site-specific mutagenesis without phenotypic selection", Proc Natl Acad Sci USA (Jan. 1985) 82:488-492.
Lesk, Arthur M. (Ed.) Computational Molecular Biology, Oxford University Press (1988); Table of Contents; 4 pages.
Lin et al., "Transglutaminase-catalyzed site-specific conjugation of small-molecule probes to proteins in vitro and on the surface of living cells", J Am Chem Soc. (2006) 128(14):4542-4543 (7pages).
Liu et al., "Identification of Active Site Residues in the "GyrA" Half of Yeast DNA Topoisomerase II", J Biol Chem. (Aug. 1998) 273(32):20252-20260.
Lonberg et al., "Antigen-specific human antibodies from mice comprising four distinct genetic modifications", Nature (1994) 368:856-859.
Lonberg, Nils, "Human antibodies from transgenic animals", Nature Biotech. (2005) 23(9):1117-1125.
Lorand et al., "Specificity of Guinea Pig Liver Transglutaminase for Amine Substrates", Biochem. (1979) 18(9):1756-1765.
Lorand et al., "Transglutaminases: Cross-linking enzymes with pleiotropic functions", Nature (Feb. 2003) 4:140-156.
Lyon et al., "Conjugation of Anticancer Drugs through Endogenous Monoclonal Antibody Cysteine Residues", Meth Enzymol. (2012) 502:123-138.

(56) References Cited

OTHER PUBLICATIONS

Maeda et al., "Susceptibility of human T-cell leukemia virus type I-infected cells to humanized anti-CD30 monoclonal antibodies in vitro and in vivo", Cancer Sci. (2010) 101(1):224-230.
McCafferty et al., "Phage antibodies: Filamentous phage displaying antibody variable domains", Nature (1990) 348:552-554.
Mindt et al., Modification of Different IgG1 Antibodies Glutamine and Lysine Using Bacterial and Human Tissue Transglutaminase. Bioconjug Chem. (2008) 19(1):271-278.
Morrison et al., "Chimeric human antibody molecules: Mouse antigen-binding domains with human constant region domains", Proc Natl Acad Sci. USA (1984) 81:6851-6855.
Moses et al., "the growing applications of click chemistry", Chem Soc Rev. (Aug. 2007) 36(8):1249-1262.
Murthy et al., "Residue Gln-30 of Human Erythrocyte Anion Transporter is a Prime Site for Reaction with Intrinsic Transglutaminase" J Biolog Chem. (Sep. 1994) 269(36):22907-22911.
Murthy et al., "Selectivity in the Post-Translational, Transglutaminase-dependent Acylation of Lysine Residues", Biochem. (Feb. 2009) 48:2654-2660.
Nilsson et al., A synthetic IgG-binding domain based on stapylococcal protein A. Protein Eng. (1987) 1(2):107-113.
Pearson, William R., "Rapid and Sensitive Sequence Comparison with FASTP and FASTA", Meth Enzymol. (1990) 183(5):63-98.
Pearson, William R., "Flexible sequence similarity searching with the FASTA3 program package", Methods Mol Biol. (2000) 132:185-219.
Plagmann et al., "Transglutaminase-catalyzed covalent multimerization of camelidae anti-human TNF single domain antibodies improves neutralizing activity", J Biotech. (2009) 142:170-178.
Presta, Leonard G., "Antibody engineering", Curr Opin Struct Biol. (1992) 2:593-596.
Presta et al., "Humanization of an Antibody Directed Against IgE", J Immunol. (1993) 151(5):2623-2632.
Riechmann et al., "Reshaping human antibodies for therapy", Nature (1988) 332:323-327.
Rodrigues et al., "Synthesis and β-lactamase-mediated activation of a cephalosporin-taxol prodrug", Chem Biol. (Apr. 1995) 2:223-227.
Roguska et al., "Humanization of murine monoclonal antibodies through variable domain resurfacing", Proc Natl Acad Sci. (1994) 91:969-973.
Sambrook et al., (Eds.) Molecular Cloning—A Laboratory Manual, [2nd Edition]; Cold Spring Harbor Laboratory Press, NY; (1989) Table of Contents, 30 pages.
Sambrook et al., (Eds.) Molecular Cloning—A Laboratory Manual, [3rd Edition]; vol. 1; Cold Spring Harbor Laboratory Press, NY; (2001); Table of Contents, 18 pages.
Sazinsky et al., "Aglycosylated immunoglobulin G1 variants productively engage activating Fc receptors", PNAS (2008) 105(51):20167-20172.
Sims et al., "A Humanized CD18 Antibody can block Function without Cell Destruction", J Immunol. (1993) 151:2296-2308.
Smith, Douglas W. (Ed.), Biocomputing—Informatics and Genome Projects, Academic Press, Inc. (1993) Table of Contents, 7 pages.
Stancovski et al., "Mechanistic aspects of the opposing effects of monoclonal antibodies to the ERBB2 receptor on tumor growth", Proc Natl Acad Sci USA. (Oct. 1991) 88(19):8691-8695.
Strop et al., "Location Matters: Site of Conjugation Modulates Stability and Pharmacokinetics of Antibody Drug Conjugates", Chem Biol. (2013) 20(2):161-167.
Suzuki et al., Glycopinion Mini-Review: N-Glycosylation/Deglycosylation as a Mechanism for the Post-Translational Modification/Remodification of Proteins. Glycoconjug J. (1995) 12:183-193.
Takazawa et al., Enzymatic Labeling of a Single Chain Variable Fragment of an Antibody With Alkaline Phosphates by Microbial Transglutaminase. Biotech Engin. (2004) 86(4):399-404.
Tan et al., "Superhumanized" Antibodies: Reduction of Immunogenic Potential by Complementarity-Determining Region Grafting with Human Germline Sequences: Application to an Anti-CD28. J Immunol. (2002) 169:1119-1125.
Tomlinson et al., The Repertoire of Human Germline VH Sequences Reveals about Fifty Groups of VH Segments with Different Hypervariable Loops. J Mol Biol. (1992) 227:776-798.
Uhlén et al., Complete Sequence of the Staphylococcal Gene Encoding Protein A—A Gene Evolved Through Multiple Duplications. J Biol Chem. (1984) 259(3):1695-1702.
Vallette et al., Construction of Mutant and Chimeric Genes Using the Polymerase Chain Reaction. Nuc Acids Res. (Jan. 1989) 17(2):723-733.
Verhoeyen et al., Reshaping Human Antibodies: Grafting an Antilysozyme Activity. Science (1988) 239:1534-1536.
Von Heinje, Gunnar [Ed.] "Sequence Analysis in Molecular Biology—Treasure Trove or Trivial Pursuit", 1987, Academic Press [TOC Only].
Wakankar et al., Analytical Methods for Physicochemical Characterization of Antibody Drug Conjugates. Landes Biosci. (Mar./Apr. 2011) 3(2):161-172.
Wängler et al., "Antibody-Dendrimer Conjugates: The Number, Not the Size of the Dendrimers, Determines the Immunoreactivity" Bioconjugate Chem. (2008) (19)4:813-820.
Ward et al., Binding Activities of a Repertoire of Single Immunoglobulin Variable Domains Secreted From *Escherichia coli*. Nature (1989) 341:544-546.
Wells et al., Cassette Mutagenesis: An Efficient Method for Generation of Multiple Mutations at Defined Sites. Gene (Jan. 1985) 34(2-3):315-323.
Xu et al., "Characterization of intact antibody-drug conjugates from plasma/serum in vivo by affinity capture capillary liquid chromatography mass spectrometry", Anal Biochem. (2011) 412(1): 56-66.
Yu et al., "Interaction between Bevacizumab and Murine VEGF-A: S Reassessment", Invest Ophtalmol Vis Sci. (Feb. 2008); 49(2):522-527.
Yurkovetskiy et al., Synthesis of a Macromolecular Camptothecin Conjugate with Dual Phase Drug Release. Mol Pharm. (Jun. 2004) 1(5):375-382.
Zoller et al., "Oligonucleotide-directed mutagenesis using M13-derived vectors: an efficient and general procedure for the production of point mutations in any fragment of DNA", Nucl Acids Res. (Aug. 1982) 10(20):6487-6500.
Zoller et al., "Oligonucleotide-directed mutagenesis of DNA fragments cloned into M13 vectors", Methods Enzymol. (1983) 100:468-500.
International Search Report dated Apr. 23, 2013 for International Application No. PCT/EP2012/076631 filed Dec. 21, 2012.
International Search Report dated Feb. 5, 2014 for International Application No. PCT/EP2012/076606 filed Dec. 21, 2012.
International Search Report and Written Opinion dated Sep. 24, 2014 for International Application No. PCT/EP2014/063064 filed Jun. 20, 2014, 16 pages.
International Search Report dated Jan. 31, 2014 for International Application No. PCT/EP2013/064605 filed Jul. 10, 2013.
International Search Report dated Apr. 15, 2014 for International Application No. PCT/EP2013/073428 filed Nov. 8, 2013.
U.S. Appl. No. 61/410,840, filed Nov. 5, 2010.
U.S. Appl. No. 61/553,917, filed Oct. 31, 2011.
U.S. Appl. No. 61/579,908, filed Dec. 23, 2011.
U.S. Appl. No. 61/661,569, filed Jun. 19, 2012.
U.S. Appl. No. 61/671,122, filed Jul. 13, 2012.
U.S. Appl. No. 61/671,128, filed Jul. 13, 2012.
U.S. Appl. No. 61/837,932, filed Jun. 21, 2013.
U.S. Office Action dated Feb. 27, 2015 in U.S. Appl. No. 13/725,382, filed Dec. 21, 2012.
U.S. Response to Office Action filed May 28, 2015 in U.S. Appl. No. 13/725,382, filed Dec. 21, 2012.
U.S. Office Action dated Aug. 13, 2015 in U.S. Appl. No. 13/725,382, filed Dec. 21, 2012.
U.S. Office Action dated Apr. 23, 2015 in U.S. Appl. No. 14/582,040, filed Dec. 23, 2014.
U.S. Response to Office Action filed May 20, 2015 in U.S. Appl. No. 14/582,040, filed Dec. 23, 2014.
U.S. Pre-Interview Communication dated Jul. 2, 2015 in U.S. Appl. No. 14/582,040, filed Dec. 23, 2014.

(56) References Cited

OTHER PUBLICATIONS

U.S. Response to Pre-Interview Communication dated Jul. 31, 2015 in U.S. Appl. No. 14/582,040, filed Dec. 23, 2014.
U.S. Preliminary Amendment dated May 3, 2013 in U.S. Appl. No. 13/883,535, filed May 3, 2013.
U.S. Office Action dated Dec. 19, 2014 in U.S. Appl. No. 13/883,535, filed May 3, 2013.
U.S. Second Preliminary Amendment dated Feb. 17, 2015 in U.S. Appl. No. 13/883,535, filed May 3, 2013.
Alley et al., "Antibody-drug conjugates: targeted drug delivery for cancer", Curr Opin Chem Biol. (2010) 14:529-537.
International ImMunoGeneTics Information Systems, "MCT Scientific Chart" (downloaded from the web Aug. 20, 2017) URL: http://www.imgt.org/IMGTScientificChart/Numbering/Hu_IGHGnber.html; 4 pages.
U.S. Response to Office Action dated Aug. 29, 2017 in U.S. Appl. No. 14/414,432, filed Jan. 12, 2015.
U.S. Office Action dated Nov. 17, 2017 in U.S. Appl. No. 14/414,432, filed Jan. 12, 2015.
U.S. Office Action dated Sep. 19, 2017 in U.S. Appl. No. 14/441,157, filed May 6, 2015.
U.S. Response to Office Action dated Jun. 29, 2017 in U.S. Appl. No. 14/898,693, filed Dec. 15, 2015.
U.S. Office Action dated Oct. 19, 2017 in U.S. Appl. No. 14/898,693, filed Dec. 15, 2015.
U.S. Divisional Application/Preliminary Amendment dated May 11, 2017 in U.S. Appl. No. 15/593,259, filed May 11, 2017.
U.S. Preliminary Amendment dated Jul. 19, 2017 in U.S. Appl. No. 15/654,585, filed Jul. 19, 2017.
U.S. Office Action dated Mar. 8, 2018 in U.S. Appl. No. 15/214,331, filed Jul. 19, 2016.
U.S. Response to Office Action dated Jul. 6, 2018 in U.S. Appl. No. 15/214,331, filed Jul. 19, 2016.
U.S. Response to Office Action dated Apr. 4, 2018 in U.S. Appl. No. 14/414,432, filed Jan. 12, 2015.
U.S. Notice of Allowance dated Jul. 9, 2018 in U.S. Appl. No. 14/414,432, filed Jan. 12, 2015.
U.S. Response dated Feb. 14, 2018 in U.S. Appl. No. 14/441,157, filed May 6, 2015.
U.S. Notice of Allowance dated Mar. 22, 2018 in U.S. Appl. No. 14/441,157, filed May 6, 2015.
U.S. Notice of Allowability [Suppl.] dated Apr. 2, 2018 in U.S. Appl. No. 14/441,157, filed May 6, 2015.
U.S. Response to Office Action filed Jan. 19, 2018 in U.S. Appl. No. 14/898,693, filed Dec. 15, 2015.
U.S. Examiner's Amendment dated May 9, 2018 in U.S. Appl. No. 14/898,693, filed Dec. 15, 2015.
U.S. Notice of Allowance dated May 24, 2018 in U.S. Appl. No. 14/898,693, filed Dec. 15, 2015.
U.S. Response to Pre-Exam Formalities dated Jul. 21, 2017 in U.S. Appl. No. 15/593,259, filed May 11, 2017.
U.S. Office Action dated May 31, 2018 in U.S. Appl. No. 15/593,259, filed May 11, 2017.
U.S. Response to Restriction Requirement dated Jul. 23, 2018 in U.S. Appl. No. 15/593,259, filed May 11, 2017.
Chen et al., "Enhancement and destruction of antibody function by somatic mutation: unequal occurrence is controlled by V gene combinatorial associations", EMBO J. (1995) 14(12):2784-2794.
Edwards et al., "The Remarkable Flexibility of the Human Antibody repertoire; isolation of over one thousand different antibodies to a single protein, BLyS", J Mol Biol. (2003) 334(1):103-118.
Kelly, "An antibody-cytotoxic conjugate, BIIB015, is a new targeted therapy for Cripto positive tumours." Eur J Cancer. (2011) 47(11):1736-1746.
Kussie et al., "A single engineered amino acid substitutions changes antibody fine specificity", J Immunol. (1994) 152(1):146-152.
Lloyd et al., "Modelling the human immune response: performance of a 1011 human antibody repertoire against a broad panel of therapeutically relevant antigens", Protein Eng Des Sel. (2009) 22(3):159-168.
Praderio C., "Selma Blair says she's living with an 'aggressive form' of multiple sclerosis. Here's what to know about the incurable condition.", Business Insider (2019); accessed from businessinsider.sg on Mar. 11, 2019; Excerpt in 1 page.
Rahman et al., "Effect of base sequence on the DNA cross-linking properties of pyrrolobenzodiazepine (PBD) dimers", Nucl Acids Res. (2011) 39(13):5800-5812.
Rudikoff et al., "Single amino acid substitution altering antigen-binding specificity", PNAS U.S.A., (1982) 79:1979-1983.
U.S. Office Action dated Apr. 16, 2019 in U.S. Appl. No. 15/654,585, filed Jul. 19, 2017.
U.S. Office Action dated Nov. 20, 2018 in U.S. Appl. No. 15/702,586, filed Sep. 12, 2017.
U.S. Response to Office Action filed Feb. 19, 2019 in U.S. Appl. No. 15/702,586, filed Sep. 12, 2017.
U.S. Office Action dated Mar. 20, 2019 in U.S. Appl. No. 15/702,586, filed Sep. 12, 2017.
U.S. Office Action dated Sep. 18, 2018 in U.S. Appl. No. 15/214,331, filed Jul. 19, 2016.
U.S. Response to Office Action dated Mar. 18, 2019 in U.S. Appl. No. 15/214,331, filed Jul. 19, 2016.
U.S. Preliminary Amendment dated Feb. 25, 2019 in U.S. Appl. No. 16/035,437, filed Jul. 13, 2018.
U.S. Office Action dated Oct. 1, 2018 in U.S. Appl. No. 15/593,259, filed May 11, 2017.
U.S. Response to Office Action dated Mar. 29, 2019 in U.S. Appl. No. 15/593,259, filed May 11, 2017.
Wu et al., "Humanization of a Murine Monoclonal Antibody by Simultaneous Optimization of Framework and CDR Residues", J Mol Biol. (1999) 294:151-162.
U.S. Response to Office Action dated Jul. 22, 2019 in U.S. Appl. No. 15/702,586, filed Sep. 12, 2017.
U.S. Office Action dated Sep. 30, 2019 in U.S. Appl. No. 15/702,586, filed Sep. 12, 2017.
U.S. Notice of Allowance dated May 31, 2019 in U.S. Appl. No. 15/214,331, filed Jul. 19, 2016.
U.S. Office Action dated May 30, 2019 in U.S. Appl. No. 15/593,259, filed May 11, 2017.
U.S. Response to Office Action dated Sep. 30, 2019 in U.S. Appl. No. 15/593,259, filed May 11, 2017.

* cited by examiner

SOLID PHASE TGASE-MEDIATED CONJUGATION OF ANTIBODIES

CROSS-REFERENCE TO RELATED APPLICATIONS

This application is the U.S. National Phase of Application No. PCT/EP2014/055140 entitled "SOLID PHASE TGASE-MEDIATED CONJUGATION OF ANTIBODIES" filed Mar. 14, 2014, which designated the United States and this application claims the benefit of U.S. Provisional Application No. 61/786,856, filed Mar. 15, 2013, the disclosure of which is incorporated herein by reference in its entirety, including any drawings.

FIELD OF THE INVENTION

The present invention relates to a method for the functionalization of immunoglobulins.

BACKGROUND

Transglutaminases (TGases) have been exploited for some time in the food industry for their ability to cross-link proteins. TGases have been shown to be capable of conjugating glutamine and lysine residues, including antibodies (see, e.g., Josten et al. (2000) J. Immunol. Methods 240, 47-54; Mindt et al (2008) Bioconjug. Chem. 19, 271-278; Jeger et al (2010) Angew. Chem. Int. Ed. 49: 9995-9997); Kamiya et al (2003) Enzyme. Microb. Technol. 33, 492-496 and U.S. patent publication no. 2011/0184147.

Conjugation of molecular markers and other moieties of interest to antibodies are of considerable commercial interest. However, the rules which govern selection by TGases of glutamine residues for modification are still largely unknown. Moreover, production process permitting highly controlled large scale and economically advantageous production of conjugated antibodies have not been reported. There is therefore a need in the art for improved methods to predictably moieties onto polypeptides using TGases.

SUMMARY OF THE INVENTION

The present invention arises, inter alia, from the development of an approach to make use of transglutaminase (TGase)-mediated conjugation to overcome difficulties in conjugation of moieties of interest to immunoglobulins (referred to interchangeably with "antibodies"), and from the provision of TGase-mediated conjugation approaches that permit such conjugation to occur on solid supports. The solid phase processes developed herein permit high drug-antibody ratios (DAR) to be reached, with highly controlled conjugation only at the desired residues, while minimizing the quantities of TGase enzyme and/or drug conjugates/linkers.

It is shown herein that TGase is capable of conjugation with high efficiency onto acceptor glutamines in Fc domains when the antibody is immobilized. Such conjugation onto the Fc domain is possible even when the antibody is bound to the solid support by its Fc domain; neither of the antibody's two Fc domains are blocked to TGase activity, thereby yielding DARs greater than 1 (approaching 2) for antibodies with 2 potential acceptor glutamines, and greater than 2 (approaching 4) for antibodies with 4 potential acceptor glutamines. Among other advantages, this can permit high antibody concentrations to be used in production (e.g. above the 10 mg/ml concentration range where solution phase reactive may become difficult).

It is also shown that an antibody sample conjugated to a reactive linker by TGase can be directly applied to a solid support (i.e. without purification to remove TGase from the reaction mixture) and then reacted with a complementary reactive linker to form a final antibody-drug conjugate. Using complementary reactive moieties of Click-chemistry type on the linkers, high yields are achieved, and moreover even when using low molar equivalents of toxin (e.g. 1-2 equivalents of toxin per acceptor glutamine). This permits for example TGase conjugation reaction mixture to be applied directly to a solid support (e.g. followed by washing to remove TGase any other unnecessary components). This also permits an entirely solid phase process, where antibody is immobilized and then conjugated by TGase and further reacted while on the solid support.

In one aspect of the solid phase processes embodiments, an antibody is bound to a solid support and while on the solid support is conjugated via TGase to a linker comprising a final moiety of interest (e.g. a drug).

In a +second aspect of the solid phase processes, an antibody is bound to a solid support and while on the solid support is conjugated via TGase to a linker comprising a reactive group (e.g. a click chemistry reagent). The resulting antibody conjugated to a reactive linker can then be reacted with a linker comprising a complementary reactive group and a moiety of interest (e.g. a drug), where this reaction can occur on a solid support (e.g. the same solid support) or in solution. See FIG. 17 for an illustration of this second aspect, when carried out entirely on a solid support.

In a third aspect of the solid phase processes, TGase is used to conjugate, in solution, an antibody to a linker comprising a reactive group, and the reaction mixture comprising at least the conjugated antibody, and advantageously also remaining TGase enzyme (i.e. without purification to remove TGase), is applied (introduced) to a solid support such that the antibody (but not TGase) is bound to the solid support, followed by a reaction step in which a linker comprising a complementary reactive group and a moiety of interest (e.g. a drug) is applied to the solid support, resulting in an antibody conjugated via a linker to moiety of interest (e.g. drug). See FIG. 19 for an illustration of this third aspect, when carried out entirely on a solid support.

In one aspect, provided is a method for preparing an antibody or antibody fragment comprising a moiety of interest bound thereto, comprising the steps of:

(a) immobilizing an antibody comprising an acceptor glutamine on a solid support to provide an immobilized antibody, optionally comprising a step of applying an antibody-containing sample to a solid support;

(b) reacting the immobilized antibody of step (a) with a linking reagent comprising a moiety of interest, in the presence of a TGase, under conditions sufficient to obtain an antibody comprising an acceptor glutamine linked (covalently) to a moiety-of-interest via a linker. In one embodiment, the moiety of interest is a reactive moiety (R), optionally a click chemistry reagent, e.g. an azide or an alkyne. In one embodiment, the moiety of interest is a moiety Z described herein, e.g. a drug. In one embodiment, following step (b), the method comprises a step of eluting immobilized antibody conjugates from the solid support.

In one embodiment, the method is used to conduct a TGase reaction at a higher concentration of antibody. It has been observed that TGase reactions at higher concentrations of antibodies can exhibit problems including aggregation, and precipitation, which can be overcome by immobilization on a solid support. Thus, in one aspect, step (a) comprises applying an antibody-containing sample to a solid support so as to obtain, upon elution a concentration of antibody of greater than 10 mg/ml.

In one aspect, provided are method for conjugating a moiety of interest (Z) to an antibody, comprising the steps of:

(a) reacting, in solution and in the presence of a TGase, (i) an antibody, with (ii) a linking reagent comprising a reactive group, under conditions sufficient to obtain an antibody comprising an acceptor glutamine linked (covalently) to a reactive group (R) via a linker;

(b) applying an antibody-containing sample of step (a) to a solid support, thereby immobilizing the antibody comprising an acceptor glutamine linked (covalently) to a reactive group (R) of step (a) on a solid support;

(c) reacting (i) the immobilized antibody obtained in step b), with (ii) a compound comprising a moiety of interest (Z) and a reactive group (R') capable of reacting with reactive group R, under conditions sufficient to obtain an antibody comprising an acceptor glutamine linked to a moiety of interest (Z) via a lysine-based linker. In one embodiment, the step (b) comprises applying an antibody-containing sample of step (a) to a solid support, wherein the sample comprises TGase enzyme and antibody comprising an acceptor glutamine linked (covalently) to a reactive group (R) via a linker. In one embodiment, the step (c) comprises applying a compound comprising a moiety of interest (Z) and a reactive group (R') to the solid support. In one embodiment, following step (c), the method comprises a step of eluting immobilized antibody conjugates from the solid support. In one embodiment, compound comprising a moiety of interest (Z) and a reactive group (R') is provided in an amount which is less than 10, 5, 4, 2 or 1.5 molar equivalents per acceptor glutamine, or less than 20, 10, 8, 4 or 3 molar equivalents per antibody when the antibody has two acceptor glutamines, or less than 20, 10, 8, or 6 molar equivalents per antibody when the antibody has four acceptor glutamines.

In one aspect, provided is a method for conjugating a moiety of interest (Z) to an antibody, comprising the steps of:

(a) immobilizing an antibody comprising an acceptor glutamine on a solid support to provide an immobilized antibody, optionally comprising a step of applying an antibody-containing sample to a solid support;

(b) reacting the immobilized antibody of step (a) with a linking reagent comprising a reactive group, in the presence of a TGase, under conditions sufficient to obtain an antibody comprising an acceptor glutamine linked (covalently) to a reactive group (R) via a linker; and (c) optionally, reacting (i) the antibody obtained in step b) with (ii) a compound comprising a moiety of interest (Z) and a reactive group (R') capable of reacting with reactive group R, under conditions sufficient to obtain an antibody comprising an acceptor glutamine linked to a moiety of interest (Z) via a lysine-based linker.

In one embodiment, the reaction of step (c) is carried out while the antibody remains immobilized on a solid support. In one embodiment, the antibody comprising an acceptor glutamine linked to a moiety-of-interest via a linker remains immobilized on a solid support and the moiety of interest is a reactive group (R), and the method further comprises a step of applying a compound comprising a moiety Z and a reactive group R' that is reactive with reactive group (R) to a solid support, to generate an antibody-moiety-of-interest (Z) conjugate. Optionally, the method may further comprise a step of recovering unreacted compound comprising a moiety Z and a reactive group R' and re-applying said compound to the solid support to provide for higher completion of the reaction between antibody comprising reactive group (R) and compound comprising reactive group (R').

In one embodiment, following step (b), the method comprises a step of eluting immobilized antibody conjugates from the solid support, and step (c) is carried out is solution (antibody is not immobilized on a solid support).

Optionally, any of the methods may or may not further comprise a washing step (e.g. after step (b) and/or step (c)) to remove any unreacted materials.

Optionally, any of the methods may further comprise a step of eluting immobilized antibody conjugates from the solid support to provide antibody conjugate compositions.

Optionally, in any of the methods the linking reagent is a compound of formula Ia:

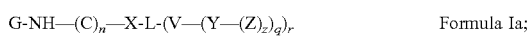

G-NH—(C)$_n$—X-L-(V—(Y—(Z)$_z$)$_q$)$_r$     Formula Ia;

or a pharmaceutically acceptable salt or solvate thereof wherein:

G is an H, amine protecting group, or an antibody attached via an amide bond;

(C)$_n$ is a substituted or unsubstituted alkyl or heteroalkyl chain, optionally where the carbon adjacent to the nitrogen is unsubstituted, optionally wherein any carbon of the chain is substituted alkoxy, hydroxyl, alkylcarbonyloxy, alkyl-S—, thiol, alkyl-C(O)S—, amine, alkylamine, amide, or alkylamide (e.g. with a O, N or S atom of an ether, ester, thioether, thioester, amine, alkylamine, amide, or alkylamide);

n is an integer selected from among the range of 2 to 20, preferably 3 to 6;

X is NH, O, S, or absent;

L is a bond or a carbon comprising framework of 1 to 200 atoms substituted at one or more atoms, optionally wherein the carbon comprising framework is a linear hydrocarbon, a symmetrically or asymmetrically branched hydrocarbon, monosaccharide, disaccharide, linear or branched oligosaccharide (asymmetrically branched or symmetrically branched), an amino acid, a di-, tri-, tetra-, or oligopeptide, other natural linear or branched oligomers (asymmetrically branched or symmetrically branched), or a dimer, trimer, or higher oligomer (linear, asymmetrically branched or symmetrically branched) resulting from any chain-growth or step-growth polymerization process;

r is an integer selected from among 1, 2, 3 or 4;

q is an integer selected from among 1, 2, 3 or 4; and z is an integer selected from among 1, 2, 3 or 4;

V is independently absent, a bond or a continuation of a bond if L is a bond, a non-cleavable moiety or a conditionally-cleavable moiety, optionally following prior conditional transformation, which can be cleaved or transformed by a chemical, photochemical, physical, biological, or enzymatic process (e.g. cleavage of V ultimately leading to release of one or more moieties subsequently or ultimately linked to V, for example a Z moiety). In some embodiments, V is, preferably, a di-, tri-, tetra-, or oligopeptide as described below in the section entitled "The V Moiety";

Y is independently absent, a bond or a continuation of a bond if V is a bond or continuation of a bond, or a spacer system (e.g., a self-eliminating spacer system or a non-self-elimination spacer system) which is comprised of 1 or more spacers; and Z is a moiety that improves the pharmacokinetic properties, a therapeutic moiety or a diagnostic moiety.

Optionally, in any of the methods the linking reagent is a compound of formula Ib:

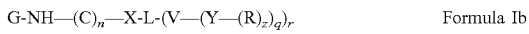
G-NH—(C)$_n$—X-L-(V—(Y—(R)$_z$)$_q$)$_r$                     Formula Ib or a pharmaceutically acceptable salt or solvate thereof wherein:

G is an H, amine protecting group, or an antibody attached via an amide bond;

(C)$_n$ is a substituted or unsubstituted alkyl or heteroalkyl chain, optionally where the carbon adjacent to the nitrogen is unsubstituted, optionally wherein any carbon of the chain is substituted alkoxy, hydroxyl, alkylcarbonyloxy, alkyl-S—, thiol, alkyl-C(O)S—, amine, alkylamine, amide, or alkylamide (e.g. with a O, N or S atom of an ether, ester, thioether, thioester, amine, alkylamine, amide, or alkylamide);

n is an integer selected from among the range of 2 to 20, preferably 3 to 6;

X is NH, O, S, or absent;

L is a bond or a carbon comprising framework of 1 to 200 atoms substituted at one or more atoms, optionally wherein the carbon comprising framework is a linear hydrocarbon, a symmetrically or asymmetrically branched hydrocarbon, monosaccharide, disaccharide, linear or branched oligosaccharide (asymmetrically branched or symmetrically branched), an amino acid, a di-, tri-, tetra-, or oligopeptide, other natural linear or branched oligomers (asymmetrically branched or symmetrically branched), or a dimer, trimer, or higher oligomer (linear, asymmetrically branched or symmetrically branched) resulting from any chain-growth or step-growth polymerization process;

r is an integer selected from among 1, 2, 3 or 4;

q is an integer selected from among 1, 2, 3 or 4; and z is an integer selected from among 1, 2, 3 or 4;

V is independently absent, a bond or a continuation of a bond if L is a bond, a non-cleavable moiety or a conditionally-cleavable moiety, optionally following prior conditional transformation, which can be cleaved or transformed by a chemical, photochemical, physical, biological, or enzymatic process (e.g. cleavage of V ultimately leading to release of one or more moieties subsequently or ultimately linked to V, for example a Z moiety). In some embodiments, V is, preferably, a di-, tri-, tetra-, or oligopeptide as described below in the section entitled "The V Moiety";

Y is independently absent, a bond or a continuation of a bond if V is a bond or continuation of a bond, or a spacer system (e.g., a self-eliminating spacer system or a non-self-elimination spacer system) which is comprised of 1 or more spacers; and R is a reactive moiety.

Optionally, in any of the methods the antibody-moiety-of-interest conjugate obtained is an antibody or antibody fragment comprising a functionalized acceptor glutamine residue having a structure of formula IVa:

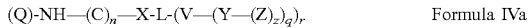
(Q)-NH—(C)$_n$—X-L-(V—(Y—(Z)$_z$)$_q$)$_r$                     Formula IVa or a pharmaceutically acceptable salt thereof;
wherein:

Q is glutamine residue present in an antibody;

(C)$_n$ is a substituted or unsubstituted alkyl or heteroalkyl chain, wherein any carbon of the chain is optionally substituted with an alkoxy, hydroxyl, alkylcarbonyloxy, alkyl-S—, thiol, alkyl-C(O)S—, amine, alkylamine, amide, or alkylamide (e.g. a O, N or S atom of an ether, ester, thioether, thioester, amine, alkylamine, amide, or alkylamide);

n is an integer selected from among the range of 2 to 20;

X is NH, O, S, or absent;

L is a bond or a carbon comprising framework, preferably of 1 to 200 atoms substituted at one or more atoms, optionally wherein the carbon comprising framework is a linear hydrocarbon, a symmetrically or asymmetrically branched hydrocarbon monosaccharide, disaccharide, linear or branched oligosaccharide (asymmetrically branched or symmetrically branched), other natural linear or branched oligomers (asymmetrically branched or symmetrically branched), or a dimer, trimer, or higher oligomer (linear, asymmetrically branched or symmetrically branched) resulting from any chain-growth or step-growth polymerization process;

r is an integer selected among 1, 2, 3 or 4;

q is an integer selected among 1, 2, 3 or 4;

z is an integer selected among 1, 2, 3 or 4; and

V is independently absent, a non-cleavable moiety or a conditionally-cleavable moiety that can optionally be cleaved or transformed by a chemical, photochemical, physical, biological, or enzymatic process (e.g. cleavage of V ultimately leading to release of one or more moieties subsequently or ultimately linked to V, for example a Z moiety). In some embodiments, V is, preferably, a di-, tri-, tetra-, or oligopeptide as described below in the section entitled "The V Moiety";

Y is independently absent or a spacer (e.g., a self-eliminating spacer system or a non-self-elimination spacer system) which is comprised of 1 or more spacers; and Z is a moiety-of-interest, optionally a moiety that improves the pharmacokinetic properties, or a therapeutic moiety or a diagnostic moiety.

Optionally, in any of the methods the antibody-moiety-of-interest conjugate obtained is an antibody or antibody fragment comprising a functionalized acceptor glutamine residue having a structure of Formula II (the result of reacting an antibody having an acceptor glutamine with a linking reagent of formula Ib):

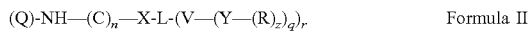
(Q)-NH—(C)$_n$—X-L-(V—(Y—(R)$_z$)$_q$)$_r$                     Formula II or a pharmaceutically acceptable salt or solvate thereof, wherein:

Q is a glutamine residue present in an antibody or antibody fragment;

(C)$_n$ is a substituted or unsubstituted alkyl or heteroalkyl chain, optionally wherein any carbon of the chain is optionally substituted with alkoxy, hydroxyl, alkylcarbonyloxy, alkyl-S—, thiol, alkyl-C(O)S—, amine, alkylamine, amide, or alkylamide;

n is an integer from among the range of 2 to 20;

X is NH, O, S, absent, or a bond;

L is independently absent, a bond or a continuation of a bond, or a carbon comprising framework of 1 to 200 atoms substituted at one or more atoms, optionally wherein the carbon comprising framework comprises a linear framework of 3 to 30 carbon atoms optionally substituted at one or more atoms, optionally wherein the carbon comprising framework is a linear hydrocarbon, a symmetrically or asymmetrically branched hydrocarbon, monosaccharide, disaccharide, linear or branched oligosaccharide (asymmetrically branched or symmetrically branched), other natural linear or branched oligomers (asymmetrically branched or symmetrically branched), or a dimer, trimer, or higher oligomer (linear, asymmetrically branched or symmetrically branched) resulting from any chain-growth or step-growth polymerization process;

r is an integer selected from among 1, 2, 3 or 4;

q is an integer selected from among 1, 2, 3 or 4;

z is an integer selected from among 1, 2, 3 or 4; and

V is independently absent, a bond or a continuation of a bond, a non-cleavable moiety or a conditionally-cleavable moiety;

Y is independently absent, a bond or a continuation of a bond, or a spacer system which is comprised of 1 or more spacers; and R is a reactive moiety.

Optionally, in any of the methods the antibody-moiety-of-interest conjugate obtained is an antibody or antibody fragment comprising a functionalized acceptor glutamine residue having a structure of formula IVb (the result of reacting an antibody having an acceptor glutamine of formula II with a reagent of formula III):

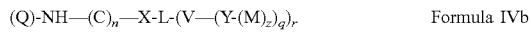
　　　　　　　　　　　　　　　　　　　　　Formula IVb or a pharmaceutically acceptable salt or solvate thereof; wherein:

Q is glutamine residue present in an antibody;

$(C)_n$ is a substituted or unsubstituted alkyl or heteroalkyl chain, wherein any carbon of the chain is optionally substituted with an alkoxy, hydroxyl, alkylcarbonyloxy, alkyl-S—, thiol, alkyl-C(O)S—, amine, alkylamine, amide, or alkylamide;

n is an integer selected from among the range of 2 to 20;

X is NH, O, S, or absent;

L is a bond or a carbon comprising framework, preferably of 1 to 200 atoms substituted at one or more atoms, optionally wherein the carbon comprising framework is a linear hydrocarbon, a symmetrically or asymmetrically branched hydrocarbon monosaccharide, disaccharide, linear or branched oligosaccharide (asymmetrically branched or symmetrically branched), other natural linear or branched oligomers (asymmetrically branched or symmetrically branched), or a dimer, trimer, or higher oligomer (linear, asymmetrically branched or symmetrically branched) resulting from any chain-growth or step-growth polymerization process;

r is an integer selected among 1, 2, 3 or 4;
q is an integer selected among 1, 2, 3 or 4;
z is an integer selected among 1, 2, 3 or 4; and V is independently absent, a non-cleavable moiety or a conditionally-cleavable moiety that can optionally be cleaved or transformed by a chemical, photochemical, physical, biological, or enzymatic process (e.g. cleavage of V ultimately leading to release of one or more moieties subsequently or ultimately linked to V, for example a Z moiety). In some embodiments, V is, preferably, a di-, tri-, tetra-, or oligopeptide as described below in the section entitled "The V Moiety";

Y is independently absent or a spacer (e.g., a self-eliminating spacer system or a non-self-elimination spacer system) which is comprised of 1 or more spacers; and M is independently: R or $(RR')-L'-(V'—(Y'—(Z)_{z'})_{q'})_{r'}$, wherein each of L', V', Y', z', q', and r' are as defined in Formula III (or are defined as L, V, Y, z, q and r, respectively, Z is a moiety-of-interest, optionally a moiety that improves the pharmacokinetic properties, or a therapeutic moiety or a diagnostic moiety, R is a reactive moiety and wherein each (RR') is an addition product between an R and a complementary reactive group R'.

In one embodiment of any of the methods, the step of immobilizing an antibody comprising an acceptor glutamine on a solid support comprises a step of (i) applying (e.g., binding) an antibody-capturing agent to a solid support and (ii) applying an antibody-containing sample to the solid support, wherein the antibody is bound by the antibody-capturing agent. Optionally, the antibody-capturing agent binds the constant region, e.g., the Fc domain, of an antibody. Optionally, the antibody-capturing agent is an affinity capture resin. It will be appreciated that any suitable antibody capture reagent can be used. In one embodiment, the antibody-capturing agent comprises a protein G affinity medium. In one embodiment, the antibody-capturing agent comprises protein A affinity medium.

In one aspect of any of the methods herein, the antibody comprises an acceptor glutamine in a constant region. In one aspect of any of the methods, the antibody comprises an acceptor glutamine in a TGase recognition tag. In one aspect of any of the methods, the antibody comprises an acceptor glutamine in a TGase recognition tag fused to a constant region. In one aspect of any of the methods, the antibody comprises an acceptor glutamine in a CH2 domain. In one aspect of any of the methods, the antibody comprises an acceptor glutamine at residue Q295 (Kabat EU numbering) of a CH2 domain. In one aspect of any of the methods, the antibody comprises an acceptor glutamine at residue 297 (Kabat EU numbering) of a CH2 domain. In one aspect of any of the methods, the antibody is a full-length antibody. In one aspect of any of the methods, the antibody is an antibody fragment or derivative. In one aspect of any of the methods, the fragment or derivative comprises a TGase recognition tag comprising an acceptor glutamine residue.

In one aspect of any of the methods, the step of reacting the immobilized antibody comprises reacting an antibody with a lysine-based linker of Formula Ic, in the presence of a TGase, under conditions sufficient such that antibodies in such first and second antibody samples are conjugated to a lysine-based linker comprising a moiety-of-interest (Z).

In one aspect of any of the methods, the step of reacting the immobilized antibody comprises reacting an antibody with a lysine-based linker of Formula Ia, in the presence of a TGase, under conditions sufficient such that antibodies of Formula II comprising a reactive moiety (R) are obtained, and further reacting the antibodies of Formula II to obtain antibodies of Formula IV comprising a moiety-of-interest (Z).

In one aspect of any of the methods, at least 70%, 80%, 90%, 95%, 98% or 99% of the antibodies in an antibody sample obtained by the method have the same number of functionalized acceptor glutamine residues (Q) per antibody.

In one aspect of any of the methods, at least 70%, 80%, 90%, 95%, 98% or 99% of the antibodies in an antibody sample obtained by the method have no more or no less than (m) functionalized acceptor glutamine residues (Q) per antibody, wherein m is an integer, e.g. m=1, 2, 3 or 4.

In one aspect of any of the methods, the antibody sample obtained by the method comprises a plurality of antibodies of Formula II or IV, wherein at least 70%, 80%, 90%, 95%, 98% or 99% of the antibodies in the composition have the same number of functionalized acceptor glutamine residues (Q) per antibody and at least 70%, 80%, 80%, 90%, 95%, 98% or 99% of the antibodies in the composition have the same q, r and z values.

In one aspect of any of the methods, the antibody sample obtained by the method comprises a plurality of antibodies of Formula II or IV having two functionalized acceptor glutamines per antibody, wherein the composition is characterized by a mean Z (or R): antibody ratio (e.g. mean DAR) of between 1.4 and 2.0, or between 1.7 and 2.0, between 1.8 and 2.0, or between 1.9 and 2.0). In one aspect of any of the methods, the antibody sample obtained by the method comprises a plurality of antibodies of Formula II or IV having four acceptor glutamines per antibody, wherein the composition is characterized by a mean Z (or R):

antibody ratio (e.g. mean DAR) of between between 3.0 and 4.0, or between 3.5 and 4.0, or between 3.6 and 4.0).

In one aspect provided is a method for evaluating antibodies, comprising the steps of:

a) providing a first and second antibody sample each comprising a plurality of antibodies comprising at least one acceptor glutamine residue, wherein the first and second antibody-containing samples differ from one another with respect to antibody sequence (e.g. hypervariable region sequence), wherein substantially all of the antibody present in the first sample is of the same sequence and substantially all of the antibody present in the second sample is of the same sequence;

b) immobilizing each of said first and second antibody samples separately on a separate solid support to provide a first and second support comprising immobilized antibody, optionally comprising a step of applying each antibody-containing sample separately to a solid support; and c) reacting each of said first and second immobilized antibody samples of step (c) with a linking reagent comprising a moiety of interest, in the presence of a TGase, under conditions sufficient to obtain a first and second antibody comprising an acceptor glutamine linked (covalently) to a moiety-of-interest via a linker.

In one aspect provided is a method for evaluating antibodies, comprising the steps of:

a) providing a first and second antibody sample each comprising a plurality of antibodies comprising at least one acceptor glutamine residue, wherein the first and second antibody-containing samples share antibody amino acid sequence (e.g. antibody CDR sequences);

b) immobilizing each of said first and second antibody samples separately on a solid support to provide a first and second support comprising immobilized antibody, optionally comprising a step of applying each antibody-containing sample separately to a solid support;

c) reacting said first immobilized antibody sample of step (b) with a first linking reagent comprising a moiety of interest, in the presence of a TGase, under conditions sufficient to obtain a first antibody comprising an acceptor glutamine linked (covalently) to a moiety-of-interest via a linker; and d) reacting said second immobilized antibody sample of step (b) with a second linking reagent comprising a moiety of interest, wherein the second linking reagent differs in structure from the first linking reagent, in the presence of a TGase, under conditions sufficient to obtain a second antibody comprising an acceptor glutamine linked (covalently) to a moiety-of-interest via a linker.

In one aspect of the evaluation methods, the first and second linking reagent differ in the structure of the moiety of interest. In one aspect of the evaluation methods, the first and second antibody samples in step b) are reacted in separate containers. In one aspect of the evaluation methods, the first and second antibody samples are specific for the same antigen.

In one aspect of the evaluation methods, said first and second antibody sample differ with respect to isotype. In one aspect of the evaluation methods, the method further comprises a step comprising: evaluating the antibodies linked to a moiety-of-interest for a characteristic of interest. Optionally, said step of evaluating antibodies for a characteristic of interest comprises evaluating antibodies for one or more properties selected from the group consisting of: binding to an antigen of interest, binding to an Fc receptor, Fc-domain mediated effector function(s), agonistic or antagonistic activity at a polypeptide to which the antibody, ability to cause the death of a cell expressing the antigen of interest, stability in vitro or in vivo, and susceptibility to aggregate in solution. Optionally, the characteristic of interest is suitability for use as an antibody-drug conjugate. In one embodiment, said step of evaluating antibodies for suitability of the antibodies for use as an antibody-drug conjugate comprises evaluating the antibodies for their ability to cause the death of a cell expressing the antigen of interest.

In another aspect provided is a solid support comprising an antibody (e.g. a plurality of antibodies) comprising an acceptor glutamine linked (covalently) to a moiety-of-interest via a linker. Optionally, the solid support comprises an antibody capture reagent which binds the antibody. Optionally, the antibody is non-covalently bound to the antibody capture reagent. Optionally, the antibody is an antibody or antibody fragment comprising a functionalized acceptor glutamine residue having a structure of formula II, formula IVa or formula IVb.

In one aspect of any of the methods or compositions, said linker is a linker comprising a NH—$(C)_n$— moiety, where $(C)_n$ is a substituted or unsubstituted carbon chain, wherein any carbon of the chain is optionally substituted with a O, N or S atom of an ether, ester, thioether, thioester, amine, alkylamine, amide, or alkylamide. Optionally, said linker is a linker of formula Ia or Ib. In one embodiment, V is a conditionally-cleavable moiety following prior conditional transformation, which can be cleaved or transformed by a chemical, photochemical, physical, biological, or enzymatic process, such as a di-, tri-, tetra-, or oligopeptide. In one embodiment, Y is a self-eliminating spacer system. In one embodiment, Y is a non-self-elimination spacer system. In one embodiment, any of r, r', q and/or q' represent the degree of branching. In one embodiment, any of r, r', q and/or q' represent the degree of polymerization.

In one aspect of any of the methods or compositions, the antibodies are tetrameric antibodies. In one aspect of any of the methods, the antibodies are full length antibodies. In one aspect of any of the methods, the antibodies are antibody fragments comprising at least a portion of an Fc region such that the antibody is capable of being bound by the Fc region to a solid support.

In one aspect of any of the methods or compositions, the moiety of interest (or Z) is a cytotoxic anti-cancer agent. Optionally, Z is selected from the group consisting of taxanes, anthracyclines, camptothecins, epothilones, myto- mycins, combretastatins, vinca alkaloids, nitrogen mustards, maytansinoids, calicheamycins, duocarmycins, tubulysins, dolastatins and auristatins, enediynes, pyrrolobenzodiaz- epines, and ethylenimines. Optionally, Z is a hydrophobic compound. Optionally, Z is an organic compound having a molecular weight of at least 400 g/mol. Optionally, Z is a negatively charged compound.

Any of the methods or compositions herein can further be characterized as comprising any step or embodiment described in the application, including notably in the "Detailed Description of the Invention"). Further provided are an antibody or antibody-bound solid support obtainable by any of present methods. Further provided are pharmaceutical or diagnostic formulations of the antibodies. Further provided are methods of using an antibody in a method of treatment or diagnosis.

These and additional advantageous aspects and features of the invention may be further described elsewhere herein.

DETAILED DESCRIPTION OF THE INVENTION

Definitions

Figure 1:
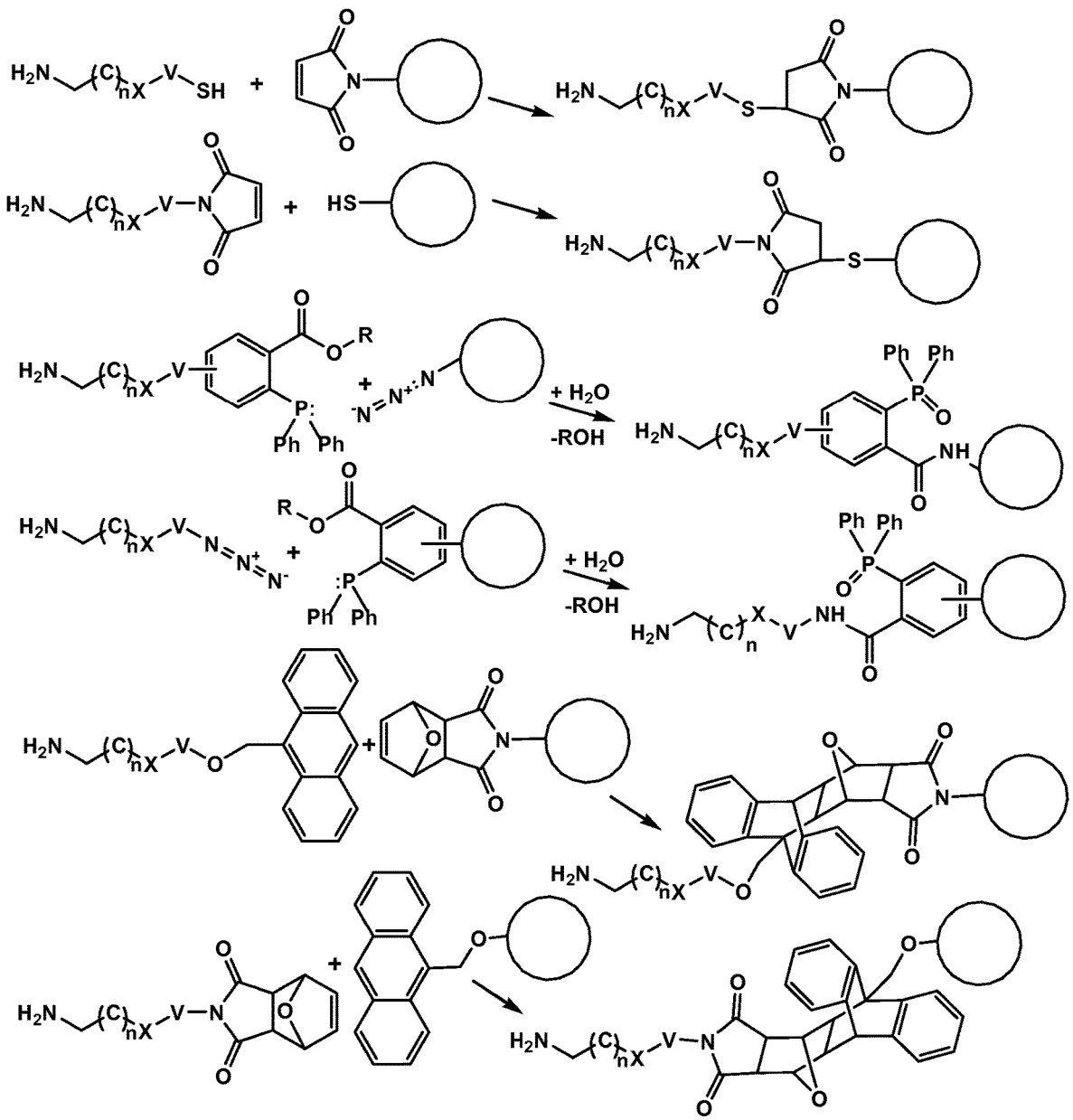
FIG. 1 shows reaction schemes for thio-maleimide additions, Staudinger ligations, and Diels-Alder cycloadditions, where reactive groups of linking reagents having a single reactive functionality combine with complementary reactive group attached to a therapeutic or diagnostic moiety.

As used in the specification, "a" or "an" may mean one or more. As used in the claim(s), when used in conjunction with the word "comprising", the words "a" or "an" may mean one or more than one.

Where "comprising" is used, this can optionally be replaced by "consisting essentially of", or optionally by "consisting of".

The term "transglutaminase", used interchangeably with "TGase" or "TG", refers to an enzyme capable of cross-linking proteins through an acyl-transfer reaction between the γ-carboxamide group of peptide-bound glutamine and the ε-amino group of a lysine or a structurally related primary amine such as amino pentyl group, e.g. a peptide-bound lysine, resulting in a ε-(γ-glutamyl)lysine isopeptide bond. TGases include, inter alia, bacterial transglutaminase (BTG) such as the enzyme having EC reference EC 2.3.2.13 (protein-glutamine-γ-glutamyltransferase).

The term "acceptor glutamine", when referring to an amino acid residue of an antibody, means a glutamine residue that, under suitable conditions, is recognized by a TGase and can be cross-linked by a TGase through a reaction between the glutamine and a lysine or a structurally related primary amine such as amino pentyl group. Optionally, the acceptor glutamine is a surface-exposed glutamine.

The term "TGase recognition tag", refers to a sequence of amino acids that when incorporated into (e.g. appended to) a polypeptide sequence, under suitable conditions, is recognized by a TGase and leads to cross-linking by the TGase through a reaction between an amino acid side chain within the sequence of amino acids and a reaction partner. The TGase recognition tag is a sequence that is not naturally present in the polypeptide comprising the TGase recognition tag. Cross-linking by the TGase may be through a reaction between a glutamine residue (an acceptor glutamine) within the TGase recognition tag and a lysine or a structurally related primary amine such as amino pentyl group.

The term "antibody" herein is used in the broadest sense and specifically includes full-length monoclonal antibodies, polyclonal antibodies, multispecific antibodies (e.g., bispecific antibodies), and antibody fragments, so long as they exhibit the desired biological activity. Various techniques relevant to the production of antibodies are provided in, e.g., Harlow, et al., ANTIBODIES: A LABORATORY MANUAL, Cold Spring Harbor Laboratory Press, Cold Spring Harbor, N.Y., (1988).

The term "antibody derivative", as used herein, comprises a full-length antibody or a fragment of an antibody, preferably comprising at least antigen-binding or variable regions thereof, wherein one or more of the amino acids are chemically modified, e.g., by alkylation, PEGylation, acylation, ester formation or amide formation or the like. This includes, but is not limited to, PEGylated antibodies, cysteine-PEGylated antibodies, and variants thereof.

By "constant region" of an antibody as defined herein is meant the region of the antibody that is encoded by one of the light or heavy chain immunoglobulin constant region genes. By "constant light chain" or "light chain constant region" as used herein is meant the region of an antibody encoded by the kappa (Ckappa) or lambda (Clambda) light chains. The constant light chain typically comprises a single domain, and as defined herein refers to positions 108-214 of Ckappa, or Clambda, wherein numbering is according to the EU index (Kabat et al., 1991, Sequences of Proteins of Immunological Interest, 5th Ed., United States Public Health Service, National Institutes of Health, Bethesda). By "constant heavy chain" or "heavy chain constant region" as used herein is meant the region of an antibody encoded by the mu, delta, gamma, alpha, or epsilon genes to define the antibody's isotype as IgM, IgD, IgG, IgA, or IgE, respectively. For full length IgG antibodies, the constant heavy chain, as defined herein, refers to the N-terminus of the CH1 domain to the C-terminus of the CH3 domain, thus comprising positions 118-447, wherein numbering is according to the EU index.

By "Fab" or "Fab region" as used herein is meant the polypeptide that comprises the VH, CH1, VL, and CL immunoglobulin domains. Fab may refer to this region in isolation, or this region in the context of a full length antibody, antibody fragment or Fab fusion protein, or any other antibody embodiments as outlined herein.

By "Fv" or "Fv fragment" or "Fv region" as used herein is meant a polypeptide that comprises the VL and VH domains of a single antibody.

By "Fc" or "Fc region", as used herein is meant the polypeptide comprising the constant region of an antibody excluding the first constant region immunoglobulin domain. Thus Fc refers to the last two constant region immunoglobulin domains of IgA, IgD, and IgG, and the last three constant region immunoglobulin domains of IgE and IgM, and the flexible hinge N-terminal to these domains. For IgA and IgM, Fc may include the J chain. For IgG, Fc comprises immunoglobulin domains Cγ2 and Cγ3 and the hinge between Cγ1 and Cγ2. Although the boundaries of the Fc region may vary, the human IgG heavy chain Fc region is usually defined to comprise residues C226, P230 or A231 to its carboxyl-terminus, wherein the numbering is according to the EU index. Fc may refer to this region in isolation, or this region in the context of an Fc polypeptide, as described below. By "Fc polypeptide" as used herein is meant a polypeptide that comprises all or part of an Fc region. Fc polypeptides include antibodies, Fc fusions, isolated Fcs, and Fc fragments.

By "full length antibody" as used herein is meant the structure that constitutes the natural biological form of an antibody, including variable and constant regions. For example, in most mammals, including humans and mice, the full length antibody of the IgG isotype is a tetramer and consists of two identical pairs of two immunoglobulin chains, each pair having one light and one heavy chain, each light chain comprising immunoglobulin domains VL and CL, and each heavy chain comprising immunoglobulin domains VH, Cγ1, Cγ2, and Cγ3. In some mammals, for example in camels and llamas, IgG antibodies may consist of only two heavy chains, each heavy chain comprising a variable domain attached to the Fc region.

By "variable region" as used herein is meant the region of an antibody that comprises one or more Ig domains substantially encoded by any of the VL (including Vkappa and Vlambda) and/or VH genes that make up the light chain (including kappa and lambda) and heavy chain immunoglobulin genetic loci respectively. A light or heavy chain variable region (VL and VH) consists of a "framework" or "FR" region interrupted by three hypervariable regions referred to as "complementarity determining regions" or "CDRs". The extent of the framework region and CDRs have been precisely defined, for example as in Kabat (see "Sequences of Proteins of Immunological Interest," E. Kabat et al., U.S. Department of Health and Human Services, (1983)), and as in Chothia. The framework regions of an antibody, that is the combined framework regions of the constituent light and heavy chains, serves to position and align the CDRs, which are primarily responsible for binding to an antigen.

By "amino acid modification" herein is meant an amino acid substitution, insertion, and/or deletion in a polypeptide sequence. The preferred amino acid modification herein is a substitution. By "amino acid modification" herein is meant an amino acid substitution, insertion, and/or deletion in a polypeptide sequence. By "amino acid substitution" or "substitution" herein is meant the replacement of an amino acid at a given position in a protein sequence with another amino acid. For example, the substitution Y50W refers to a variant of a parent polypeptide, in which the tyrosine at position 50 is replaced with tryptophan. A "variant" of a polypeptide refers to a polypeptide having an amino acid sequence that is substantially identical to a reference polypeptide, typically a native or "parent" polypeptide. The polypeptide variant may possess one or more amino acid substitutions, deletions, and/or insertions at certain positions within the native amino acid sequence.

"Conservative" amino acid substitutions are those in which an amino acid residue is replaced with an amino acid residue having a side chain with similar physicochemical properties. Families of amino acid residues having similar side chains are known in the art, and include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine).

An antibody having a "biological characteristic" of a reference antibody, is one that possesses one or more of the biological characteristics of that antibody that distinguish it from other antibodies that bind to the same antigen.

An "isolated" molecule is a molecule that is the predominant species in the composition wherein it is found with respect to the class of molecules to which it belongs (i.e., it makes up at least about 50% of the type of molecule in the composition and typically will make up at least about 70%, at least about 80%, at least about 85%, at least about 90%, at least about 95%, or more of the species of molecule, e.g., peptide, in the composition). Commonly, a composition of an antibody molecule will exhibit 98%, 98%, or 99% homogeneity for antibody molecules in the context of all present peptide species in the composition or at least with respect to substantially active peptide species in the context of proposed use.

The term "reactive moiety" herein refers to a moiety that can be coupled with another moiety without prior activation or transformation.

The term "protecting group" refers to a group that temporarily protects or blocks, i.e., intended to prevent from reacting, a functional group, e.g, an amino group, a hydroxyl group, or a carboxyl group, during the transformation of a first molecule to a second molecule.

The phrase "moiety that improves the pharmacokinetic properties", when referring to a compound (e.g. an antibody) refers to a moiety that changes the pharmacokinetic properties of the one or more moieties Z in such a way that a better therapeutic or diagnostic effect can be obtained. The moiety can for example increase the water solubility, increase the circulation time, or reduce immunogenicity.

The phrase "linking group" refers to a structural element of a compound that links one structural element of said compound to one or more other structural elements of said same compound.

The phrase "a number representing degree of branching" is used to denote that the subscript number next to a closing bracket represents how many units of the moiety within the brackets are attached to the moiety directly to the left of the corresponding opening bracket For example, A-(B)$_b$ with b being a number representing a degree of branching means that b units B are all directly attached to A This means that when b is 2, the formula reduces to B-A-B.

The phrase "a number representing degree of polymerization" is used to denote that the subscript number next to a closing bracket represents how many units of the moiety within the brackets are connected to each other. For example, A-(B)$_1$, with b being a number representing a degree of polymerization means that when b is 2, the formula reduces to A-B-B.

As used herein, "alkyl" refers to a straight or branched hydrocarbon chain that comprises a fully saturated (no double or triple bonds) hydrocarbon group. The alkyl group may have, for example, 1 to 20 carbon atoms (whenever it appears herein, a numerical range such as "1 to 20" refers to each integer in the given range; e.g., "1 to 20 carbon atoms" means that the alkyl group may consist of 1 carbon atom, 2 carbon atoms, 3 carbon atoms, etc., up to and including 20 carbon atoms, although the present definition also covers the occurrence of the term "alkyl" where no numerical range is designated). The alkyl group of the compounds may be designated as "$C_1$-$C_4$ alkyl" or similar designations. By way of example only, "$C_1$-$C_4$ alkyl" indicates that there are one to four carbon atoms in the alkyl chain, i.e., the alkyl chain is selected from methyl, ethyl, propyl, iso-propyl, n-butyl, iso-butyl, sec-butyl, and t-butyl. Typical alkyl groups include, but are in no way limited to, methyl, ethyl, propyl, isopropyl, butyl, isobutyl, tertiary butyl, pentyl and hexyl. The alkyl group may be substituted or unsubstituted.

As used herein, the term "heteroalkyl" refers to a straight or branched alkyl group that contains one or more heteroatoms, that is, an element other than carbon (including but not limited to oxygen, sulfur, nitrogen, phosphorus) in place of one or more carbon atoms.

Whenever a group is described as being "substituted" that group substituted with one or more of the indicated substituents. If no substituents are indicated, it is meant that the indicated "substituted" group may be substituted with one or more group(s) individually and independently selected from alkyl, alkenyl, alkynyl, cycloalkyl, cycloalkenyl, cycloalkynyl, heteroalkyl, aryl, heteroaryl, heteroalicyclyl, aralkyl, heteroaralkyl, (heteroalicyclyl)alkyl, hydroxy, alkoxy, aryloxy, acyl, mercapto, alkylthio, arylthio, cyano, halogen, thiocarbonyl, carbamyl, thiocarbamyl, amido, sulfonamido, sulfonamido, carboxy, isocyanato, thiocyanato, isothiocyanato, nitro, silyl, sulfenyl, sulfinyl, sulfonyl, haloalkyl, haloalkoxy, trihalomethanesulfonyl, trihalomethanesulfonamido, an amino, a mono-substituted amino group and a di-substituted amino group, and protected derivatives thereof.

Where the number of substituents is not specified (e.g. haloalkyl), there may be one or more substituents present. For example "haloalkyl" may include one or more of the same or different halogens. As another example, "$C_1$-$C_3$ alkoxyphenyl" may include one or more of the same or different alkoxy groups containing one, two or three atoms.

Producing Antibodies

Antibodies may be produced by a variety of techniques known in the art. Typically, they are produced by immunization of a non-human animal, preferably a mouse, with an immunogen comprising a polypeptide, or a fragment or derivative thereof, typically an immunogenic fragment, for which it is desired to obtain antibodies (e.g. a human polypeptide). The step of immunizing a non-human mammal with an antigen may be carried out in any manner well known in the art for stimulating the production of antibodies in a mouse (see, for example, E. Harlow and D. Lane, Antibodies: A Laboratory Manual., Cold Spring Harbor Laboratory Press, Cold Spring Harbor, N.Y. (1988), the entire disclosure of which is herein incorporated by reference). Other protocols may also be used as long as they result in the production of B cells expressing an antibody directed to the antigen used in immunization. Lymphocytes from a non-immunized non-human mammal may also be isolated, grown in vitro, and then exposed to the immunogen in cell culture. The lymphocytes are then harvested and the fusion step described below is carried out. For preferred monoclonal antibodies, the next step is the isolation of splenocytes from the immunized non-human mammal and the subsequent fusion of those splenocytes with an immortalized cell in order to form an antibody-producing hybridoma. The hybridoma colonies are then assayed for the production of antibodies that specifically bind to the polypeptide against which antibodies are desired. The assay is typically a colorimetric ELISA-type assay, although any assay may be employed that can be adapted to the wells that the hybridomas are grown in. Other assays include radioimmunoassays or fluorescence activated cell sorting. The wells positive for the desired antibody production are examined to determine if one or more distinct colonies are present. If more than one colony is present, the cells may be re-cloned and grown to ensure that only a single cell has given rise to the colony producing the desired antibody. After sufficient growth to produce the desired monoclonal antibody, the growth media containing monoclonal antibody (or the ascites fluid) is separated away from the cells and the monoclonal antibody present therein is purified. Purification is typically achieved by gel electrophoresis, dialysis, chromatography using protein A or protein G-Sepharose, or an anti-mouse Ig linked to a solid support such as agarose or Sepharose beads (all described, for example, in the Antibody Purification Handbook, Biosciences, publication No. 18-1037-46, Edition AC, the disclosure of which is hereby incorporated by reference).

Additionally, a wide range of antibodies are available in the scientific and patent literature, including DNA and/or amino acid sequences, or from commercial suppliers. Examples of antibodies include antibodies that recognize an antigen expressed by a target cell that is to be eliminated, for example a proliferating cell or a cell contributing to a pathology. Examples include antibodies that recognize tumor antigens, microbial (e.g. bacterial) antigens or viral antigens. Other examples include antigens present on immune cells that are contributing to inflammatory or autoimmune disease, including rejection of transplanted tissue (e.g. antigens present on T cells (CD4 or CD8 T cells).

Antibodies will typically be directed to a pre-determined antigen. As used herein, the term "bacterial antigen" includes, but is not limited to, intact, attenuated or killed bacteria, any structural or functional bacterial protein or carbohydrate, or any peptide portion of a bacterial protein of sufficient length (typically about 8 amino acids or longer) to be antigenic. As used herein, the term "viral antigen" includes, but is not limited to, intact, attenuated or killed whole virus, any structural or functional viral protein, or any peptide portion of a viral protein of sufficient length (typically about 8 amino acids or longer) to be antigenic. As used herein, the terms "cancer antigen" and "tumor antigen" are used interchangeably and refer to antigens that are differentially expressed by cancer cells and can thereby be exploited in order to target cancer cells.

Wild-type full-length IgG antibodies of human isotype will possess a conserved acceptor glutamine at residue 295 of the heavy chain which when in non-glycosylated form will be accessible to a TGase and therefore reactive with a compound of Formula I in the presence of a TGase, under suitable conditions, to form a conjugate from the antibody and the compound of Formula II or IV. The antibody will lack glycosylation at the asparagine at residue 297 of the heavy chain.

In one embodiment, the antibodies or antibody samples that are provided comprise a constant region and/or Fc region of human origin, optionally a human IgG1, IgG2, IgG3 or IgG4 isotype. Optionally the antibodies or antibody samples that are provided comprise a more than one human IgG1, IgG2, IgG3 or IgG4 isotype, i.e. antibody samples are of different isotypes. In one embodiment, the antibodies or antibody samples comprise a wild-type (naturally occurring) human heavy and/or light chain constant region sequence (representing a full-length human constant region or a fragment thereof, e.g. a contiguous sequence of at least 20, 50, 60, 75 or 100 amino acid residues of a human constant region). Preferably the antibodies or antibody samples comprise a human heavy and/or light chain constant region (e.g. a full-length heavy and/or light chain human constant region) having at least 95, 98, or 99% amino acid identity to a naturally occurring human constant region sequence. Optionally the constant region further comprises one or more (e.g. 2, 3, 4, 5 or more) amino acid substitution(s), optionally wherein said substitution(s) is the replacement of an amino acid residue by a glutamine. Optionally, the wild-type constant region sequence comprises one or more single amino acid substitutions. Optionally, the wild-type constant region sequence comprises one or more amino acid substitutions, wherein all the substitutions are naturally occurring amino acids. Preferably the wild-type constant region sequence is free of an enzymatic recognition tag, i.e. a sequence of 2, 3, 4, 5 or more residues specifically recognized by an enzyme, for example an enzyme that conjugates a moiety of interest to an antibody, a formylglycine-generating enzyme, a sortase, etc.

While antibodies can be used directly without modification, additional or alternative sites reactive with a compound of Formula I in the presence of a TGase can optionally be created by engineering the antibodies, for example to explore and compare efficacy where more than one glutamine is conjugated on each heavy chain. The compounds include glutamine engineered antibodies where one or more amino acids of a wild-type or parent antibody are replaced with (substituted by) a glutamine amino acid, or where a glutamine residue, optionally together with other amino acid residues, is introduced or added to a wild-type or parent antibody (e.g. wherein the glutamine residue is added to an antibody fragment).

It should be noted that a single site mutation that provides a glutamine that is accessible to a TGase may yield more than one engineered glutamine residue that can be conjugated if the antibody comprises more than one engineered chain. For example, a single site mutation will yield two engineered glutamine residues in a tetrameric IgG due to the dimeric nature of the IgG antibody. The engineered glutamine residues will be in addition to any acceptor glutamine already present in an antibody, if any. The glutamine amino acid residues that are reactive, in the presence of a TGase under suitable conditions, with a compound of Formula I may be located in the heavy chain, typically in the constant domain.

In one embodiment, an asparagine at amino acid position 297 (EU Index of Kabat (1991)) is substituted with a glutamine residue. The antibody will have a constant region with a N297Q substitution (a N297Q variant antibody). An antibody having a N297Q substitution and a glutamine at residue 295 (EU Index of Kabat (1991) will therefore have two acceptor glutamines and thus two conjugation sites per heavy chain. In tetravalent form will therefore have four conjugates per antibody. Such antibody will also have the advantage that no enzymatic deglycosylation step is needed prior to reaction with TGase since such antibody will naturally lack glycosylation.

Glutamine engineered antibodies can be prepared by a variety of methods which include, but are not limited to, isolation from a natural source (in the case of naturally occurring amino acid sequence variants), preparation by site-directed (or oligonucleotide-mediated) mutagenesis (Carter (1985) et al Nucleic Acids Res. 13:4431-4443; Kunkel et al (1987) Proc. Natl. Acad. Sci. USA 82:488; Liu et al (1998) J. Biol. Chem. 273:20252-20260), PCR mutagenesis (Higuchi, (1990) in PCR Protocols, pp. 177-183, Academic Press; Ito et al (1991) Gene 102:67-70; Bernhard et al (1994) Bioconjugate Chem. 5: 126-132; and Vallette et al (1989) Nuc. Acids Res. 17:723-733) and cassette mutagenesis (Wells et al (1985) Gene 34:315-323) of an earlier prepared DNA encoding the polypeptide. Mutagenesis protocols, kits, and reagents are commercially available, e.g. QuikChange® Multi Site-Direct Mutagenesis Kit (Stratagene, La Jolla, Calif.). Single mutations are also generated by oligonucleotide directed mutagenesis using double stranded plasmid DNA as template by PCR based mutagenesis (Sambrook and Russel, (2001) Molecular Cloning: A Laboratory Manual, 3rd edition; Zoller et al (1983) Methods Enzymol. 100:468-500; ZoDer, M J. and Smith, M. (1982) Nucl. Acids Res. 10:6487-6500). Variants of recombinant antibodies may be constructed also by restriction fragment manipulation or by overlap extension PCR with synthetic oligonucleotides. Mutagenic primers encode the cysteine codon replacement(s). Standard mutagenesis techniques can be employed to generate DNA encoding such mutant cysteine engineered antibodies (Sambrook et al Molecular Cloning, A Laboratory Manual. Cold Spring Harbor Laboratory Press, Cold Spring Harbor, N.Y., 1989; and Ausubel et al Current Protocols in Molecular Biology, Greene Publishing and Wiley-Interscience, New York. N.Y., 1993).

Antibodies may be chemically synthesized using known oligopeptide synthesis methodology or may be prepared and purified using recombinant technology. In vitro protein synthesis may be performed using manual techniques or by automation.

Fragments and derivatives of antibodies (which are encompassed by the term "antibody" or "antibodies" as used in this application, unless otherwise stated or clearly contradicted by context), can be produced by techniques that are known in the art. "Fragments" comprise a portion of the intact antibody, generally the antigen binding site or variable region. Examples of antibody fragments include Fab, Fab', Fab'-SH, F(ab')2, and Fv fragments; diabodies; any antibody fragment that is a polypeptide having a primary structure consisting of one uninterrupted sequence of contiguous amino acid residues (referred to herein as a "single-chain antibody fragment" or "single chain polypeptide"), including without limitation (1) single-chain Fv molecules (2) single chain polypeptides containing only one light chain variable domain, or a fragment thereof that contains the three CDRs of the light chain variable domain, without an associated heavy chain moiety and (3) single chain polypeptides containing only one heavy chain variable region, or a fragment thereof containing the three CDRs of the heavy chain variable region, without an associated light chain moiety; and multispecific antibodies formed from antibody fragments. Included, inter alia, are a nanobody, domain antibody, single domain antibody or a "dAb". Where the antibody is to be bound to a solid support by its Fc region, the antibody fragment will comprise at least a portion of an Fc region such that the antibody is capable of being bound by the Fc region to the solid support.

The DNA of a hybridoma producing an antibody may be modified so as to encode the desired antibody. The modified DNA is then inserted into an expression vector and used to transform or transfect an appropriate cell, which then expresses the desired antibody.

The fragment may comprise a variable region domain that will generally be fused (directly or indirectly with intervening amino acid sequences) to a TGase recognition tag comprising at least one, two or more acceptor glutamine residue.

The antibody fragment can have a variable region domain that is monomeric and comprises an immunoglobulin heavy (VH) or light (VL) chain variable domain, or is dimeric and contains VH—VH, VH-VL or VL-VL dimers in which the VH and VL chains are non-covalently associated or covalently coupled. Preferably each VH and/or VL domain is covalently attached at a C-terminal amino acid to at least one other antibody domain or a fragment thereof, for example an Fc region or portion thereof.

Once an antibody or antibody fragment is obtained, it can be applied to a solid support such that the antibody is immobilized, for subsequent reaction of the immobilized antibody with TGase and a linker comprising a moiety of interest, e.g. a reactive moiety (R) or a moiety Z such as a drug. In order to generate antibodies bound to a moiety of interest via a linking reagent by this process, antibody bound to a solid support can be brought into contact with linking reagents (e.g. lysine based linkers of formulae Ia or Ib) and TGase enzyme under conditions suitable for the TGase to catalyze a covalent bond between the lysine-based linker and an acceptor glutamine in the primary sequence of the antibody or antibody fragment. Lysine based linker and TGase enzyme can thus be applied (introduced) to the solid support under suitable conditions.

Alternatively, the antibody can first be reacted in liquid phase (solution), in the presence of TGase and a linker comprising a moiety of interest to generate an antibody (e.g. of Formula II) having a reactive linker conjugated thereto. The resulting antibody (e.g. of Formula II) can then be introduced to a solid phase so as to immobilize the antibody having a reactive linker conjugated thereto. The immobilized antibody can then subsequently be reacted with a compound having a complementary reactive group and a moiety of interest Z.

Generally, the solid support may be any suitable insoluble, functionalized material to which the antibodies can be reversibly attached, either directly or indirectly, allowing them to be separated from unwanted materials, for example, excess reagents, contaminants, and solvents. Examples of solid supports include, for example, functionalized polymeric materials, e.g., agarose, or its bead form Sepharose®, dextran, polystyrene and polypropylene, or mixtures thereof; compact discs comprising microfluidic channel structures; protein array chips; pipet tips; membranes, e.g., nitrocellulose or PVDF membranes; and microparticles, e.g., paramagnetic or non-paramagnetic beads. In some embodiments, an affinity medium will be bound to the solid support and the antibody will be indirectly attached to solid support via the affinity medium. In one aspect, the solid support comprises a protein A affinity medium or protein G affinity medium. A "protein A affinity medium" and a "protein G affinity medium" each refer to a solid phase onto which is bound a natural or synthetic protein comprising an Fc-binding domain of protein A or protein G, respectively, or a mutated variant or fragment of an Fc-binding domain of protein A or protein G, respectively, which variant or fragment retains the affinity for an Fc-portion of an antibody. Protein A and Protein G are bacterial cell wall proteins that have binding sites for the Fc portion of mammalian IgG. The capacity of these proteins for IgG varies with the species. In general, IgGs have a higher affinity for Protein G than for Protein A, and Protein G can bind IgG from a wider variety of species. The affinity of various IgG subclasses, especially from mouse and human, for Protein A varies more than for Protein G. Protein A can, therefore, be used to prepare isotypically pure IgG from some species. Protein L has an affinity for kappa light chains from various species. It can be used to purify monoclonal or polyclonal IgG, IgA, and IgM as well as Fab, $F(ab')_2$, and recombinant scFv fragments that contain kappa light chains When covalently attached to a solid matrix, such as cross-linked agarose, these proteins can be used to capture and purify antigen-antibody complexes from biochemical solutions. Commercially available products include, e.g., Protein G, A or L bonded to agarose or sepharose beads, for example EZview™ Red Protein G Affinity Gel is Protein G covalently bonded to 4% Agarose beads (Sigma Aldrich Co); or POROS® A, G, and CaptureSelect® HPLC columns (Invitrogen Inc.).Affinity capture reagents are also described, for example, in the Antibody Purification Handbook, Biosciences, publication No. 18-1037-46, Edition AC, the disclosure of which is hereby incorporated by reference).

After any reaction step carried out while antibody is immobilized on the solid support (TGase conjugation and/or reaction with complementary reactive groups R and R'), a washing step can be performed to remove any unreacted materials. Optionally, unreacted compounds are recovered; optionally, unreacted linking reagent and/or TGase are re-applied to the solid support to provide for higher completion of the reaction between antibody and substrate (linking reagent).

In order to recover antibodies bound to a moiety of interest via a linking reagent, immobilized antibody conjugates can subsequently be eluted from the solid support to provide antibody conjugate compositions. Methods of eluting proteins from solid supports are known in the art and the skilled practitioner will be able to select an appropriate buffer for elution. For example, in embodiments, where the solid support comprises protein A or protein G resin, the antibody conjugates can be eluted with standard low pH buffers for elution from protein A or protein G columns.

In order to generate antibodies covalently bound to a solid support, antibodies not covalently bound to the solid support can be eluted, leaving a solid support functionalized with antibodies.

Lysine-Based Linkers

The antibodies will be conjugated to a moiety-of-interest via a linking reagent that can be attached, by the action of a TGase, at a glutamine residue (Q) within the sequence of the antibody. The linking reagent comprises a lysine derivative (Lys), or a functional equivalent thereof, that is connected to at least one moiety of interest (Z), optionally a reactive group (R).

Examples of lysine based linkers and their synthesis is provided in PCT patent application number PCT/EP2012/076606 (WO2013/092983) filed 21 Dec. 2012, the disclosure of which is incorporated herein by reference, including the synthesis methods of Example 1 and reaction schemes FIGS. 15, 16A, 16B and 16C.

The lysine derivative can be a 2 to 20 alkyl or heteroalkyl chain, or a functional equivalent thereof, with an $H_2N$, $H_2NOCH_2$, $H_2NCH_2$ (aminomethylene) group or a protected $H_2N$, $H_2NOCH_2$, $H_2NCH_2$ group positioned at one or more ends of the alkyl or heteroalkyl chain. The heteroalkyl chain can be a chain of 3 to 20 atoms where one or more non-terminal atoms can be other than carbon, for example oxygen, sulfur, nitrogen, or other atoms. The oxygen, sulfur, or nitrogen atom can be of an ether, ester, thioether, thioester, amino, alkylamino, amido or alkylamido functionality within the carbon chain.

The heteroalkyl chain can be an oligo (ethylene oxide) chain. The functionality within the alkyl or heteroalkyl chain can be included to couple the reactive group to the $H_2N$, $H_2NOCH_2$, $H_2NCH_2$ group or protected $H_2N$, $H_2NOCH_2$, $H_2NCH_2$ group. The alkyl or heteroalkyl chain can be substituted or unsubstituted. The substituents can be alkyl groups, aryl groups, alkyl aryl groups, carboxylic acid groups, amide groups, hydroxy groups, or any other groups that do not compete with the amino group for, or inhibit, conjugation with a glutamine residue of the protein. Typically, when a substituent is present, its presence is in a convenient starting material, such as the carboxylic acid group of lysine, from which the lysine derivative results. The $H_2N$, $H_2NOCH_2$, $H_2NCH_2$ end of an alkyl or heteroalkyl chain is necessarily included in the linking reagent.

Exemplary starting materials for the functional equivalent of lysine can be an α,ω-diaminoalkane, for example, 1,2-diaminoethane, 1,3-diaminopropane, 1,4-diaminobutane, 1,5-diaminopentane, 1,6-diaminohexane, 1,7-diaminoheptane, 1,8-diaminooctane, 1,9-diaminononane, 1,10-diaminodecane, 1,11-diaminoundecane, or 1,12-diaminododecane. Other starting materials for the functional equivalent of a lysine derivative can be α,ω-diamino oligo (ethylene oxide), for example, $H_2N(CH_2CH_2O)_xCH_2CH_2NH_2$ where x is 1 to about 6. The α,ω-diamino oligo (ethylene oxide) can be a single oligomer or it can be a mixture of oligomers where x defines an average size. An exemplary protected $H_2NCH_2$ is the tert-butylcarbamate protected amine of tert-butyl N-(5-aminopentyl)carbamate (N-Boc-cadaverin).

The linking reagent, a pharmaceutically acceptable salt or solvate thereof, or an antibody-conjugated linking reagent may comprise the general Formula Ia or Ib. Formulae Ia (having an Z group) and Ib (having a R group) are shown as follows:

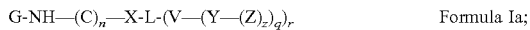  Formula Ia;

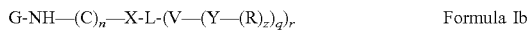  Formula Ib or a pharmaceutically acceptable salt or solvate thereof wherein:

G is an H, amine protecting group, or an antibody attached via an amide bond;

$(C)_n$ is a substituted or unsubstituted alkyl or heteroalkyl chain, optionally where the carbon adjacent to the nitrogen is unsubstituted, optionally wherein any carbon of the chain is substituted alkoxy, hydroxyl, alkylcarbonyloxy, alkyl-S—, thiol, alkyl-C(O)S—, amine, alkylamine, amide, or alkylamide (e.g. with a O, N or S atom of an ether, ester, thioether, thioester, amine, alkylamine, amide, or alkylamide);

n is an integer selected from among the range of 2 to 20, preferably 3 to 6;

X is NH, O, S, or absent;

L is a bond or a carbon comprising framework of 1 to 200 atoms substituted at one or more atoms, optionally wherein the carbon comprising framework is a linear hydrocarbon, a symmetrically or asymmetrically branched hydrocarbon, monosaccharide, disaccharide, linear or branched oligosaccharide (asymmetrically branched or symmetrically branched), an amino acid, a di-, tri-, tetra-, or oligopeptide, other natural linear or branched oligomers (asymmetrically branched or symmetrically branched), or a dimer, trimer, or higher oligomer (linear, asymmetrically branched or symmetrically branched) resulting from any chain-growth or step-growth polymerization process;

r is an integer selected from among 1, 2, 3 or 4;

q is an integer selected from among 1, 2, 3 or 4; and z is an integer selected from among 1, 2, 3 or 4;

V is independently absent, a bond or a continuation of a bond if L is a bond, a non-cleavable moiety or a conditionally-cleavable moiety, optionally following prior conditional transformation, which can be cleaved or transformed by a chemical, photochemical, physical, biological, or enzymatic process (e.g. cleavage of V ultimately leading to release of one or more moieties subsequently or ultimately linked to V, for example a Z moiety). In some embodiments, V is, preferably, a di-, tri-, tetra-, or oligopeptide as described below in the section entitled "The V Moiety";

Y is independently absent, a bond or a continuation of a bond if V is a bond or continuation of a bond, or a spacer system (e.g., a self-eliminating spacer system or a non-self-elimination spacer system) which is comprised of 1 or more spacers;

Z is a moiety that improves the pharmacokinetic properties, a therapeutic moiety or a diagnostic moiety; and R is a reactive moiety, preferably a moiety comprising an unprotected or protected thiol, maleimide, haloacetamide, o-phoshenearomatic ester, azide, fulminate, alkyne, cyanide, anthracene, 1,2,4,5-tetrazine, norbornene, other stained or otherwise electronically activated alkene or, optionally, a protected or unprotected amine when X is absent and L, V, or Y is other than a bond or a continuation of a bond. In an alternative embodiment R is a reactive moiety, preferably a moiety comprising an unprotected or protected thiol, an unprotected or protected amine, maleimide, haloacetamide, o-phoshenearomatic ester, azide, fulminate, alkyne, cyanide, anthracene, 1,2,4,5-tetrazine, norbornene, other stained or otherwise electronically activated alkene, provided that R is not an amine when n=5 and X, L, V and Y are absent. Optionally, R is not an amine when n=4 and X, L, V and Y are absent. When more than one R group is present in a compound of the formula Ib, the R groups will preferably be compatible such that no R group is a complementary reagent to any other R group.

The $(C)_n$ group may for example be a straight, branched and/or cyclic $C_{2-30}$ alkyl, $C_{2-30}$ alkenyl, $C_{2-30}$ alkynyl, $C_{2-30}$ heteroalkyl, $C_{2-30}$ heteroalkenyl, $C_{2-30}$ heteroalkynyl, optionally wherein one or more homocyclic aromatic compound radical or heterocyclic compound radical may be inserted; notably, any straight or branched $C_{2-5}$ alkyl, $C_{5-10}$ alkyl, $C_{11-20}$ alkyl, —O—$C_{1-5}$ alkyl, —O—$C_{5-10}$ alkyl, —O—$C_{11-20}$ alkyl, $CH_2$—$(CH_2$—O—$CH_2)_{1-12}$—$CH_2$ or $(CH_2$—$CH_2$—O—$)_{1-12}$, an amino acid, an oligopeptide, glycan, sulfate, phosphate or carboxylate.

In one example the $(C)_n$ group is a carbon comprising framework substituted with one or more O atoms. In one embodiment, the carbon adjacent to the nitrogen is substituted with an O atom. In one embodiment, the carbon adjacent to the nitrogen is unsubstituted. In one embodiment, the $(C)_n$ group is or comprises an ethylene oxide group, e.g. a $CH_2$—$(CH_2$—O—$CH_2)_n$—$CH_2$ group or an $(CH_2$—$CH_2$—O—$)_n$, where n is an integer from 1 to 10.

The L group can be a carbon comprising framework, where L is a linear hydrocarbon, a symmetrically or asymmetrically branched hydrocarbon, monosaccharide, disaccharide, linear or branched oligosaccharide (asymmetrically branched or symmetrically branched), an amino acid, a di-, tri-, tetra-, or oligopeptide, other natural oligomer, dimer, trimer, or higher oligomer (linear asymmetrically branched or symmetrically branched) resulting from any chain-growth or step-growth polymerization process. For example, L may comprise or be a straight, branched and/or cyclic $C_{2-30}$ alkyl, $C_{2-30}$ alkenyl, $C_{2-30}$ alkynyl, $C_{2-30}$ heteroalkyl, $C_{2-30}$ heteroalkenyl, $C_{2-30}$ heteroalkynyl, optionally wherein one or more homocyclic aromatic compound radical or heterocyclic compound radical may be inserted; notably, any straight or branched $C_{2-5}$ alkyl, $C_{5-10}$ alkyl, $C_{11-20}$ alkyl, —O—$C_{1-5}$ alkyl, —O—$C_{5-10}$ alkyl, —O—$C_{11-20}$ alkyl, $CH_2$—$(CH_2$—O—$CH_2)_{1-30}$—$CH_2$ or $(CH_2$—$CH_2$—O—$)_{1-30}$, e.g., $(CH_2$—$CH_2$—O—$)_{12}$, $(CH_2$—$CH_2$—O—$)_{1-24}$, an amino acid, an oligopeptide, glycan, sulfate, phosphate, carboxylate. Optionally, L is absent.

L, V and/or Y have r, q, and/or z sites of attachment for the respective V, Y, and Z or R groups, where r and q represent the degree of branching or polymerization. The sites of attachment can comprise a bond or comprise a functional group selected from an alkene, alkyne, ether, thioether, ester, thioester, amine, amide, alkylamide, or other functional group readily generated by a condensation or addition reaction.

In one example the carbon comprising framework of the L group is optionally substituted with one or more O atoms. In one embodiment, the L group comprises one or more ethylene oxide groups ($CH_2$—O—$CH_2$). Optionally, the L group comprises a carbon framework comprising a ($CH_2$—$CH_2$—O—$)_n$ group, wherein n is an integer selected among the range of 1 to 10 (e.g., 1, 2, 3, 4, 5, 6, 7, 8, 9 or 10).

In Formulae Ia, Ib, II, IVa and IVb, the linking group L links the aminopeptidyl moiety —NH—$(C)_n$—X to the reactive group R or Z, optionally through one or more V and/or Y moieties where present. L may be a bond connecting V, Y, R or Z directly to the aminopeptidyl moiety. In another aspect, however, L is a linking group that functionally links or spaces the one or more moieties V and/or Y reactive moiety R or moiety of interest (Z). In Formulae Ib, II and IVb, spacing improves efficiency and completion of BTGase coupling, make additionally the reactive moiety R more accessible to the reaction partner, for example when the reactive moiety is present on a lysine-based linker and coupled to the antibody and then brought into contact with a reaction partner. In Formulae Ia and IVa, the linking group L links the aminopeptidyl moiety —NH—$(C)_n$—X to the moiety-of-interest (Z), optionally through one or more V and/or Y moieties where present. L may be a bond connecting V, Y or Z directly to the aminopeptidyl moiety. In another aspect, however, L is a linking group that functionally links or spaces the one or more moieties V and/or Y reactive moiety Z. In Formulae Ia and IVa, spacing improves efficiency and completion of BTGase coupling, providing for highly homogenous compounds. In an antibodies comprising a functionalized acceptor glutamine of Formula IVa or IVb spacing may also provide for a better accessibility of V, which in the case of enzymatic cleavage or transformation of V, may improve the rate at which V is transformed and/or cleaved.

L and $(C)_n$ groups can be configured based on the overall structure of the linker that is to be used. Particularly when a multi-step method is used and the linker (e.g. the linker of Formula Ia or Ib is free of or does not comprise a large, charged or hydrophobic moiety (e.g. a cyclic, polycyclic or macrocyclic moiety), the L group may be a bond or a shorter carbon framework. For example, L may represent or comprise a carbon framework of 1, 2, 3, 4, 5, or 6 linear carbon atoms, unsubstituted or optionally substituted at one or more atoms. Preferably, where L additionally comprises other groups, the 5-20 linear carbon atoms will be adjacent to the $(C)_n$ group, or where present, the X group.

When a linker (e.g. the linker of Formula Ia or Ib or an antibody of Formula II, IVa or IVb) comprises a large, charged or hydrophobic moiety (e.g. a cyclic, polycyclic or macrocyclic moiety), for example, wherein V, Y and/or Z comprises a large, charged or hydrophobic moiety (e.g. a cyclic, polycyclic or macrocyclic moiety), the L group may be longer carbon framework. For example, L may represent or comprise a carbon framework of:

a) 2-30 linear carbon atoms optionally substituted at one or more atoms;

b) 2-15 linear carbon atoms optionally substituted at one or more atoms;

c) 5-20 linear carbon atoms optionally substituted at one or more atoms;

d) 5-30 linear carbon atoms optionally substituted at one or more atoms;

e) 5-15 linear carbon atoms optionally substituted at one or more atoms; or f) 4, 5 or 6 linear carbon atoms optionally substituted at one or more atoms.

Preferably, the 5-20 linear carbon atoms will be adjacent to (the continuation of) the $(C)_n$ group, or where present, the X group.

In some embodiments, L is a —(C=O)—$C_{1-6}$ alkyl group. In some embodiments, L is a $C_{1-6}$ alkoxy-$C_{1-6}$ alkyl group. In some embodiments, L is a —(C=O)—$C_{1-6}$ alkoxy-$C_{1-6}$ alkyl group. In some embodiments, L is a —(C=O)—$C_{10-20}$ alkyl group. In some embodiments, L is a $C_{1-6}$ alkyl group. In some embodiments, L is a $C_{10-20}$ alkyl group. In some embodiments, L is a —(C=O)—O—$C_{1-6}$ alkyl group. In some embodiments, L is a —(C=O)—O—$C_{2-20}$ alkyl group. In some embodiments, L is a —(C=O)— group. In some embodiments, L is selected from among

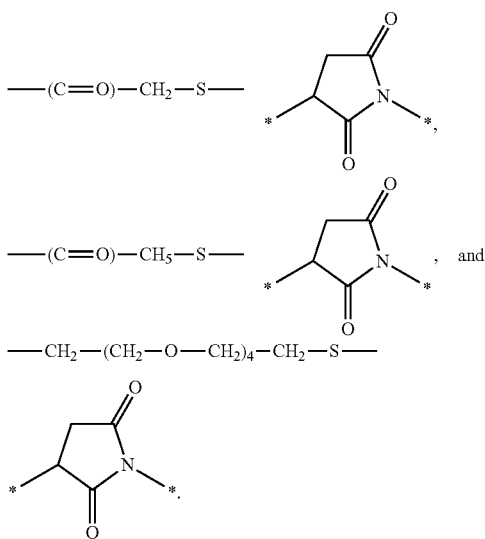

In some embodiments, L is or comprises an amino acid or a di-, tri-tetra- or oligopeptide. In some embodiments, L is selected from among alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, valine, and citrulline.

In any of the compounds (e.g. in any of Formula I, II and/or IV), linking element (L) can optionally be characterized as having a chain length of at least 2.8 Angstroms, 3, Angstroms, 4 Angstroms, 5 Angstroms, 10 Angstroms, 15 Angstroms, 18 Angstroms, 30 Angstroms, 40 Angstroms or 60 Angstroms. Optionally L has a length of no more than 100 Angstroms, optionally no more than 60 Angstroms. Optionally, L is characterized as having a length of between 2.8, 3, 4, 5, 10, 20 or 30 Angstroms and 60 Angstroms. Optionally, L is characterized as having a length of between 2.8 and 19 Angstroms, or between 4 and 19 Angstroms.

A compound may contain more than one L moiety. Any L' moiety can be defined in the same way as an L moiety. The L moieties may or may not be the same. The linking group L may be a water-soluble moiety or contain one or more water-soluble moieties, such that L contributes to the water solubility of a compound of Formula (I)-(VI). An L may also be a moiety or contain one or more moieties that reduce(s) aggregation, which may or may not be a moiety/moieties that also increase(s) the water solubility.

L may be for example a linear linker or a branched linker. In one aspect, the L moiety is branched, optionally further a dendritic structure, so that it can be connected to at least two, three, four or more V, Y or R moieties (or Z where applicable). Each V-Y moiety is however only attached once to an L moiety. Branching can occur at one or more branching atoms that may for example be carbon, nitrogen, silicon, or phosphorus.

When the lysine-based linker comprises branching in L, the number of branches in L that are connected to V and/or Y will generally be prepared so as to equal the total number of branches available for reaction. That is, in preparing the lysine-based linker, chemical conversion will preferably be carried to completion, thereby maintain the controlled stoichiometry offered by the site-specific TGase-mediated conjugation approach. Thus, preferably, when L is branched, compounds will be functionalized such that each L, V or Y is connected to a R or Z moiety, such that the components of the mixture of an antibodies (or the lysine-based linker during preparation) substantially all have the same r value. For example, it can be specified that 90%, 95%, 98% of the antibodies or the lysine-based linker have the same r value. In one embodiment, L is a linear linker. In another embodiment, L is a branched linker.

Any one of the L moieties disclosed herein can be utilized in Formula Ia, Ib, II, IVa, and IVb. Any one of the L moieties described herein can be used in combination with any of the $(C)_n$, X, V, Y, Z, R, M, z, q, and r groups described herein. Any one of the L' moieties disclosed herein can be utilized in Formula III. Any one of the L' moieties described herein can be used in combination with any of the R', V', Y', Z, z', q', and r' groups described herein.

Exemplary linkers of Formula Ia include but are not limited to:

Compound Ia-1

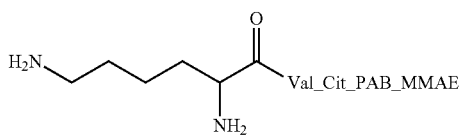

Compound Ia-2

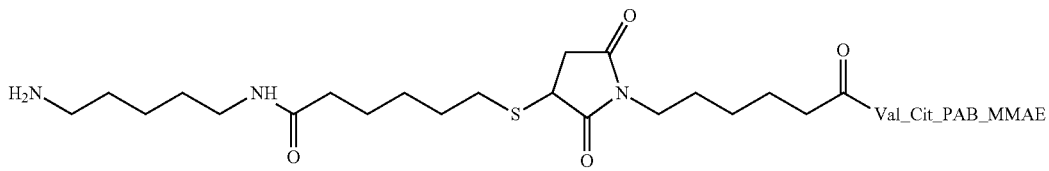

Compound Ia-3

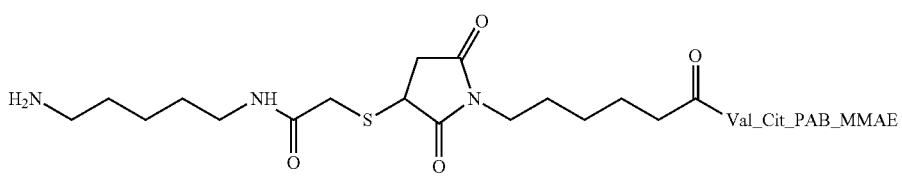

-continued
Compound Ia-4
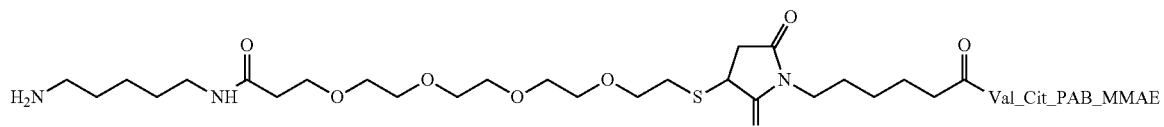
Compound Ia-5
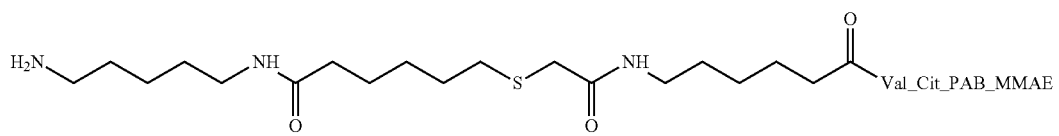
Compound Ia-6
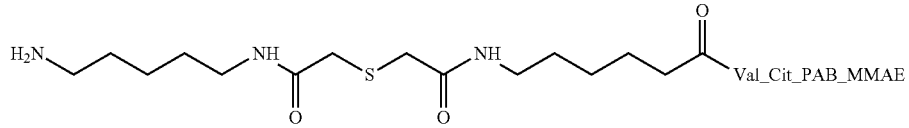
Compound Ia-7
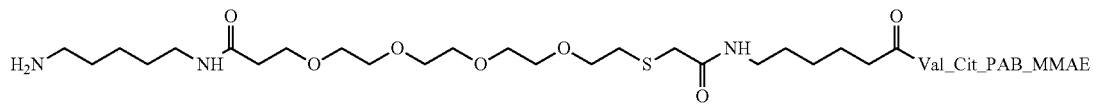
Compound Ia-8
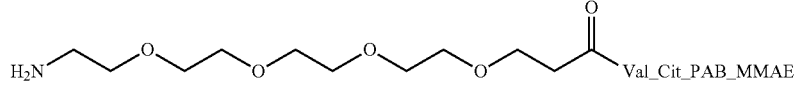
Compound Ia-9
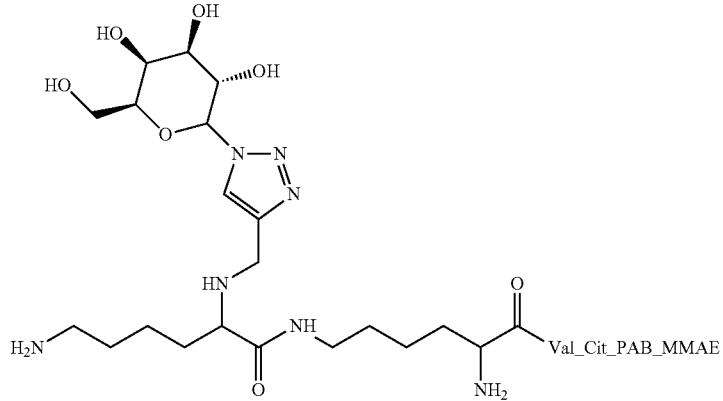
Compound Ia-10
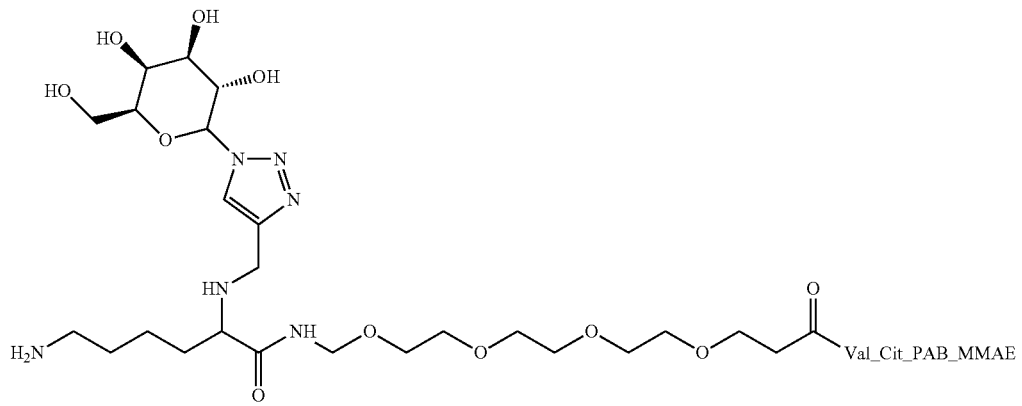

Compound Ia-11
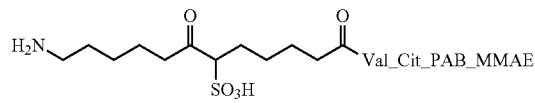
Compound Ia-12
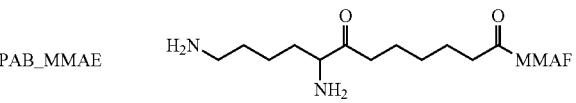
Compound Ia-13
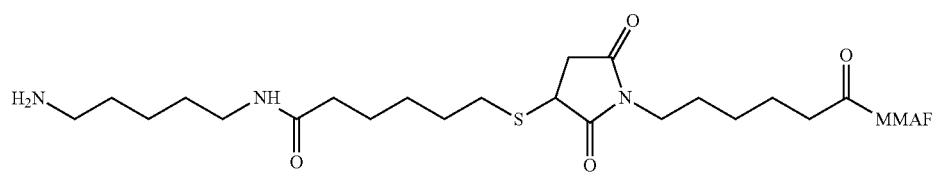
Compound Ia-14
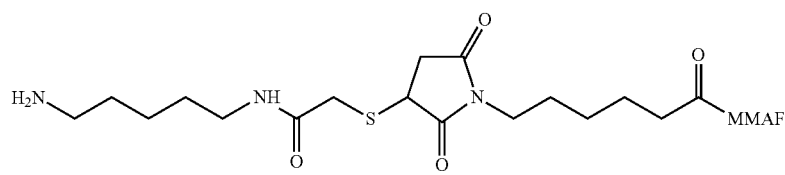
Compound Ia-15
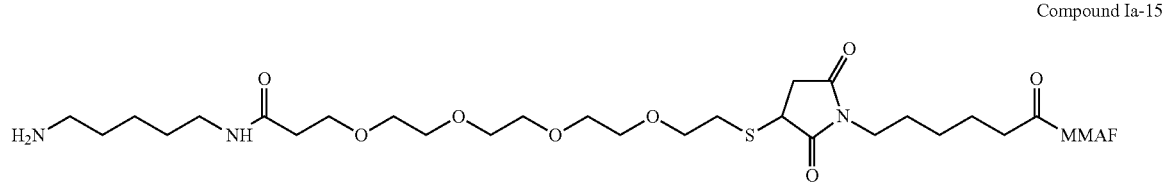
Compound Ia-16
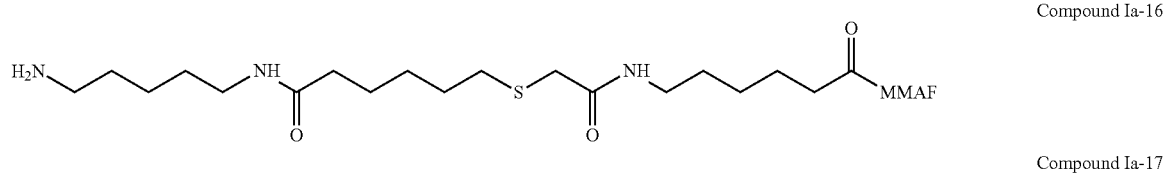
Compound Ia-17
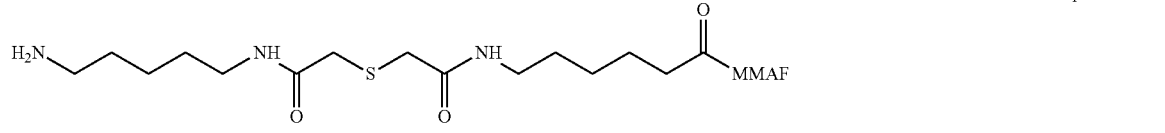
Compound Ia-18
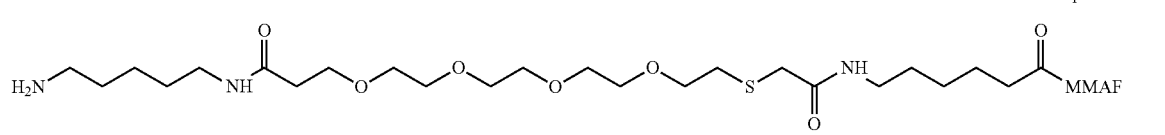
Compound Ia-19
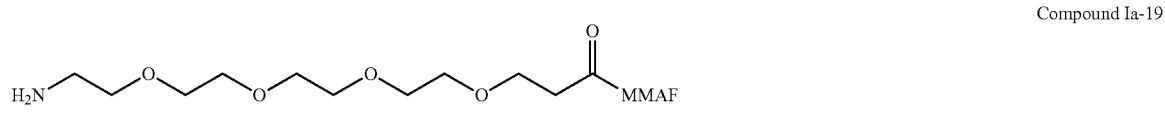
Compound Ia-20
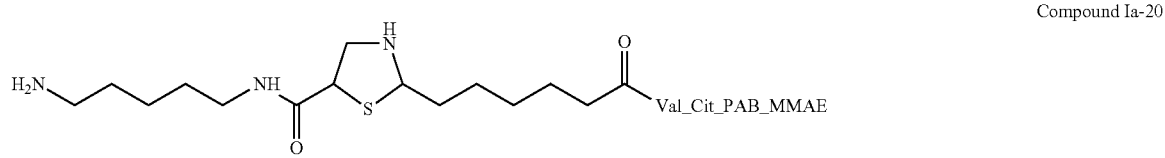
Compound Ia-21
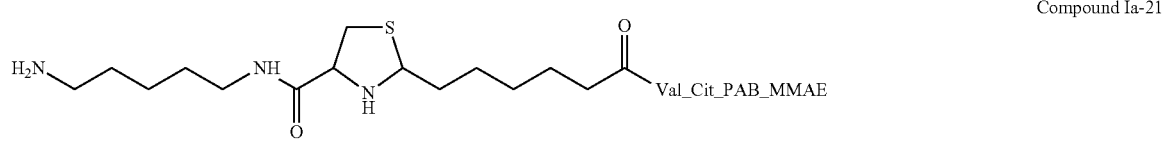
Compound Ia-22
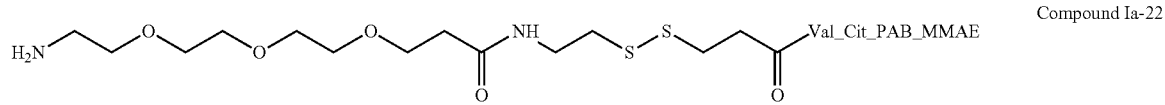

Compound Ia-23
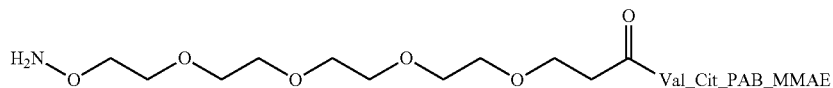
Exemplary linkers of Formula Ib include but are not limited to:
Compound Ib-1
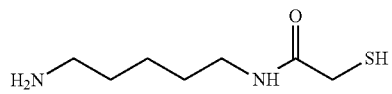
Compound Ib-2
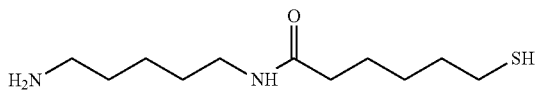
Compound Ib-3
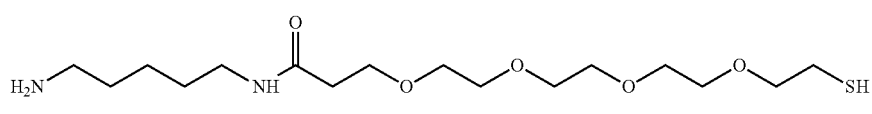
Compound Ib-4
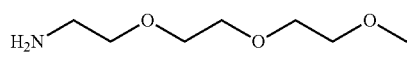
Compound Ib-5
Compound Ib-6
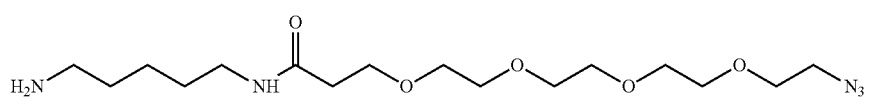
Compound Ib-7
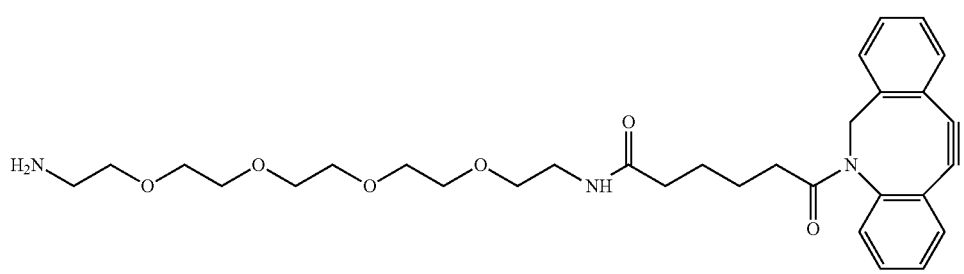
Compound Ib-8
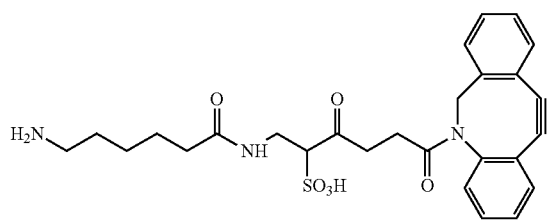
Compound Ib-9
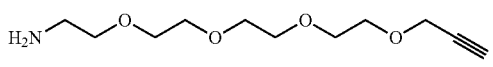
Compound Ib-10
Compound Ib-11
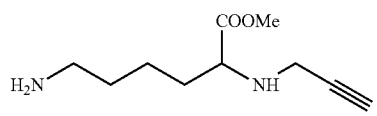
Compound Ib-12
Compound Ib-13
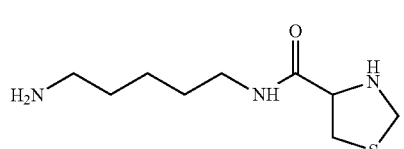
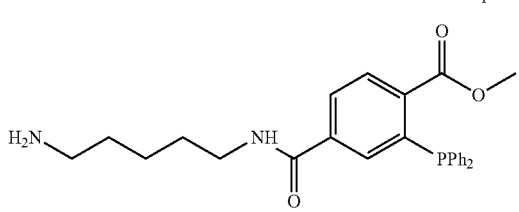

Compound Ib-14

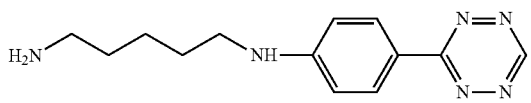

Compound Ib-15

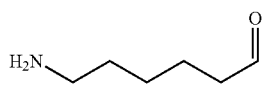

The Reactive Moiety R

R is a reactive moiety, for example a moiety comprising an unprotected or protected bioorthogonal-reaction compatible reactive group, for example an unprotected or protected thiol, epoxide, maleimide, haloacetamide, o-phoshenearomatic ester, azide, fulminate, sulfonate ester, alkyne, cyanide, amino-thiol, carbonyl, aldehyde, generally any group capable of oxime and hydrazine formation, 1,2,4,5-tetrazine, norbornene, other stained or otherwise electronically activated alkene, a substituted or unsubstituted cycloalkyne, generally any reactive groups which form via bioorthogonal cycloaddition reaction a 1,3- or 1,5-disubstituted triazole, any diene or strained alkene dienophile that can react via inverse electron demand Diels-Alder reaction, a protected or unprotected amine, a carboxylic acid, an aldehyde, or an oxyamine.

When more than one R group is present in a compound of the formula, the R groups will preferably be compatible such that no R group is a complementary reagent to any other R group. The L, V and/or Y groups of formulae I-IV can have r, q, and/or z sites of attachment for the respective V, Y, and R groups, where r and q represent the degree of branching or polymerization. The sites of attachment can comprise a bond or comprise a functional group selected from an alkene, alkyne, ether, thioether, ester, thioester, amine, amide, alkylamide, or other functional group readily generated by a condensation or addition reaction.

The reactive group of the linking reagent can for example chosen to undergo thio-maleimide (or haloacetamide) addition, Staudinger ligation, Huisgen 1,3-cycloaddition (click reaction), or Diels-Alder cycloaddition with a complementary reactive group attached to an agent comprising a therapeutic moiety, a diagnostic moiety, or any other moiety for a desired function.

Optionally, two or more compatible reactive groups can be attached to the linking reagent.

In one embodiment, the reactive group is a haloacetamide, (e.g. bromo-acetamide, iodo-acetamide, cloro-acetamide). Such reactive groups will be more stable in vivo (and in serum) compared with maleimide groups.

In one embodiment, the reactive group is a reagent capable of undergoing a "click" reaction (i.e., a Click Chemistry reagent or reactive group). For example a 1,3-dipole-functional compound can react with an alkyne in a cyclization reaction to form a heterocyclic compound, preferably in the substantial absence of added catalyst (e.g., Cu(I)). A variety compounds having at least one 1,3-dipole group attached thereto (having a three-atom pi-electron system containing 4 electrons delocalized over the three atoms) can be used to react with the alkynes disclosed herein. Exemplary 1,3-dipole groups include, but are not limited to, azides, nitrile oxides, nitrones, azoxy groups, and acyl diazo groups.

Examples include o-phosphenearomatic ester, an azide, a fulminate, an alkyne (including any strained cycloalkyne), a cyanide, an anthracene, a 1,2,4,5-tetrazine, or a norbornene (or other strained cycloalkene).

In one embodiment, R is a moiety having a terminal alkyne or azide; such moieties are described for example in U.S. Pat. No. 7,763,736, the disclosure of which is incorporated herein by reference. Suitable reaction conditions for use of copper (and other metal salt) as catalysts of click-reactions between terminal alkynes and azides are provided in U.S. Pat. No. 7,763,736.

In one embodiment, R is a substituted or unsubstituted cycloalkyne. Cycloalkynes, including heterocyclic compounds, will preferably be used in linking reagents in which an L group is present, preferably wherein L is an alkyl or heteroalkyl chain of 3-30, optionally 5-30 or 5-15 linear carbon atoms, optionally substituted at one or more atoms. Optionally, L is a $(CH_2-CH_2-O)_{1-24}$ group or a $(CH_2)_{x1}-(CH_2-O-CH_2)_{1-24}-(CH_2)_{x2}-$, wherein x1 and x2 are independently an integer selected among the range of 0 to 20. As shown herein, presence of an L group enables high TGase-mediated coupling when cycloalkynes are used.

Cycloalkynes, including specific compounds, are described for example in U.S. Pat. No. 7,807,619, the disclosure of which is incorporated herein by reference.

In some embodiments, a cycloalkyne may be a compound of Formula A:

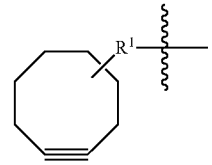

Formula A where:

$R^1$ is selected from a carbonyl, an alkyl ester, an aryl ester, a substituted aryl ester, an aldehyde, an amide, an aryl amide, an alkyl halide, a thioester, a sulfonyl ester, an alkyl ketone, an aryl ketone, a substituted aryl ketone, and a halosulfonyl;

$R^1$ can be at any position on the cyclooctyne group other than at the two carbons joined by the triple bond.

In some embodiments, the modified cycloalkyne is of Formula A, wherein one or more of the carbon atoms in the cyclooctyne ring, other than the two carbon atoms joined by a triple bond, is substituted with one or more electron-withdrawing groups, e.g., a halo (bromo, chloro, fluoro, iodo), a nitro group, a cyano group, a sulfone group, or a sulfonic acid group. Thus, e.g., in some embodiments, a subject modified cycloalkyne is of Formula B:

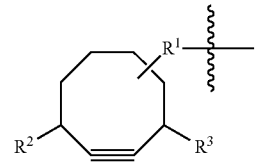

Formula B where:

each of $R^2$ and $R^3$ is independently: (a) H; (b) a halogen atom (e.g., bromo, chloro, fluoro, iodo); (c) —W—$(CH_2)_n$—Z (where: n is an integer from 1-4 (e.g., n=1, 2, 3, or 4); W, if present, is O, N, or S; and Z is nitro, cyano, sulfonic acid, or a halogen); (d) —$(CH_2)_n$—W—$(CH_2)_m$—$R^4$ (where: n and m are each independently 1 or 2; W is O, N, S, or sulfonyl; if W is O, N, or S, then $R^4$ is nitro, cyano, or halogen; and if W is sulfonyl, then $R^4$ is H); or (e) —$(CH_2)_n$—$R^4$ (where: n is an integer from 1-4 (e.g., n=1, 2, 3, or 4); and $R^4$ is nitro, cyano, sulfonic acid, or a halogen); and $R^1$ is selected from a carbonyl, an alkyl ester, an aryl ester, a substituted aryl ester, an aldehyde, an amide, an aryl amide, an alkyl halide, a thioester, a sulfonyl ester, an alkyl ketone, an aryl ketone, a substituted aryl ketone and a halosulfonyl. $R^1$ can be at any position on the cyclooctyne group other than at the two carbons linked by the triple bond.

In one embodiment, R is a substituted or unsubstituted heterocyclic strained alkyne. Cycloalkynes, including specific compounds, are described for example in U.S. Pat. No. 8,133,515, the disclosure of which is incorporated herein by reference. In one embodiment, the alkyne is of the Formula C:

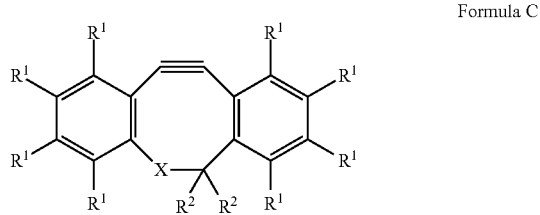

Formula C wherein:

each $R^1$ is independently selected from the group consisting of hydrogen, halogen, hydroxy, alkoxy, nitrate, nitrite, sulfate, and a $C_1$-$C_{10}$ alkyl or heteroalkyl;

each $R^2$ is independently selected from the group consisting of hydrogen, halogen, hydroxy, alkoxy, nitrate, nitrite, sulfate, and a $C_1$-$C_{10}$ organic group; X represents N—$R^3R^4$, NH—$R^4$, CH—N—$OR^4$, C—N—$NR^3R^4$, $CHOR_4$, or $CHNHR_4$; and each $R^3$ represents hydrogen or an organic group and $R^4$ represents linking moiety C (or $(C)_n$) of a linker. In one embodiment, R or R' is a DBCO (dibenzycyclooctyl) group below:

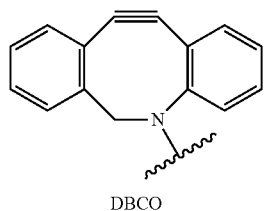 [SMILES: *N1Cc2ccccc2C#Cc2ccccc21 ; "DBCO"]

DBCO

Alkynes such as those described herein above can be reacted with at least one 1,3-dipole-functional compound (e.g., embodied as an R' moiety in a compound of Formula III) in a cyclization reaction to form a heterocyclic compound, preferably in the substantial absence of added catalyst (e.g., Cu(I)). A wide variety compounds having at least one 1,3-dipole group attached thereto (having a three-atom pi-electron system containing 4 electrons delocalized over the three atoms) can be used to react with the alkynes disclosed herein. Exemplary 1,3-dipole groups include, but are not limited to, azides, nitrile oxides, nitrones, azoxy groups, and acyl diazo groups.

The reactive moiety R is connected to L, or when present, V or Y, and is able to react with a suitable functional group (R') on a reaction partner, e.g. a complementary reagent of Formula III which undergoes a high conversion addition reaction when brought into contact with a reactive moiety R. When reactive moiety R is present in an antibody of Formula II, the reaction results in formation of an antibody of Formula IV. In this reaction, the moieties R and R' are transformed into the moiety (RR'). Any R' moiety can be defined in the same way as a R moiety, so long as R and R' are complementary when used in moieties that are to be reacted together.

A compound may contain more than one reactive moiety R. The R moieties may or may not be the same. Any one of the R moieties disclosed herein can be utilized in Formula Ib and II. Any one of the R moieties described herein can be used in combination with any of the $(C)_n$, X, L, V, Y, z, q, and r groups described herein. Any one of the R' moieties disclosed herein can be utilized in Formula III. Any one of the R' moieties described herein can be used in combination with any of the L', V', Y', Z, z', q', and r' groups described herein.

FIG. 1 shows reaction schemes for thio-maleimide additions, Staudinger ligations, and Diels-Alder cycloadditions, where reactive groups of linking reagents having a single reactive functionality combine with complementary reactive group attached to a therapeutic or diagnostic moiety.

Figure 2:
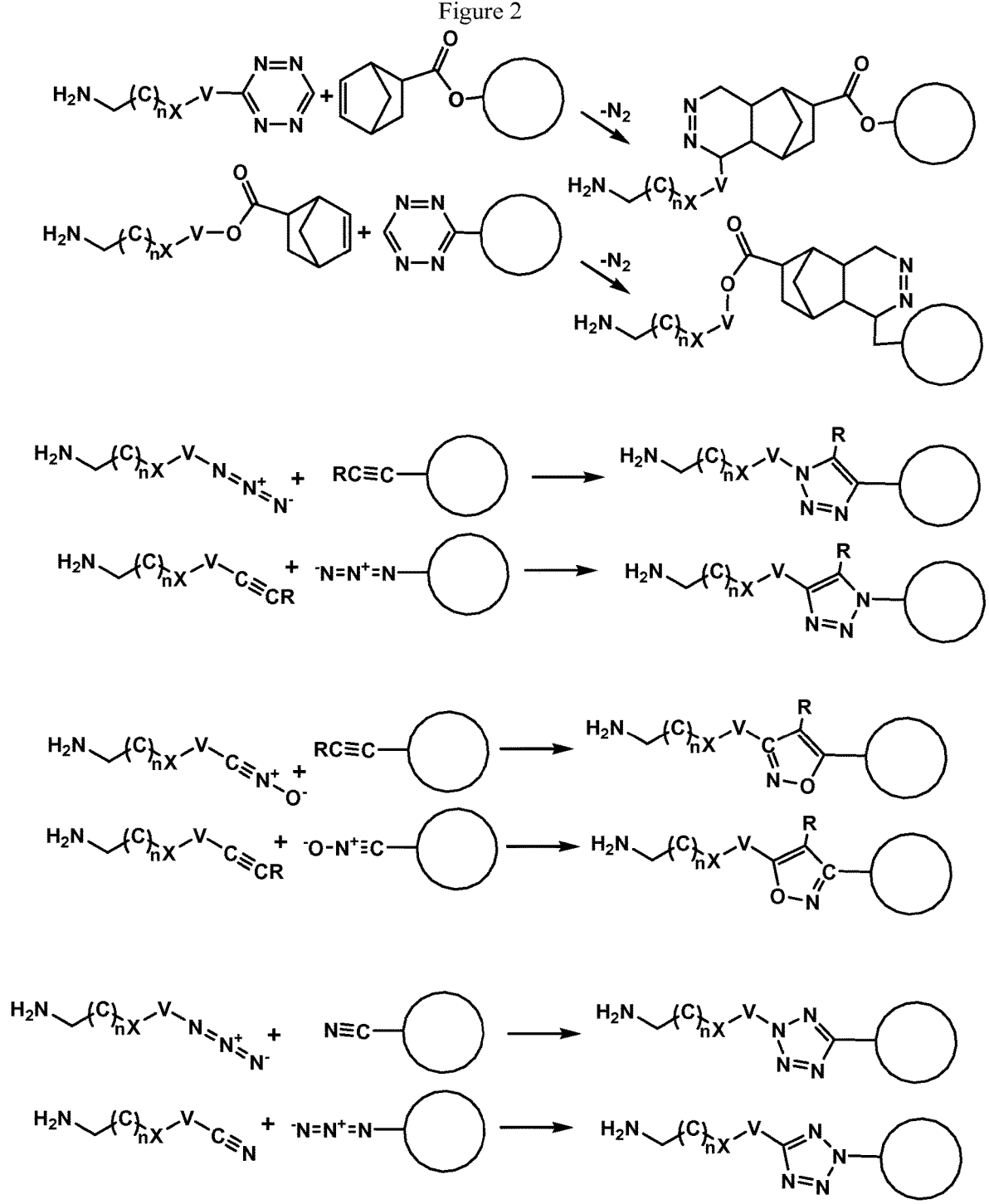
FIG. 2 shows reaction schemes for Diels-Alder cycloadditions and click reactions where the reactive groups of linking reagents combine with complementary reactive group attached to an agent including a therapeutic, diagnostic, or other moiety.

FIG. 2 shows reaction schemes for Diels-Alder cycloadditions and click reactions where the reactive groups of linking reagents combine with complementary reactive group attached to an agent including a therapeutic, diagnostic, or other moiety.

It should be understood that, although not illustrated in FIGS. 1 and 2, the $H_2NCH_2$ group of the linking reagent may have undergone reaction with the glutamine residue of an antibody prior to the high conversion addition reaction or that the aminomethylene may be in a protected state. Alternatively, in other embodiments, the $H_2NCH_2$ group of the linking reagent will not have undergone reaction with the glutamine residue of an antibody prior to the high conversion addition reaction or that the aminomethylene may be in a protected state; in this case the linking reagent and reaction partner can be used to conveniently form various combinations of linkers having different V, Y, and/or Z moieties that are ready to conjugate to an antibody.

Figure 3:
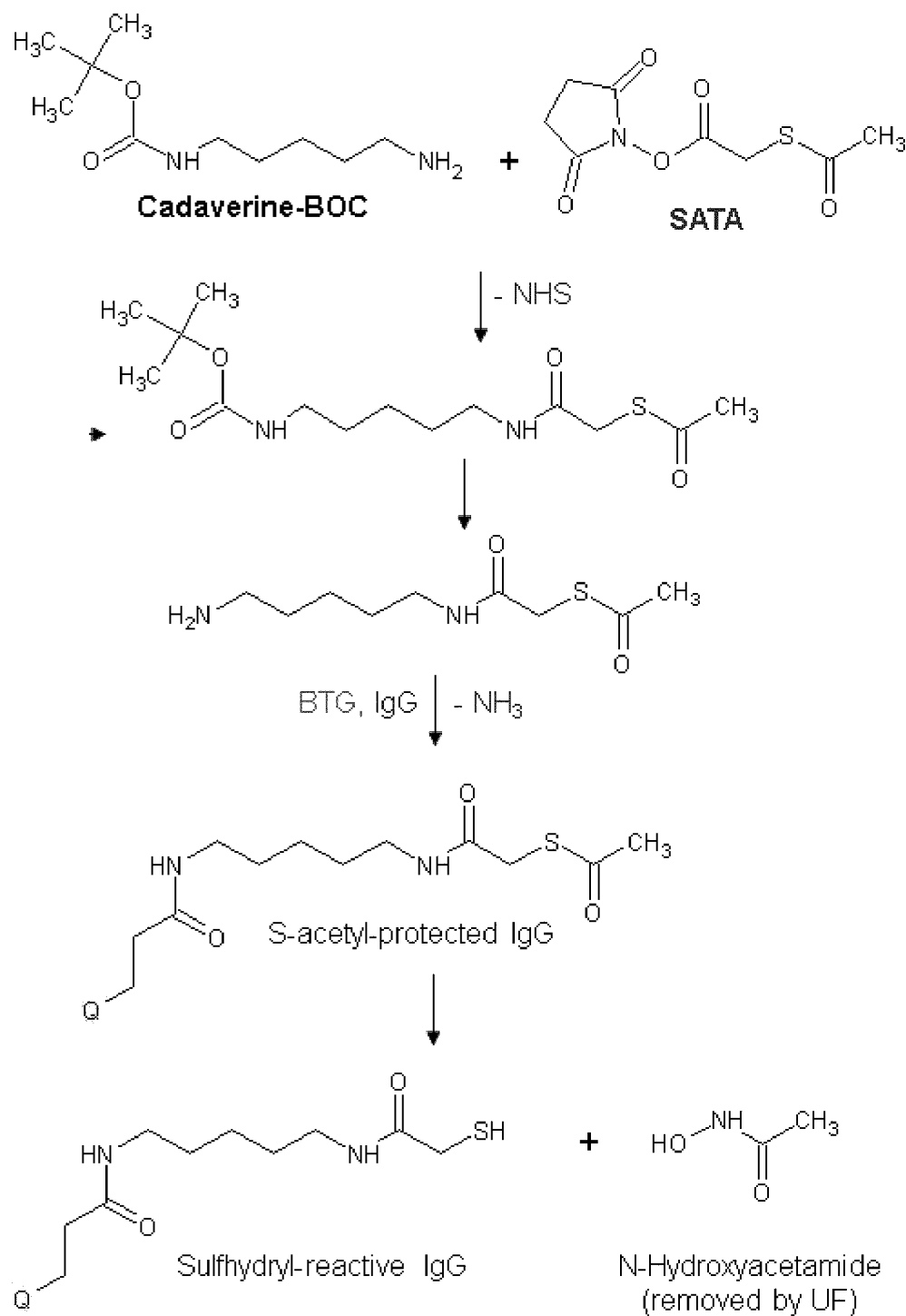
FIG. 3 shows the preparation of an exemplary linking reagent, and its conjugation with a protein, where: V and Y are absent, R is a thiol (sulfhydryl) reactive group that is ultimately generated from the S-acetyl protected thiol, $SC(O)CH_3$; r is 0; q is 0; z is 1; L is the two carbon comprising framework $C(O)CH_2$; X is NH; $(C)_n$ is $(CH_2)_5$; and G is transformed from the $(H_3C)_3COC(O)$ protecting group to H and ultimately to the amide upon conjugation of a glutamine residue of a protein.
Figure 4:
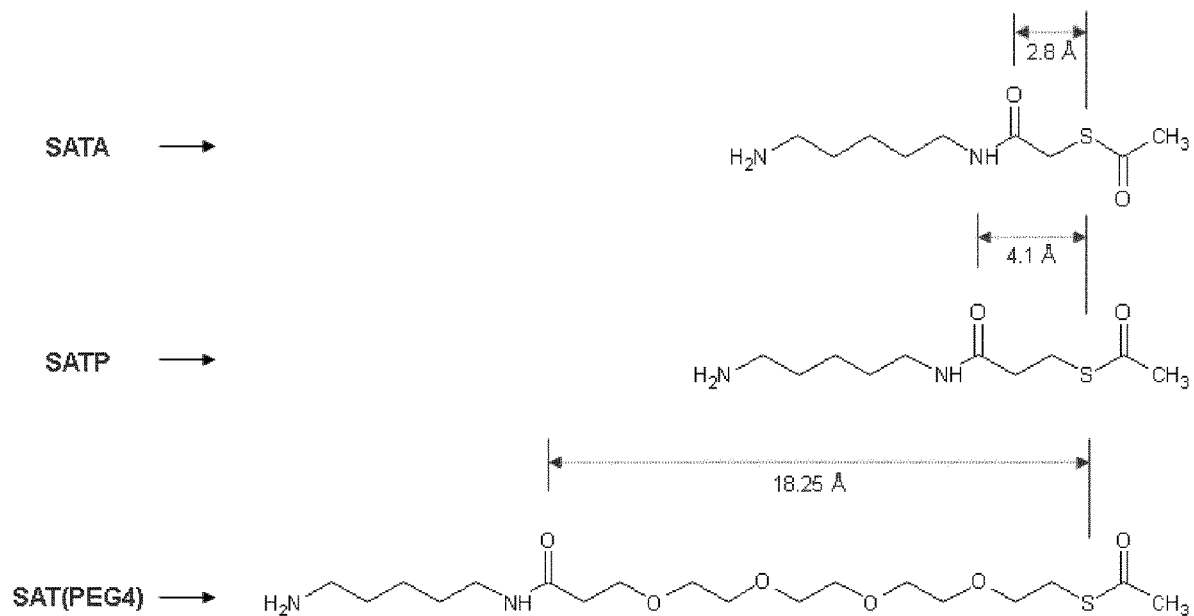
FIG. 4 illustrates the preparation of various exemplary linking reagents, with a single S-acetyl protected thiol reactive group that can be prepared from an N-succinimidyl-S-acetylthioester reagent.

The preparation of an exemplary linking reagent and its conjugation with a protein is illustrated in FIG. 3, where: V and Y are absent, R is a thiol (sulfhydryl) reactive group that is ultimately generated from the S-acetyl protected thiol, $SC(O)CH_3$, r is 1; q is 1; z is 1; L is the two carbon comprising framework $C(O)CH_2$; X is NH; $(C)_n$ is $(CH_2)_5$; and G is transformed from the $(H_3C)_3COC(O)$ protecting group to H and ultimately to the amide upon conjugation of a glutamine residue of a protein. FIG. 4 illustrates the preparation of various exemplary linking reagents, with a single S-acetyl protected thiol reactive group that can be prepared from an N-succinimidyl-S-acetylthioester reagent. In addition to S-acetyl, other S-protecting groups can be employed, including p-hydroxyphenylacyl, 2-quinoline, or Hqm and Hgm groups that can be deprotected by the addition of hydrazine.

Figure 5:
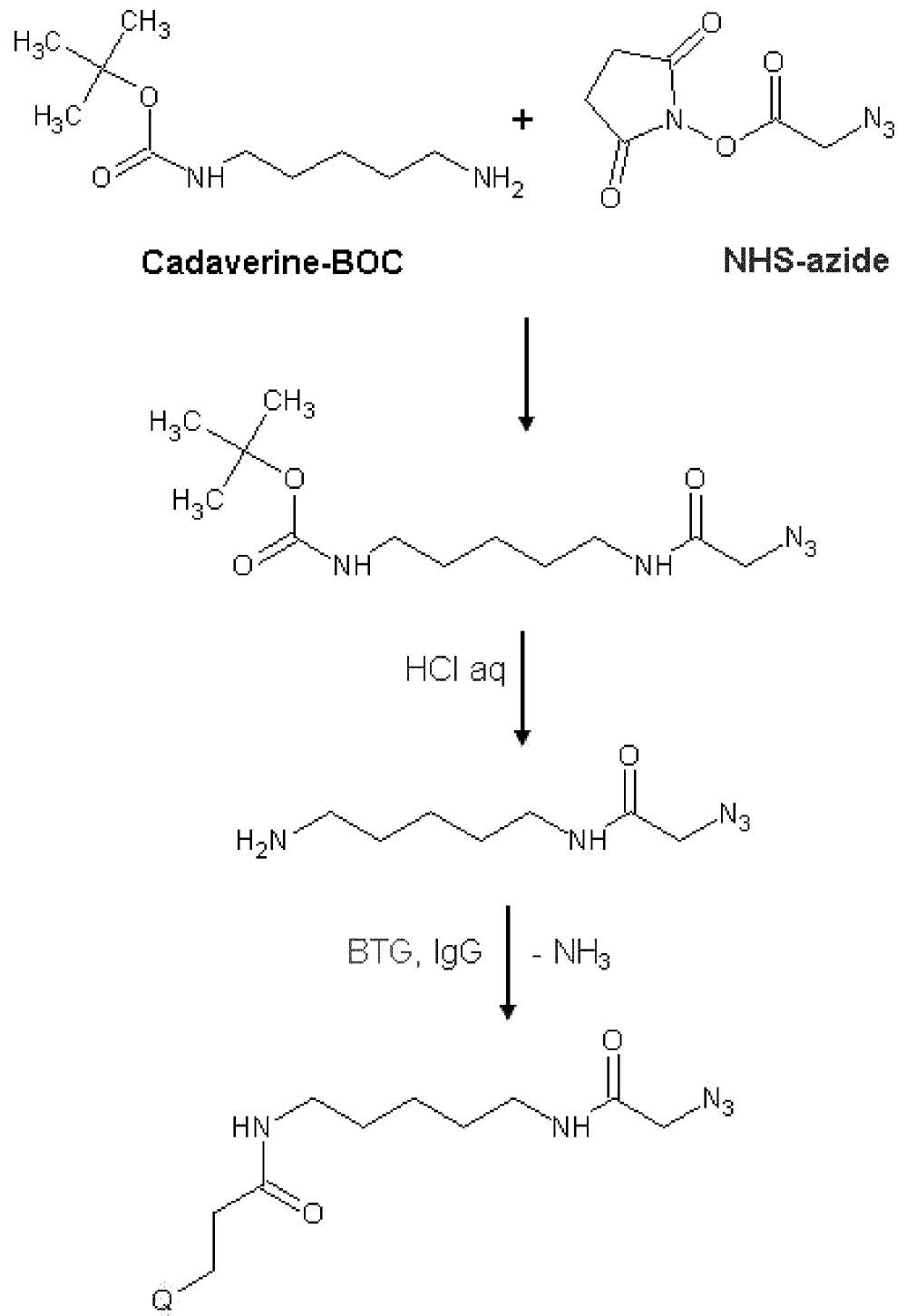
FIG. 5 illustrates the preparation of an exemplary linking reagent, and its conjugation with a protein, where: V and Y are absent, R is an azide reactive group; r is 0; q is 0; z is 1; L is the two carbon comprising framework $C(O)CH_2$; X is NH; $(C)_n$ is $(CH_2)_5$; and G is transformed from the $(H_3C)_3COC(O)$ protecting group to H and ultimately to the amide upon conjugation of a glutamine residue of a protein.
Figure 6:
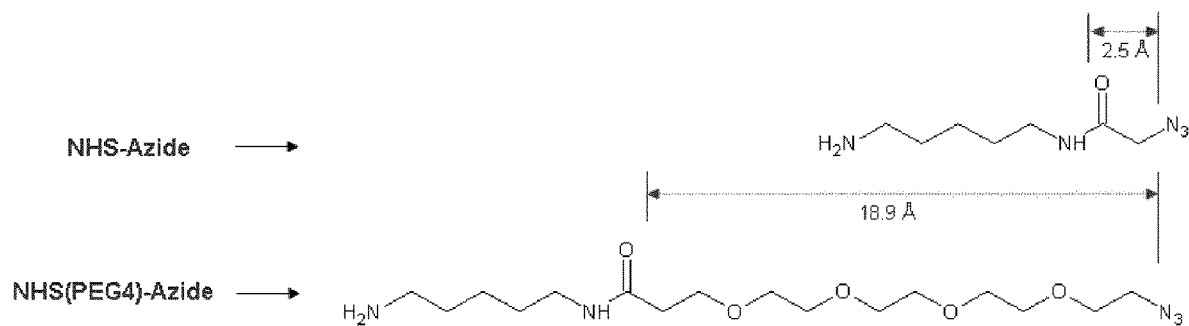
FIG. 6 illustrates the preparation of various exemplary linking reagents, with a single azide reactive group that can be prepared from an N-succinimidyl-azide reagent.

FIG. 5 illustrates the preparation of an exemplary linking reagent, and its conjugation with a protein, where: V and Y are absent, R is an azide reactive group; r is 1; q is 1; z is 1; L is the two carbon comprising framework C(O)CH$_2$; X is NH; (C)$_n$ is (CH$_2$)$_5$; and G is transformed from the (H$_3$C)$_3$COC(O) protecting group to H and ultimately to the amide upon conjugation of a glutamine residue of a protein. FIG. 6 illustrates the preparation of various exemplary linking reagents, with a single azide reactive group that can be prepared from an N-succinimidyl-azide reagent.

Figure 7:
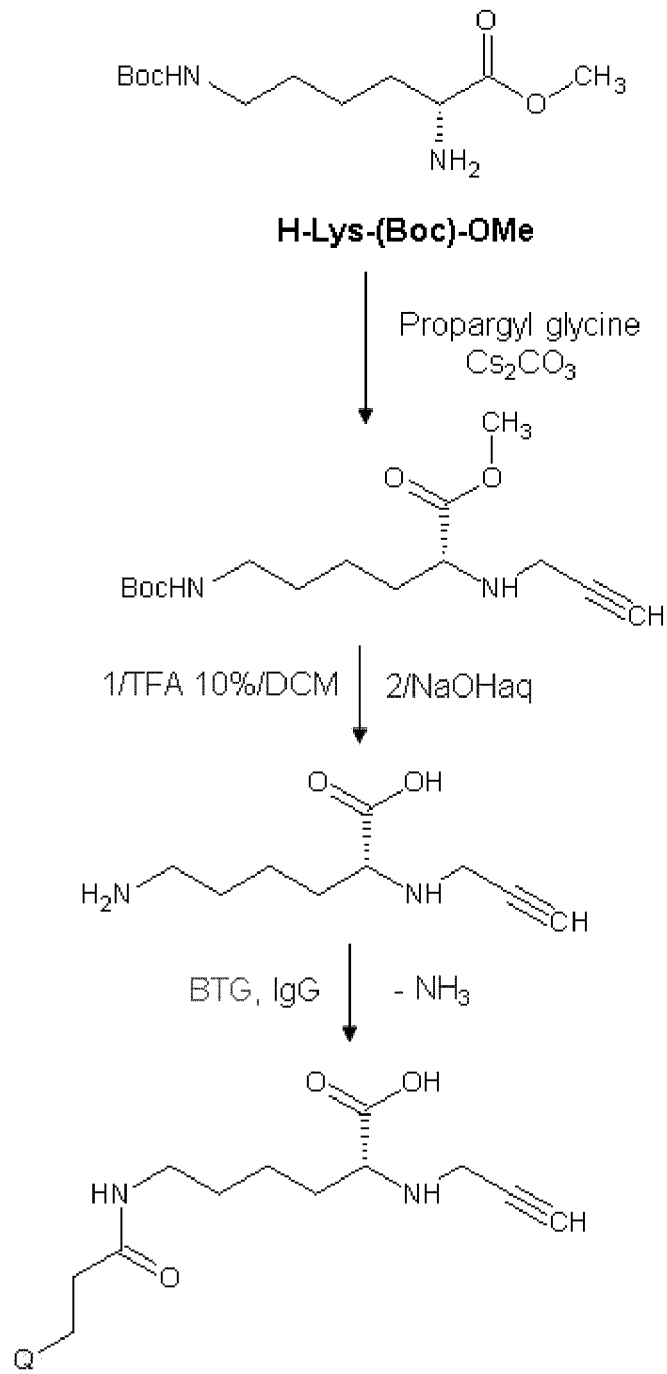
FIG. 7 depicts the preparation of an exemplary linking reagent, and its conjugation with a protein, where: V and Y are absent, R is an alkyne reactive group; r is 0; q is 0; z is 1; L is a one carbon comprising framework $CH_2$; X is NH; $(C)_n$ is $(CH_2)_4CH(CO_2H)$; and G is transformed from the $(H_3C)_3COC(O)$ protecting group to H and ultimately to the amide upon conjugation of a glutamine residue of a protein.
Figure 8:
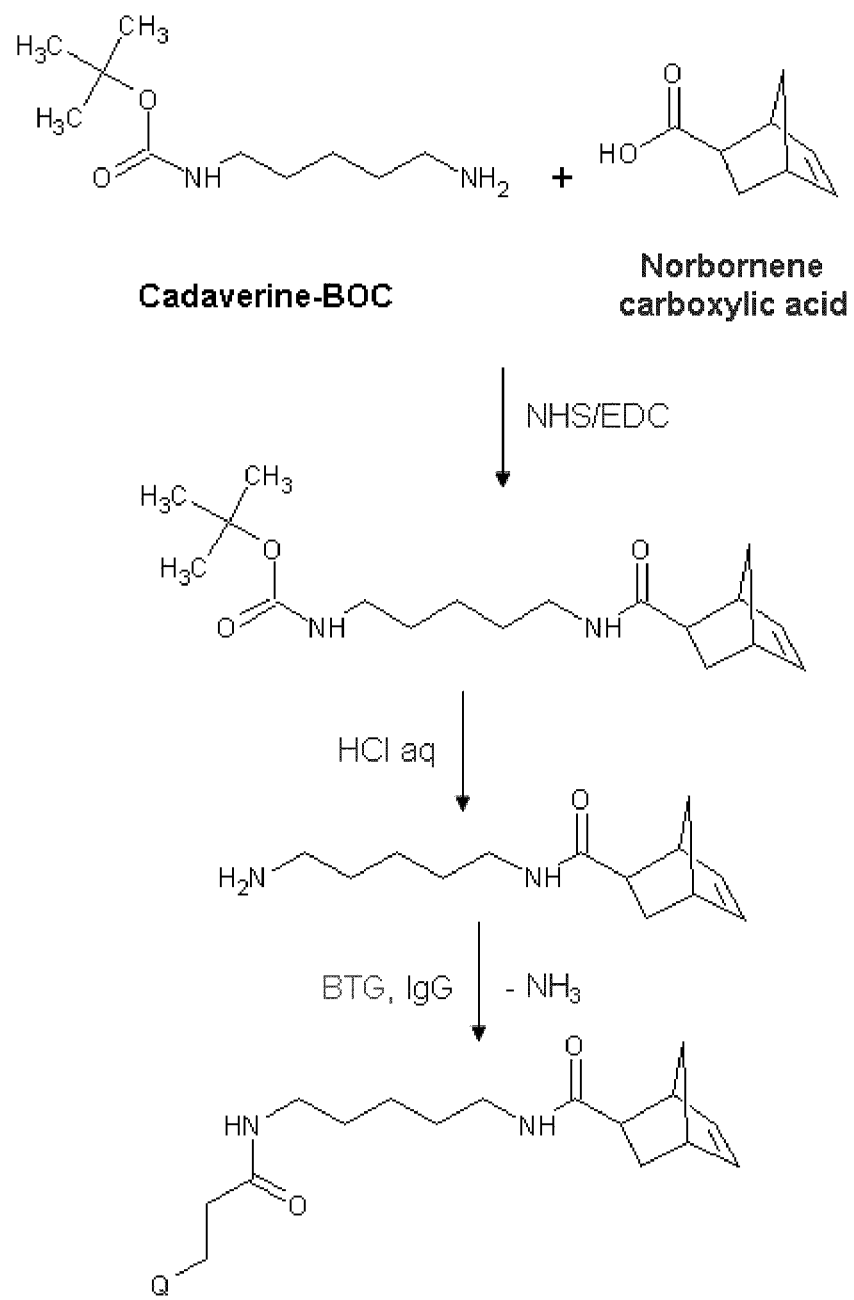
FIG. 8 shows the preparation of an exemplary linking reagent, and its conjugation with a protein, where: R is a norbornene reactive group; r is 0; q is 0; z is 1; L is the one carbon comprising framework $C(O)$; X is NH; $(C)_n$ is $(CH_2)_4CH(CO_2H)$; and G is transformed from the $(H_3C)_3COC(O)$ protecting group to H and ultimately to the amide upon conjugation of a glutamine residue of a protein.
Figure 9:
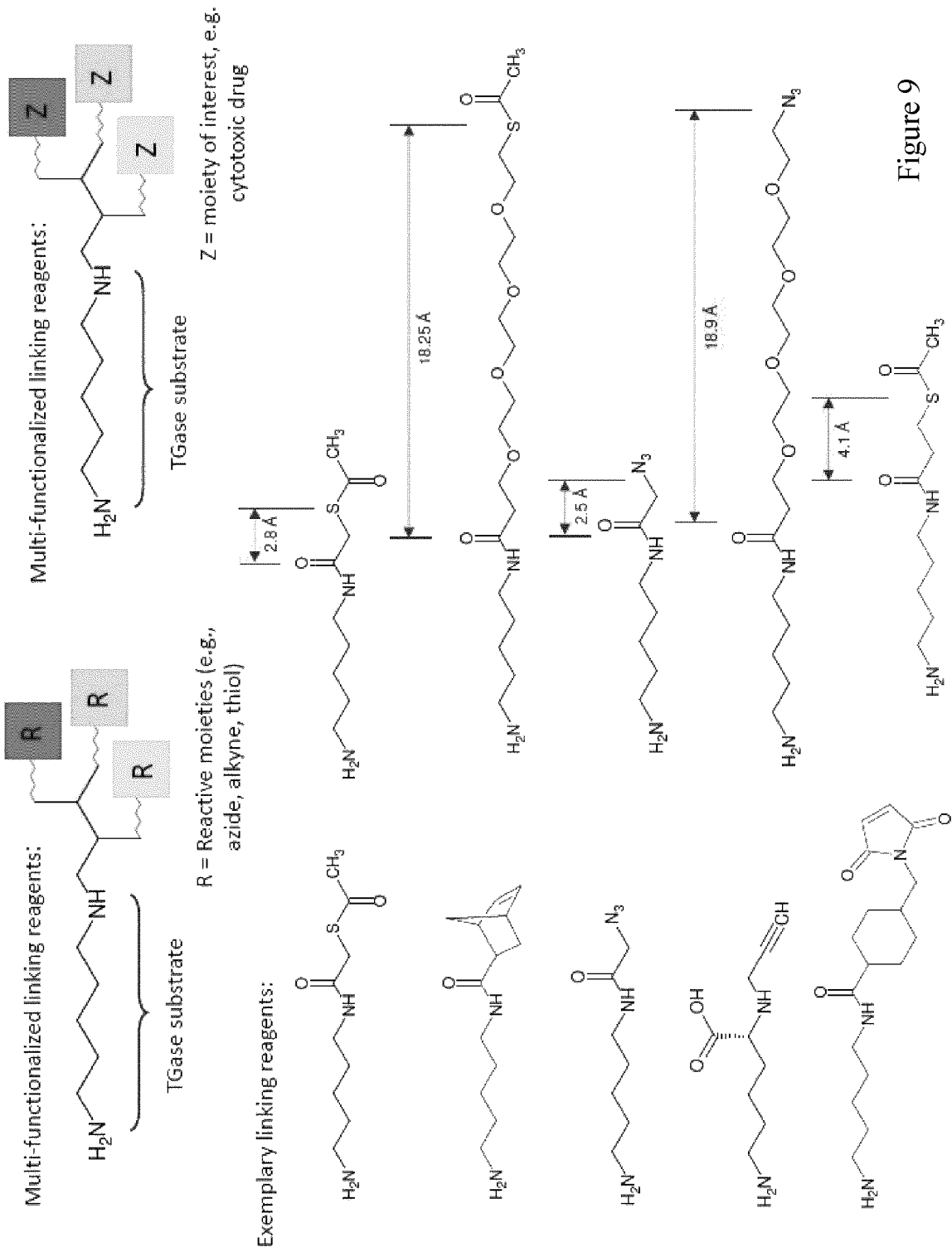
FIG. 9 shows various examples of linking reagents.
Figure 10A:
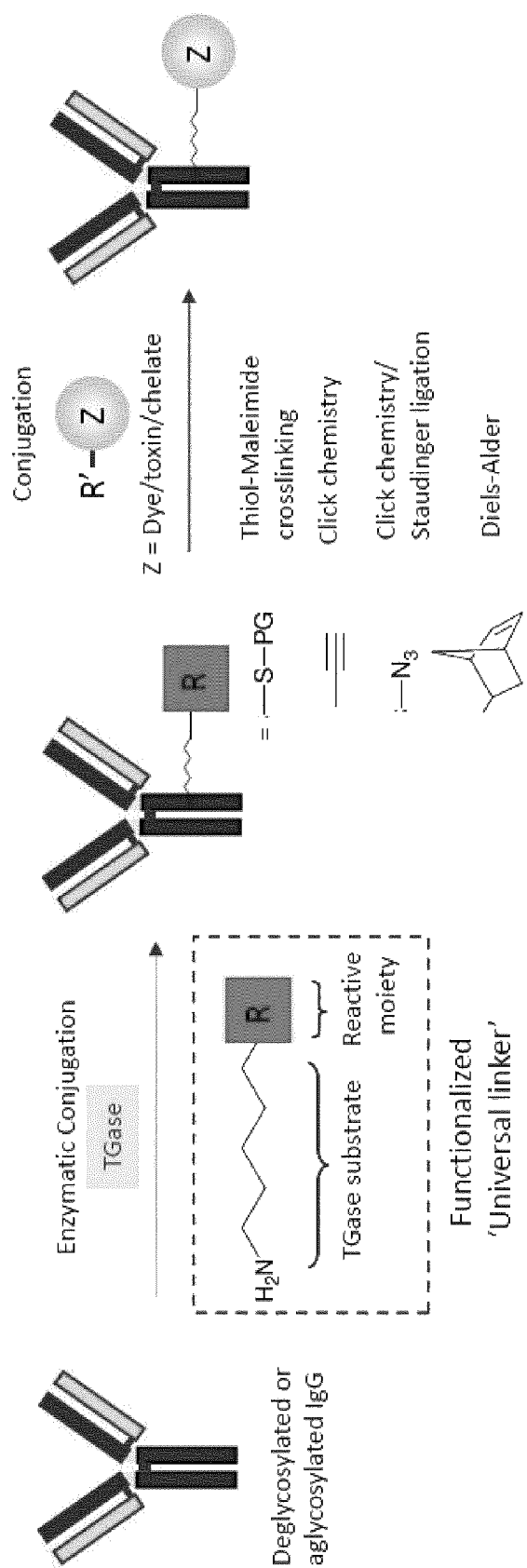
FIGS. 10A and 10B show a general scheme for preparing conjugated antibodies.
Figure 10B:
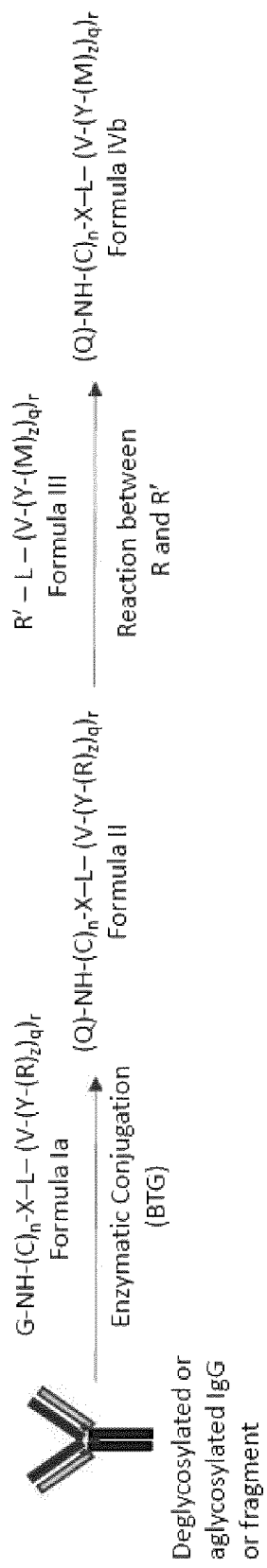
Figure 10B:
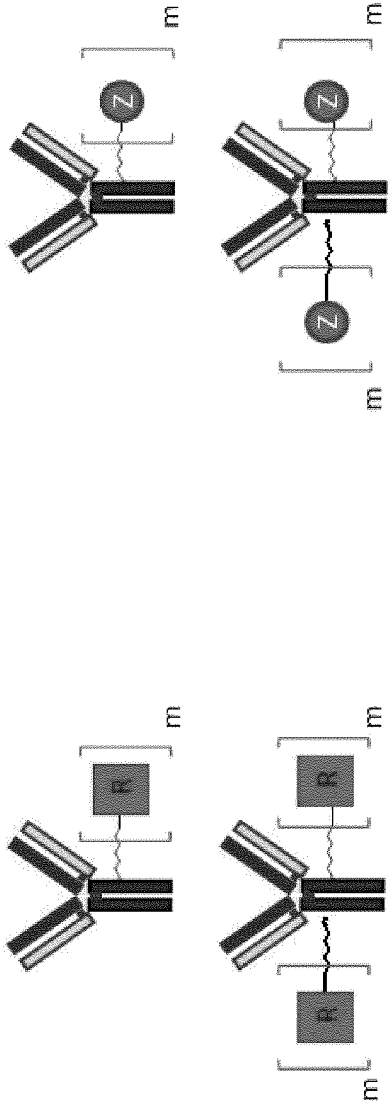

FIG. 7 depicts the preparation of an exemplary linking reagent, and its conjugation with a protein, where: V and Y are absent, R is an alkyne reactive group; r is 1; q is 1; z is 1; L is a one carbon comprising framework CH$_2$; X is NH; (C)$_n$ is (CH$_2$)$_4$CH(CO$_2$H); and G is transformed from the (H$_3$C)$_3$COC(O) protecting group to H and ultimately to the amide upon conjugation of a glutamine residue of a protein. FIG. 8 shows the preparation of an exemplary linking reagent, and its conjugation with a protein, where: R is a norbornene reactive group; r is 1; q is 1; z is 1; L is the one carbon comprising framework C(O); X is NH; (C)$_n$ is (CH$_2$)$_4$CH(CO$_2$H); and G is transformed from the (H$_3$C)$_3$COC(O) protecting group to H and ultimately to the amide upon conjugation of a glutamine residue of a protein.

The selective and very high conversion addition reaction that can be carried out with the linking reagents can be uncatalyzed or catalyzed reactions. For example, the 2+4 Diels-Alder cycloadditions, thio-maleimide (or haloacetamide) additions, and Staudinger ligations can be carried out without a catalyst. Other very high conversion addition reactions, for example any of the click reactions, can be catalyzed with metal salts, such as Cu, Ru, Ni, Pd, and Pt salts.

The linking group (RR') in M of compounds of Formula IV represents the remainder of R when the reactive moiety R of Formula II has reacted with a reactive moiety R' in a compound of Formula III. This group (RR') then links the moiety Z (e.g. comprised in the compound of formula IV) with L, V or Y. The group that remains may be a bond.

The V Moiety

The V moiety may be incorporated in the lysine-based linker (e.g. connected to L, optionally through Y). However, the V moiety may instead or in addition be incorporated in a compound comprising a moiety-of-interest Z (e.g. a compound R'—V—Y—Z of formula III) that will be reacted with an antibody conjugated with a lysine-based linker to form an antibody conjugated to the moiety-of-interest Z. Any V' moiety can be defined in the same way as a V moiety.

In the compounds, the V moiety is a group that is either non-cleavable or conditionally cleavable, optionally after prior conditional transformation. In the latter case, it is designed to be transformed and/or cleaved from Y, or Z when Y is absent, by a chemical, photochemical, physical, biological, or enzymatic process, e.g. in certain conditions. This condition may for example comprise bringing a compound in an aqueous environment, which leads to hydrolysis of V, or bringing a compound in an environment that contains an enzyme that recognizes and cleaves V, or bringing a compound under reducing conditions, which leads to reduction of V, or bringing a compound in contact with radiation, e g, UV light, which leads to transformation and/or cleavage, or bringing a compound of in contact with heat, which leads to transformation and/or cleavage, or bringing a compound under reduced pressure or bringing a compound under elevated or high pressure, which leads to transformation and/or cleavage. This condition may further be met after administrating a compound to an animal, e.g., a mammal: the condition may be met when the compound localizes to for example a specific organ, tissue, cell, sub-cellular target, or microbial target, for example by the presence of internal factors (e.g., target-specific enzymes or hypoxia) or application of external factors (e g., radiation, magnetic fields) or the condition may already be met directly upon administration (e.g., enzymes). In general, transformation of V will directly or indirectly lead to cleavage of V from Y, or Z when Y is absent. It may occur that two or more separate transformations and/or cleavages, requiring the same or different conditions, are required in order to cleave V completely from Y or Z. In this way, increased selectivity may be obtained. A compound may contain more than one V moiety. These V moieties may or may not be the same and may or may not require the same conditions for transformation and/or cleavage.

V may comprise for example a carbon comprising framework of 1 to 200 atoms, optionally a carbon comprising framework of at least 10 atoms, e.g. 10 to 100 atoms or 20 to 100 atoms, substituted at one or more atoms, optionally wherein the carbon comprising framework is a linear hydrocarbon or comprises a cyclic group, a symmetrically or asymmetrically branched hydrocarbon, monosaccharide, disaccharide, linear or branched oligosaccharide (asymmetrically branched or symmetrically branched), other natural linear or branched oligomers (asymmetrically branched or symmetrically branched), an amino acid, a di-, tri-, tetra-, or oligopeptide, or more generally any dimer, trimer, or higher oligomer (linear, asymmetrically branched or symmetrically branched) resulting from any chain-growth or step-growth polymerization process.

Generally, V may be any straight, branched and/or cyclic C$_{2-30}$ alkyl, C$_{2-30}$ alkenyl, C$_{2-30}$ alkynyl, C$_{2-30}$ heteroalkyl, C$_{2-30}$ heteroalkenyl, C$_{2-30}$ heteroalkynyl, optionally wherein one or more homocyclic aromatic compound radical or heterocyclic compound radical may be inserted; notably, any straight or branched C$_{2-5}$ alkyl, C$_{5-10}$ alkyl, C$_{11-20}$ alkyl, —O—C$_{1-5}$ alkyl, —O—C$_{5-10}$ alkyl, —O—C$_{11-20}$ alkyl, or (CH$_2$—CH$_2$—O—)$_{1-24}$ or (CH$_2$)$_{x1}$—(CH$_2$—O—CH$_2$)$_{1-24}$—(CH$_2$)$_{x2}$-group, wherein x1 and x2 are independently an integer selected among the range of 0 to 20, an amino acid, an oligopeptide, glycan, sulfate, phosphate, or carboxylate. Optionally, V may be or absent. In some embodiments, V is a C$_{2-6}$ alkyl group.

In one aspect, a compound is used to target one or more therapeutic and/or diagnostic moieties Z to target cells. In this instance, V may for example contain a substrate molecule that is cleaved by an enzyme present in the vicinity of the target cells or inside the target cells, for example tumor cells. V can for example contain a substrate that is cleaved by an enzyme present at elevated levels in the vicinity of or inside the target cells as compared to other parts of the body, or by an enzyme that is present only in the vicinity of or inside the target cells.

If target cell specificity is achieved solely based upon the selective transformation and/or cleavage of V at the target site, the condition (eventually) causing the cleavage should preferably, at least to a certain degree, be target cell-specific, whereas the presence of another target-specific moiety in the compound, for instance when the ABD recognizes an antigen present on a target cell with a degree of specificity, reduces or takes away this requirement. For example, when an antibody causes specific internalization into a target cell, an enzyme also present in other cells may transform and/or cleave V. In one embodiment, transformation and/or cleavage of V occurs intracellularly. In another embodiment, transformation and/or cleavage of V occurs extracellularly.

In one embodiment, the V moiety is a conditionally cleavable moiety.

In one embodiment, V contains a di-, tri-, tetra-, or oligopeptide which consists of an amino acid sequence recognized by a protease, for example plasmin, a cathepsin, cathepsin B, prostate-specific antigen (PSA), urokinase-type plasminogen activator (u-PA), or a member of the family of matrix metalloproteinases, present in the vicinity of or inside the target cells, for example tumor cells. In one embodiment provided is a conjugate wherein V is a dipeptide, tripeptide, tetrapeptide, or oligopeptide moiety comprised of natural L amino acids, unnatural D amino acids, or synthetic amino acids, or a peptidomimetic, or any combination thereof. In one embodiment, V is a peptide. In another embodiment, V is a dipeptide. In another embodiment, V is a tripeptide. In another embodiment, V is a tetrapeptide. In yet another embodiment, V is a peptidomimetic.

In one embodiment, V contains a substrate for an enzyme.

In another embodiment, V contains a beta-glucuronide that is recognized by beta-glucuronidase present in the vicinity of or inside tumor cells.

In one embodiment, V contains a substrate for an extracellular enzyme. In another embodiment, V contains a substrate for an intracellular enzyme.

In yet another embodiment, V contains a substrate for a lysosomal enzyme.

In yet another embodiment, V contains a substrate for the serine protease plasmin.

In yet another embodiment, V contains a substrate for one or more of the cathepsins, for example cathepsin B. When V is cleaved extracellularly, the one or more Z moieties may be released extracellularly. This may provide the advantage that these Z moieties are not only able to affect or detect the cell(s) directly surrounding the site of activation, but also cells somewhat further away from the site of activation due to diffusion (bystander effect).

In one embodiment V comprises a tripeptide. The tripeptide may be linked via its C-terminus to Y. In one embodiment, the C-terminal amino acid residue of the tripeptide is selected from arginine, citrulline, and lysine, the middle amino acid residue of the tripeptide is selected from alanine, valine, leucine, isoleucine, methionine, phenylalanine, cyclohexylglycine, tryptophan and proline, and the N-terminal ammo acid residue of the tripeptide is selected from any natural or unnatural amino acid.

In another embodiment V comprises a dipeptide. The dipeptide may be linked via its C-terminus to Y. In one embodiment, the C-terminal amino acid residue of the dipeptide is selected from alanine, arginine, citrulline, and lysine, and the N-terminal amino acid residue of the dipeptide is selected from any natural or unnatural amino acid. In one embodiment, V is selected from phenylalanine-lysine and valine-citrulline.

An example of a linker comprising a lysine residue as $(C)_n$ moiety and a valine-citrulline as the (V) moiety is shown below:

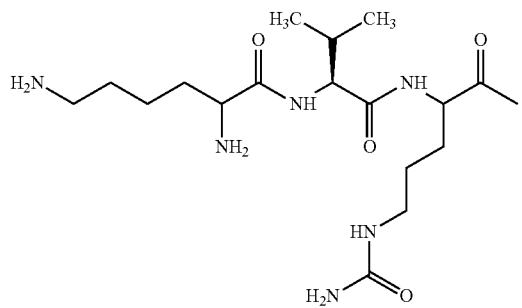 [SMILES: CC(=O)C(CCCNC(N)=O)NC(=O)[C@@H](NC(=O)C(N)CCCCN)C(C)C]

Optionally, the di-, tri-, tetra, or oligopeptide(s) comprise or consist or amino acids with non-negatively charged side chains (amino acids other than aspartic acid or glutamic acid). Optionally, the di-, tri-, tetra, or oligopeptide(s) comprise or consist or amino acids selected from: amino acids with positively charged side chains, amino acids with polar uncharged side chains, and amino acids with hydrophobic side chains.

In another aspect, a compound is used to improve the pharmacokinetic properties of Z. V may in this case for example be or contain a group that is cleaved by ubiquitous enzymes, e.g., esterases that are present in the circulation, by pH-controlled intramolecular cyclization, or by acid-catalyzed, base-catalyzed, or non-catalyzed hydrolysis, or V may for example be or contain a disulfide. V may therefore, optionally together with the connecting atom of L and/or Y (or Z if Y is absent), for example form a carbonate, carbamate, urea, ester, amide, imine, hydrazone, oxime, disulfide, acetal, or ketal group. It is understood that V can also be or contain such a moiety and/or be transformed and/or cleaved in the same or a similar way when a compound is used for other purposes than solely improving the pharmacokinetic properties of Z.

When the compounds are used for other purposes, e.g., an ex vivo diagnostic assay, V may be or contain any of the moieties mentioned above and transformation and/or cleavage of V may occur by any one of the processes mentioned above or by any other functional transformation or cleavage process known to a person skilled in the art. For example, in a diagnostic assay, V may be cleaved or transformed by an enzyme, by reduction, or below, above, or at a certain pH.

When V is conditionally cleavable, the compounds are designed to eventually release at least one Z after cleavage and optional prior transformation of V. Release of Z from a compound via another mechanism is however not excluded.

In any embodiment, V may contain a blocking group to prevent premature transformation and/or cleavage of V before the condition is met under which V is designed to be transformed and/or cleaved.

In another aspect, V is a moiety that is non-cleavable. This means that V cannot be cleaved from Y, or Z when Y is absent, under the conditions the compound containing such a V moiety is designed to be applied, meaning that Z cannot be released in this way. Release of Z from a compound via another mechanism is however not excluded. When V is a non-cleavable moiety, Y may optionally be absent. A non-cleavable V moiety may be any moiety that cannot be cleaved, or that can be cleaved only very slowly, under the conditions the compound containing such a V moiety is designed to be applied, e.g. in vivo or in vitro. For example, when applied in vivo, V will not or only very slowly be cleaved by enzymes present in the in vivo model used or by hydrolysis or as a consequence of other biological processes that may occur in said model. Such V may therefore, optionally together with the connecting atom of L and/or Z, for example, be a carbonyl group, an amide group, an urea group, an ester group, a carbonate group, a carbamate group, or an optionally substituted methyleneoxy or methyleneamino group V may be preferred to be non-cleavable when it is not required that the one or more moieties Z are released. This may for example be the case when Z does not require to become released before it can exert its therapeutic or diagnostic properties.

In one embodiment V is connected to L via a functional group in the side chain of one of the natural or unnatural amino acids. In another embodiment, the N-terminal amino acid of V is connected via its alpha amino group to L.

Any one of the V moieties disclosed herein can be utilized in Formula Ia, Ib, II, IVa and IVb. Any one of the V moieties described herein can be used in combination with any of the $(C)_n$, X, L, R, Y, Z, M, z, q, and r groups described herein. Any one of the V' moieties disclosed herein can be utilized in Formula III. Any one of the V' moieties described herein can be used in combination with any of the R', V', Y', Z, z', q', and r' groups described herein.

The Spacer System Y

The spacer system Y, when present, links V and optionally L to one or more moieties R, and following reaction with a compound of Formula III, a moiety-of-interest Z. In one embodiment, Y is absent. In another embodiment, Y is a self-elimination spacer system. A spacer system Y may be incorporated in a compound to for example improve the properties of Z or the compound in general, to provide suitable coupling chemistries, or to create space between V and Z. Any Y' moiety can be defined in the same way as a Y moiety.

Spacer system Y may comprise for example a carbon comprising framework of 1 to 200 atoms, optionally a carbon comprising framework of at least 10 atoms, e.g. 10 to 100 atoms or 20 to 100 atoms, substituted at one or more atoms, optionally wherein the carbon comprising framework is a linear hydrocarbon or comprises a cyclic group, a symmetrically or asymmetrically branched hydrocarbon, monosaccharide, disaccharide, linear or branched oligosaccharide (asymmetrically branched or symmetrically branched), other natural linear or branched oligomers (asymmetrically branched or symmetrically branched), an amino acid, a di-, tri-, tetra-, or oligopeptide, or more generally any dimer, trimer, or higher oligomer (linear, asymmetrically branched or symmetrically branched) resulting from any chain-growth or step-growth polymerization process.

Y may be any straight, branched and/or cyclic $C_{2-30}$ alkyl, $C_{2-30}$ alkenyl, $C_{2-30}$ alkynyl, $C_{2-30}$ heteroalkyl, $C_{2-30}$ heteroalkenyl, $C_{2-30}$ heteroalkynyl, optionally wherein one or more homocyclic aromatic compound radical or heterocyclic compound radical may be inserted; notably, any straight or branched $C_{2-5}$ alkyl, $C_{5-10}$ alkyl, $C_{11-20}$ alkyl, —O—$C_{1-5}$ alkyl, —O—$C_{5-10}$ alkyl, —O—$C_{11-20}$ alkyl, or $(CH_2$—$CH_2$—$O$—$)_{1-24}$ or $(CH_2)_{x1}$—$(CH_2$—$O$—$CH_2)_{1-24}$—$(CH_2)_{x2}$— group, wherein x1 and x2 are independently an integer selected among the range of 0 to 20, an amino acid, an oligopeptide, glycan, sulfate, phosphate, or carboxylate. Optionally, Y is absent. In some embodiments, Y is a $C_{2-6}$ alkyl group.

A compound may contain more than one spacer system Y. These moieties Y may or may not be the same. In some embodiments the spacer system Y is a self-elimination spacer that is connected to one or more other self-elimination spacers via a direct bond. Herein, a single self-elimination spacer may also be referred to as a spacer system. A spacer system may be branched or unbranched and contain one or more attachment sites for Z as well as V. Self-elimination spacers that are able to release only a single moiety are called 'single release spacers'. Self-elimination spacers that are able to release two or more moieties are called 'multiple release spacers'. Spacers, may be either branched or unbranched and self-eliminating through a 1,2+2n-elimination (n>/=1), referred to as "electronic cascade spacers". Spacers may eliminate through a cyclization process under formation of a cyclic urea derivative, referred to as "ω-amino aminocarbonyl cyclization spacers".

The spacer system Y may self-eliminating or non-self-eliminating. A "self-eliminating" spacer unit allows for release of the drug moiety without a separate hydrolysis step. When a self-eliminating spacer is used, after cleavage or transformation of V, the side of Y linked to V becomes unblocked, which results in eventual release of one or more moieties Z. The self-elimination spacer systems may for example be those described in WO 02/083180 and WO 2004/043493, which are incorporated herein by reference in their entirety, as well as other self-elimination spacers known to a person skilled in the art. In certain embodiments, a spacer unit of a linker comprises a p-aminobenzyl unit. In one such embodiment, a p-aminobenzyl alcohol is attached to an amino acid unit via an amide bond, and a carbamate, methylcarbamate, or carbonate is made between the benzyl alcohol and a cytotoxic agent. In one embodiment, the spacer unit is p-aminobenzyloxycarbonyl (PAB). Examples of self-eliminating spacer units further include, but are not limited to, aromatic compounds that are electronically similar to p-aminobenzyl alcohol (see, e.g. US 2005/0256030 A1), such as 2-aminoimidazol-5-methanoi derivatives (Hay et al. (1999) Bioorg. Med. Chem. Lett. 9:2237) and ortho- or para-aminobenzylacetals. Spacers can be used mat undergo cyclization upon amide bond hydrolysis, such as substituted and unsubstituted 4-aminobutyric acid amides (Rodrigues et al. Chemistry Biology, 1995, 2, 223) and 2-aminophenyl-propionic acid amides (Amsberry, et al., J. Org. Chem., 1990, 55. 5867). Elimination of amine-containing drugs that are substituted at the a-position of glycine (Kingsbury, et al., J. Med. Chem., 1984, 27, 1447) are also examples of self-immolative spacers.

A "non-self-eliminating" spacer unit is one in which part or all of the spacer unit remains bound to the moiety Z upon enzymatic (e.g., proteolytic) cleavage of the antibody-moiety-of-interest conjugate. Examples of non-self-eliminating spacer units include, but are not limited to, a glycine spacer unit and a glycine-glycine spacer unit. Other combinations of peptidic spacers susceptible to sequence-specific enzymatic cleavage are also contemplated. For example, enzymatic cleavage of an antibody-moiety-of-interest conjugate containing a glycine-glycine spacer unit by a tumor-cell associated protease would result in release of a glycine-glycine-drug moiety from the remainder of the antibody-moiety-of-interest conjugate. In one such embodiment, the glycine-glycine-drug moiety is then subjected to a separate hydrolysis step in the tumor cell, thus cleaving the glycine-glycine spacer unit from the drug moiety.

In a compound, a spacer system Y may be connected to more than one V moiety. In this case, transformation and/or cleavage of one of these V moieties may trigger the release of one or more Z moieties. When V moieties that are transformed or cleaved under different conditions are connected to the same Y, release of one or more Z moieties may occur when a compound is brought under one of several different conditions.

Any one of the Y moieties disclosed herein can be utilized in Formula Ia, Ib, II, IVa and IVb, V or VI. Any one of the Y moieties described herein can be used in combination with any of the $(C)_n$, X, L, V, Y, R, Z, M, z, q, and r groups described herein. Any one of the Y' moieties disclosed herein can be utilized in Formula III. Any one of the Y' moieties described herein can be used in combination with any of the R', L', V', Z, z', q', and r' groups described herein.

Conjugation of Lysine-Based Linkers to an Antibody

Enzymes of the TG-family catalyze covalent protein crosslinking by forming proteinase resistant isopeptide bonds between a lysine donor residue of one protein and an acceptor glutamine residue of another protein and is accompanied by the release of ammonia. The catalytic mechanism of transglutaminases has been proposed as follows. After the glutamine-containing first substrate (acceptor residue) binds to the enzyme, it forms a γ-glutamylthioester with the cysteine residue in the active center of TGase, known as the acylenzyme intermediate, accompanied by the release of ammonia. The second substrate (donor or K-substrate) then binds to the acylenzyme intermediate and attacks the thioester bond. The product (two proteins crosslinked by an Nε(γ-glutamyl)lysine isopeptide bridge) is formed and released. This re-establishes the active-centre Cys residue of the enzyme in its original form and allows it to participate in another cycle of catalysis. The formation of the covalent acylenzyme intermediate is thought to be the rate-limiting step in these reactions. The catalytic triad of many transglutaminases is papain-like, containing Cys-His-Asp (where His is histidine and Asp is aspartic acid) and, crucially, a tryptophan (Trp) residue located 36 residues away from the active-centre Cys. In contrast, bacterial TG isolated from *Streptoverticillium* sp (vide supra) has an atypical catalytic triad and shows no sequence homology with the papain-like catalytic triad of other TGases.

TGases display strict specificity in recognition of glutamine protein substrates. However, TGases display broad specificity for recognition of the acyl-acceptor amine group, which can either be the ε-amino group of peptidyl lysine or a low-molecular mass primary amine (frequently a polyamine) (see, e.g. Folk, et al. (1980) J. Biol. Chem. 255, 3695-3700. For example, in addition to lysine, the small lysine-mimicking primary amine 5-pentylamine (cadaverin) and variants or fragments thereof can efficiently bind to the acylenzyme intermediate, and a pseudo-isopeptide bond with the glutamine-containing protein is formed. See, e.g., Lorand, L. et al. (1979) Biochemistry 18, 1756-1765 (1979); Murthy, S. N. et al. (1994). J. Biol. Chem. 269, 22907-22911 (1994); Murthy, P. et al. (2009) Biochemistry (2009).

Bacterial, archaeal and eukaryotic TGases have been characterized and differ in several ways from mammalian TGases (Lorand, L. & Graham, R. M. (2003) Nat. Rev. Mol. Cell Biol. 4, 140-156). BTG and more generally microbial TGases (EC 2.3.2.13, protein-glutamine-γ-glutamyltransferase) such as *Streptomyces mobaraensis* are calcium-independent and have an amino acid sequence of) very different from those of mammalian TGs (Ando et al. (1989) Agric. Biol. Chem. 53, 2613-2617). BTG is furthermore much smaller (37.8 kDa versus 76.6 kDa for guinea pig liver TG). Additionally, BTG shows broader substrate specificity for the amine acceptor glutamine substrates in proteins than do mammalian TGases. These characteristics, together with a higher reaction rate, low cost of production, and a decreased tendency to catalyze deamidation make BTG a preferred enzyme for use in industrial applications.

When an acceptor glutamine is located within the CH2 domain, the antibodies that are to be conjugated to the lysine-based linker will preferably be free of N-linked glycosylation. Full-length wild-type IgG antibodies naturally comprise N-linked glycosylation at residue 297 of the heavy chain which interferes and prevents with TGase-mediated conjugation onto glutamine residues in the CH2 domain. Consequently, antibodies may be deglycosylated. Deglycosylation can be carried out as described herein or according to any suitable method. For example, antibody (1 mg) in PBS buffer (0.1 mol/L NaCl and 0.05 mol/L sodium phosphate buffer, pH 7.4) are incubated with 100 units (0.2 µL) of N-glycosidase F (PNGase F) from *Flavobacterium meningosepticum* (New England BioLabs, Ipswich, UK) at 37° C. overnight. The enzyme is then removed by centrifugation-dialysis (Vivaspin MWCO 50 kDa, Vivascience, Winkel, Switzerland). The product can be analyzed by LC/MS.

In one embodiment, the product is analyzed for drug loading (e.g. number of conjugates per antibody. Such methods can be used to determine the mean number of conjugates per antibody (e.g., the mean DAR) as well as the distribution of number of conjugates per antibody in a composition, i.e. the percentage of total antibody with any given level of drug loading or DAR. One technique adapted to such determination and more generally drug loading is hydrophobic interaction chromatography (HIC), HIC can be carried out as described for example in Hamblett et al. (2004) Cancer Res. 10: 7063-7070; Wakankar et al. (2011) mAbs 3(2): 161-172; and Lyon et al (2012) Methods in Enzymology, Vol. 502: 123-138, the disclosure of which are incorporated herein by reference.

Examples of useful TGases include microbial transglutaminases, such as e.g. from *Streptomyces mobaraense, Streptomyces cinnamoneum* and *Streptomyces griseocarneum* fall disclosed in U.S. Pat. No. 5,156,956, which is incorporated herein by reference), and *Streptomyces lavendulae* (disclosed in U.S. Pat. No. 5,252,469, which is incorporated herein by reference) and *Streptomyces ladakanum* (JP2003199569, which is incorporated herein by reference). It should be noted that members of the former genus *Streptoverticillium* are now included in the genus *Streptomyces* (Kaempfer, J Gen Microbiol, 137, 1831-1892, 1991). Other useful microbial transglutaminases have been isolated from *Bacillus subtilis* (disclosed in U.S. Pat. No. 5,731,183, which is incorporated herein by reference) and from various Myxomycetes. Other examples of useful microbial transglutaminases are those disclosed in WO 96/06931 (e.g. transglutaminase from *Bacilus lydicus*) and WO 96/22366, both of which are incorporated herein by reference. Useful non-microbial transglutaminases include guinea-pig liver transglutaminase, and transglutaminases from various marine sources like the flat fish Pagrus major (disclosed in EP-0555649, which is incorporated herein by reference), and the Japanese oyster *Crassostrea gigas* (disclosed in U.S. Pat. No. 5,736,356, which is incorporated herein by reference). A preferred TGase is bacterial transglutaminase (BTG) (see, e.g. EC 2.3.2.13, protein-glutamine-γ-glutamyltransferase). In a more preferred embodiment, the TGase is from *S. mobaraense*. In another embodiment, the TGase is a mutant TGase having at least 80% sequence homology with native TGase. A preferred example is recombinant bacterial transglutaminase derived from *streptomyces mobaraensis* (available from Zedira, Darmstadt, Germany).

The TGase-catalyzed reaction can be carried out under mild conditions, from several hours to a day (e.g. overnight). Recombinant BTG (EC 2.3.2.13) from *streptomyces mobaraensis* (Zedira, Darmstadt, Germany) can be used at a concentration of between 1 and 20 U/mL, preferably between 6 U/mL and 20 U/mL. The lysine-based linker substrates are reacted with antibody (1 mg/mL) at ligand concentrations between 400 and 600 mol/L, providing a 60 to 90-fold excess of the substrates over the antibody, or optionally at lower excess of substrates, e.g. 1- to 20-fold, or 10-20 fold. The reactions are performed in potassium-free phosphate buffered saline (PBS; pH 8) at 37° C. After 4 h to several days (depending on the antibody and the ligand), steady-state conditions are achieved. Excess ligand and enzyme are then removed using centrifugation-dialysis (Vivaspin MWCO 50 kDa, Vivascience, Winkel, Switzerland). Reactions are monitored by LC/MS. Higher amounts of TGase can be used as a function of different lysine-derivatives and substrates.

An acceptor glutamine present on an antibody (e.g. part of the antibody's primary structure will, under suitable conditions, be recognized by a TGase and covalently bound to a lysine-based linker (e.g., compound of Formula I). The result is an antibody of Formula II or IVa (the acceptor glutamine is functionalized with the compound of Formula Ib or Ia respectively).

Reaction Partners Comprising a Moiety-of-Interest Z and Reactive Group R'

Once a lysine-based linker (e.g., compound of Formula I) comprising a reactive moiety R is conjugated to an antibody (e.g., resulting in an antibody of Formula II) the antibody can be reacted with a compound comprising a moiety Z and a reactive group R', thereby forming an antibody-moiety-of-interest conjugate. In some embodiments, the conjugated antibody (e.g. the antibody of Formula II) is subjected to a deprotection step to provide an unprotected reactive group (R) and the antibody is then reacted with a compound comprising a reaction partner R'.

As discussed, this reaction step may be carried out in solution or while antibody is bound to a solid support. For example, when a lysine-based linker comprising a reactive moiety R is conjugated by a TGase while the antibody is immobilized on a solid support, the compound comprising a moiety Z and a reactive group R' can be introduced to the same solid support (e.g. following a washing step) such that the antibody is then reacted with the compound comprising a reaction partner R' while immobilized on the solid support. There is therefore no need to elute the antibody prior to the reaction with compound comprising a moiety Z and a reactive group R'.

In another variation, when a lysine-based linker comprising a reactive moiety R is conjugated by a TGase while the antibody is in solution, the reaction mixture from the TGase mediated reaction that comprises both antibody and TGase can be introduced directly to a solid support so as to immobilize the antibody but not TGase to the solid support. The compound comprising a moiety Z and a reactive group R' can then be introduced to a solid support such that the antibody is then reacted with the compound comprising a reaction partner R' while immobilized on the solid support.

In yet another variation, when a lysine-based linker comprising a reactive moiety R is conjugated by a TGase while the antibody is immobilized on a solid support, the antibody can be eluted from the solid support and the compound comprising a moiety Z and a reactive group R' can be reacted with the antibody in solution.

R' is a reactive moiety and can be defined in the same way as reactive group (R), so long as R' is complementary (reactive with) reactive group R. R' may be, for example, a moiety comprising an unprotected or protected bioorthogonal-reaction compatible reactive group, for example an unprotected or protected thiol, epoxide, maleimide, haloacetamide, o-phoshenearomatic ester, azide, fulminate, sulfonate ester, alkyne, cyanide, amino-thiol, carbonyl, aldehyde, generally any group capable of oxime and hydrazine formation, 1,2,4,5-tetrazine, norbornene, other stained or otherwise electronically activated alkene, a substituted or unsubstituted cycloalkyne, generally any reactive groups which form via bioorthogonal cycloaddition reaction a 1,3- or 1,5-disubstituted triazole, any diene or strained alkene dienophile that can react via inverse electron demand Diels-Alder reaction, a protected or unprotected amine, a carboxylic acid, an aldehyde, an oxyamine, so long as such group when unprotected is reactive with R (when R' is unprotected).

When more than one R' group is present in a compound of the formula, the R' groups will preferably be compatible such that no R' group is a complementary reagent to any other R' group. The L', V' and/or Y' groups of formulae I-IV can have r, q, and/or z sites of attachment for the respective V', Y', and R' groups, where r and q represent the degree of branching or polymerization. The sites of attachment can comprise a bond or comprise a functional group selected from an alkene, alkyne, ether, thioether, ester, thioester, amine, amide, alkylamide, or other functional group readily generated by a condensation or addition reaction.

In one embodiment, R' is a moiety having a terminal alkyne or azide, a substituted or unsubstituted cycloalkyne, for example a compound of Formula A (above), a modified cycloalkyne is of Formula B (above), or a substituted or unsubstituted heterocyclic strained alkyne of Formula C (above).

Any one of the R' moieties disclosed herein can be utilized in Formula III. Any one of the R' moieties described herein can be used in combination with any of the L', V', Y', Z, z', q', and r' groups described herein.

The compounds of (e.g. Formula III) to be used in reaction with an antibody can be reacted with antibody (e.g., 1 mg/mL) at ligand concentrations between 2 and 20 (or between 4 and 20) molar equivalents to the antibody, optionally between 2 and 10 (or between 4 and 10) molar equivalents to the antibody, optionally at a less than, or about, 20, 10, 5, 4 or 2 molar equivalents to the antibody. However it will be appreciated that higher excess (equivalents of reaction partner (e.g. Formula III) to antibody (40 to 80 fold, 60 to 90-fold) can also be used.

The compounds of Formula III to be used in reaction with an antibody conjugated to a lysine-based linker (but without a moiety-of-interest), e.g., an antibody of Formula II, as well as the resulting antibody conjugates therefore comprise one or more moieties-of-interest Z. The compounds of Formula III may additionally comprise a moiety V and/or Y, typically depending on which elements are included in the lysine-based linker.

The compounds of Formula III to be used in reaction with an antibody conjugated to a lysine-based linker (e.g. an antibody of Formula II) will comprise moieties Z connected to linker L' when Y' and V' are absent, connected to the spacer system Y' or, when Y' is absent, connected to V'. Consequently, a compound of Formula III may comprise a moiety Z connected to or comprising a reactive group R', optionally the moiety Z connected to a reactive group R' via a spacer system Y' or, when Y' is absent, to a reactive group R' via V', or to a reactive group R' via a V'—Y', wherein Z is preferably connected to Y' and V' is connected to R' and Y'.

A compound of Formula III may contain one, two or more Z moieties that are the same or that differ from one another, e.g. different therapeutic moieties, and/or diagnostic moieties.

In one embodiment, the antibody of Formula II is reacted with a compound of Formula III comprising a moiety of interest Z comprising and a reactive group R' capable of forming a bond with reactive group R of Formula Ib or II, optionally wherein the compound further comprises a V' and/or Y' group. The compound comprising a moiety of interest Z comprising and a reactive group R' preferably comprises a structure of Formula III, below,

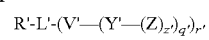

Formula III where:

R' is a reactive group, e.g. a reactive group complementary for forming at least one bond with reactive group R of Formula Ib or II;

L' is a bond or a carbon comprising framework of 1 to 200 atoms substituted at one or more atoms, optionally wherein the carbon comprising framework is a linear hydrocarbon, a symmetrically or asymmetrically branched hydrocarbon monosaccharide, disaccharide, linear or branched oligosaccharide (asymmetrically branched or symmetrically branched), other natural linear or branched oligomers (asymmetrically branched or symmetrically branched), or a dimer, trimer, or higher oligomer (linear, asymmetrically branched or symmetrically branched) resulting from any chain-growth or step-growth polymerization process;

V' is independently absent, a non-cleavable moiety or a conditionally-cleavable moiety that can optionally be cleaved or transformed by a chemical, photochemical, physical, biological, or enzymatic process, cleavage of V ultimately leading to release of one or more Z moieties. In some embodiments, V is, preferably, a di-, tri-, tetra-, or oligopeptide as described below in the section entitled "The V Moiety", Y' is independently absent or a spacer system (e.g., a self-eliminating spacer system or a non-self-elimination spacer system) which is comprised of 1 or more spacers, Z is independently a reactive group (optionally protected) other than a complementary reactive group for reaction with R', a moiety that improves the pharmacokinetic properties, a therapeutic moiety, or diagnostic moiety;

q' and r' are an integer selected among 1, 2, 3 or 4, representing degree of branching; and z' is an integer selected among 1, 2, 3 or 4.

Where Z is a reactive group, it can be a moiety comprising an unprotected or protected thiol, maleimide, haloacetamide, o-phoshenearomatic ester, azide, fulminate, alkyne, cyanide, anthracene, 1,2,4,5-tetrazine, norbornene, other stained or otherwise electronically activated alkene or, optionally, a protected or unprotected amine when X is absent and L, V, or Y is other than a bond or a continuation of a bond. In an alternative embodiment Z can be a reactive moiety, preferably a moiety comprising an unprotected or protected thiol, an unprotected or protected amine, maleimide, haloacetamide, o-phoshenearomatic ester, azide, fulminate, alkyne, cyanide, anthracene, 1,2,4,5-tetrazine, norbornene, other stained or otherwise electronically activated alkene. Preferably R is not an amine when n=5 and X, L, V and Y are absent. Preferably R is not an amine when n=4 and X, L, V and Y are absent.

The moiety R' is connected to Z, or optionally to Z via V' and/or Y' and is able to react with a suitable functional group R on a reaction partner, e.g. group R on the lysine-based linker of formula Ib or II. As discussed above, when the reactive moiety R' is designed to react with a reactive group R, a compound of Formula or IVb is formed.

The L' group can be a carbon comprising framework, where L is a symmetrically or asymmetrically branched hydrocarbon, monosaccharide, disaccharide, oligosaccharide, other natural oligomer, dimer, trimer, or higher oligomer resulting from any chain-growth or step-growth polymerization process, wherein L' has r', q', and/or z' sites of attachment for the respective V', Y', and R' groups, where r' and q' represent the degree of branching or polymerization. The sites of attachment can comprise a bond or comprise a functional group selected from an alkene, alkyne, ether, thioether, ester, thioester, amine, amide, alkylamide, or other functional group readily generated by a condensation or addition reaction.

The linking group (RR') in M of compounds of Formula IVb represents the R' addition product of a reactive moiety R' and a reactive moiety R. This group then links the moiety Z with L, V or Y, preferably via (RR') of M is L', V', and/or Y'. The group that remains may be a bond. Typically, however, L', V', and/or Y' is a linking group. RR' can be an addition product of a: thio-maleimide (or haloacetamide) addition, for example, a N,S-disubstituted-3-thio-pyrrolidine-2,5-dione; Staudinger ligation, for example, a N,3- or N,4-substituted-5-dipenylphosphinoxide-benzoic amide; Huisgen 1,3-cycloaddition (click reaction), for example, a N,S-disubstituted-3-thio-pyrrolidine-2,5-dione, 1,4-disubstituted-1,2,3-triazole, 3,5-disubstituted-isooxazole, or 3,5-disubstituted-tetrazole; Diels-Alder cycloaddition adduct, for example the 2,4-cycloaddition product between an O or N-substituted-5-norbornene-2-carboxylic ester or amide, N-substituted-5-norbornene-2,3-dicarboxylic imide, O or N-substituted-7-oxonorbornene-5-carboxylic ester or amide, or N-substituted-7-oxonorbornene-5,6-dicarboxylic imide and a 9-substituted anthracene or 3-substituted 1,2,4,5-tetrazine; or any high yield selective amidation or imidization reaction. Some reactions and the RR' reaction products are illustrated in FIGS. 1 and 2.

The Moiety Z

The moieties Z can be connected to Y or Y' or, when absent, to V or V', or, when absent, to L or, when absent to X, or to L' or, when absent to R', (RR'), or to $(C)_n$. Connections to Y, V or L may optionally be via R or RR'. Connection may be via any suitable atoms. In one embodiment, Z is coupled via oxygen (from for example a hydroxyl group or carboxyl group), carbon (from for example a carbonyl group), nitrogen (from for example a primary or secondary amino group), or sulfur (from for example a sulfhydryl group). In one embodiment, Z is coupled in the compounds via a group such that its therapeutic abilities or diagnostic characteristics are, at least partly, blocked or masked. In case a compound is to be used for treating or preventing disease in an animal, e.g., a mammal, the Z moieties are generally therapeutic moieties. In case a compound is used to make a diagnosis or used in an ex vivo or in vivo diagnostic assay, the Z moieties are generally diagnostic moieties, for example chromogenic, fluorogenic, phosphorogenic, chemiluminescent, or bio luminescent compounds.

In one embodiment, the Z moiety is compound, preferably an organic compound, having a molecular weight of at least 300 g/mol, 400 g/mol, 500 g/mol, 600 g/mol, 700 g/mol, 800 g/mol, 900 g/mol, 1000-g/mol or 2000 g/mol.

In one embodiment, the Z moiety is a chemical compound displaying hydrophobic properties, optionally additionally having a molecular weight of at least 300 g/mol, 400 g/mol, 500 g/mol, 600 g/mol, 700 g/mol, 800 g/mol, 900 g/mol. 1000-g/mol or 2000 g/mol. Hydrophobic character may be determined, for example, by decreased water solubility, decreased polarity, decreased potential for hydrogen bonding, and/or an increased oil/water partition coefficient. The presently disclosed methods can be used to produce antibody conjugates where moiety of interest (Z) comprises a hydrophobic drug. As used herein, the term "hydrophobic" is a physical property of a molecule that is repelled from a mass of water. Hydrophobic compounds can be solubilized in nonpolar solvents, including but not limited to, organic solvents. Hydrophobicity can be conferred by the inclusion of apolar or nonpolar chemical groups that include, but are not limited to, saturated and unsaturated aliphatic hydrocarbon groups and such groups substituted by one or more aromatic, cycloaliphatic or heterocyclic group(s). Conversely, "hydrophilic" molecules are capable of hydrogen bonding with a water molecule and are therefore soluble in water and other polar solvents. The terms "hydrophilic" and "polar" can be used interchangeably. Hydrophilic characteristics derive from the presence of polar or charged groups, such as carbohydrates, phosphate, carboxylic, sulfato, amino, sulfhydryl, nitro, hydroxy and other like groups.

Hydrophobic molecules are poorly water soluble, for example, having a solubility of less than about 10 mg/ml. In some embodiments, the hydrophobic compound can have a solubility of less than about 1 mg/ml in water. In other embodiments, the hydrophobic compound has a solubility in water of less than about 50, µg/ml, 10 µg/ml, and in particular embodiments, about 1 µg/ml or 2.5 µg/ml. In other embodiments, the hydrophobic compound can have a solubility of about 0.001 µg/ml to about 10 mg/ml, including but not limited to 0.001 µg/ml, 0.01 µg/ml, 0.1 µg/ml, 1 µg/ml, 2 µg/ml, 5 µg/ml, 10 µg/ml, 50 µg/ml, 100 µg/ml, 500 µg/ml, 1 mg/ml, 5 mg/ml, and 10 mg/ml, and any other concentration between 0.001 µg/ml and 10 mg/ml.

Representative, non-limiting examples of hydrophobic drugs that can be formulated using the presently disclosed methods include taxanes, e.g. paclitaxel (PTX), and camptothecin (CPT), maytansanoids, duocarmycins, dolastatins and auristatins. Such drugs are poorly soluble in water, e.g. PTX has a solubility in water of less than about 1 µg/ml, CPT has a water solubility of about 2.5 µg/ml. Linkers and modified an antibodies can advantageously link hydrophobic drugs to an antibodies.

In other embodiments, in view of hydrophobic drugs being poor substrates for TGase (in the absence of improved linkers or modified an antibodies), the Z moiety may advantageously be a hydrophilic drug. Examples of hydrophilic drugs include amatoxins. Amatoxins are cyclic peptides composed of 8 amino acids as isolated from the genus Amanita. Amatoxins also include a range of chemical derivatives, semisynthetic analogs and synthetic analogs built from building blocks according to the master structure of the −5 natural compounds (cyclic, 8 amino acids), synthetic or semisynthetic analogs containing non-hydroxylated amino acids instead of the hydroxylated amino acids, synthetic or semisynthetic analogs, in which the thioether sulfoxide moiety is replaced by a sulfide, sulfone, or by atoms different from sulfur, e.g. a carbon atom as in a carbaanalog of amanitin. Functionally, amatoxins are defined as peptides or depsipeptides that inhibit mammalian RNA polymerase II. Preferred amatoxins are those with a functional group (e.g. a carboxylic group, an amino group, a hydroxy group, a thiol or a thiol-capturing group) that can be reacted with linker molecules or proteins. Amatoxins are described for example in European Patent publication no. 1859811, PCT publication nos. WO 2010/115630 and WO 2012/041504).

In one embodiment, the Z moiety is a large compound (e.g., molecular weight of at least 300 g/mol, 400 g/mol, 500 g/mol, 600 g/mol or 700 g/mol) comprising a polycyclic group, tricycle or one or more macrocycles. Such groups are often typical of hydrophobic and/or rigid structures. Examples of cytotoxic drugs that comprise a macrocycle (e.g. a ring of nine or more atoms) include maytansinoids, amatoxins, epothilones and taxanes. In one embodiment, the Z moiety comprises a ring of 9, 10, 11, 12, 13, 14, 15, 16, 17 or 18 atoms, or between 9 and 200 atoms. In one embodiment, the Z moiety is a chemical compound having a negative charge, optionally additionally displaying hydrophobic properties and/or having a molecular weight of at least 300 g/mol, 400 g/mol, 500 g/mol, 600 g/mol, 700 g/mol, 800 g/mol, 900 g/mol, 1000 g/mol or 2000 g/mol.

When more than one Z moiety is connected to a self-elimination spacer system Y or Y', at least one Z should be released upon self-elimination of Y or Y'. The moiety Z initially released may be a moiety that is not a fully active moiety itself. In other words, Z may be a moiety that has limited diagnostic or therapeutic abilities, e.g. a moiety that acts as a prodrug. Such a Z moiety may require further processing or metabolism, e.g., hydrolysis, enzymatic cleavage, or enzymatic modification (for example phosphorylation, reduction, or oxidation) in order to become fully active. In one embodiment, such further processing is intentionally designed for Z to for example allow Z to reach its final target or cross a biological barrier, e.g., a cell membrane or a nuclear membrane, before it is fully activated. Z may for example contain a hydrophobic moiety that enables Z to cross a cell membrane. This hydrophobic moiety may then be hydrolyzed or removed in any other way intracellularly.

In one aspect, a Z moiety may be a backbone (e.g. polymer) to which a plurality of drugs or diagnostic moieties are linked. For example, Z may be a polyacetal- or polyacetal derivative-based polymer comprising a plurality of drug molecules, see, e.g., Yurkovetskiy et al. (2004) Mol. Pharm. 1(5): 375-382 and WO 2011/120053, the disclosures of which are incorporated herein by reference; for example Z may be a polymer compound of Formula I of WO 2011/120053 comprising a plurality of cytotoxic anti-cancer agents.

In one aspect, one or more moieties Z are each selected from a therapeutic or diagnostic agent. In another embodiment, one or more moieties Z are each a therapeutic agent. In another embodiment, all moieties Z are each a therapeutic agent. In yet another embodiment, the moieties Z each are the same therapeutic moiety. In yet another embodiment, the moieties Z comprise at least two different therapeutic moieties.

The moiety Z includes, for example, antineoplastic agents, drugs, toxins (such as enzymatically active toxins of bacterial or plant origin and fragments thereof e.g. ricin and fragments thereof) biologically active proteins, for example enzymes, other an antibodies, synthetic or naturally occurring polymers, nucleic acids and fragments thereof e.g. DNA, RNA and fragments thereof, radionuclides, particularly radioiodide, radioisotopes, chelated metals, nanoparticles and reporter groups such as fluorescent compounds or compounds which may be detected by NMR or ESR spectroscopy.

In one embodiment, the one or more moieties Z are each independently chosen from an antibiotic, an anti-bacterial agent, an antimicrobial agent, an anti-inflammatory agent, an anti-infectious disease agent, an anti-autoimmune disease agent, an anti-viral agent, or an anticancer agent, preferably a cytotoxic anti-cancer agent.

In another embodiment, the one or more moieties Z are each an anticancer agent. In a further embodiment, the one or more moieties Z are each a hydroxyl-containing anticancer agent.

In one embodiment, Z is an alkylating agent, preferably a DNA alkylating agent. An alkylation agent is a compound that can replace a hydrogen atom with an alkyl group under physiological conditions (e.g. pH 7.4, 37 C, aqueous solution). Alkylation reactions are typically described in terms of substitution reactions by N, O and S heteroatomic nucleophiles with the electrophilic alkylating agent, although Michael addition reactions are also important. Examples of alkylating agents include nitrogen and sulfur mustards, ethylenimines, methanosulfonates, CC-1065 and duocarmycins, nitrosoureas, platinum-containing agents, agents that effectuate Topoisomerase II-mediated site dependent alkylation of DNA (e.g. psorospermin and related bisfuranoxanthones), ecteinascidin and other or related DNA minor groove alkylation agents.

In one embodiment, Z is a DNA minor groove binding and/or alkylating agent, e.g. a pyrrolobenzodiazepine, a duocarmycin, or derivatives thereof.

calicheamycin, mertansine (DM1), N-acetyl-$\gamma_1$'-calicheamycin, calicheamycin-$\gamma_1$', calicheamycin-$\alpha_2$', calicheamycin-$\alpha_3$', duocarmycin SA, duocarmycin A, CC-1065, CBI-TMI, duocarmycin C2, duocarmycin B2, centanamycin, dolastatin, auristatin E, monomethylauristatin E (MMAE), monomethylauristatin F (MMAF), $\alpha$-amanitin, $\beta$-amanitin, $\gamma$-amanitin, $\epsilon$-amanitin, amanin, amaninamide, amanullin, and amanullinic acid and derivatives thereof.

Exemplary auristatin embodiments include the N-terminus linked monomethylauristatin drug moieties comprising a structure of any of Formulas V and VI below:

Formula V

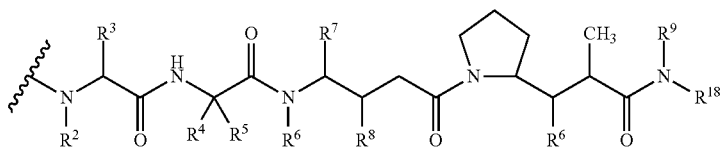

Formula VI

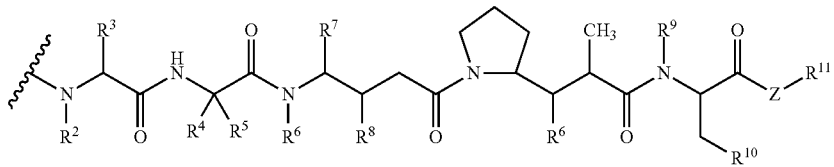

In a further embodiment, the one or more moieties Z are each independently selected from the group consisting of taxanes, anthracyclines, camptothecins, epothilones, mytomycins, combretastatins, *vinca* alkaloids, nitrogen mustards, maytansinoids, calicheamycins, duocarmycins, tubulysins, dolastatins and auristatins, enediynes, amatoxins, pyrrolobenzodiazepines, ethylenimines, radioisotopes, therapeutic proteins and peptides, and toxins or fragments thereof.

In a further embodiment, the one or more moieties Z are each independently selected from cyclophosphamide, ifosfamide, chlorambucil, 4-(bis(2-chloroethyl)amino)phenol, 4-(bis(2-fluoroethyl)ammo)phenol, N,N-bis(2-chloroethyl)-p-phenylenediamine, N,N-bis(2-fluoro-ethyl)-p-phenylenediamine, carmustine, lomustine, treosulfan, dacarbazine, cisplatin, carboplatin, vincristine, vinblastine, vindesine, vinorelbine, paclitaxel, docetaxel, etoposide, teniposide, topotecan, inirotecan, 9-aminocamptothecin, 9-nitrocamptothecin, 10-hydroxycamptothecin, lurtotecan, camptothecin, crisnatol, mitomycin C, mitomycin A, methotrexate, trimetrexate, mycophenolic acid, tiazofurin, ribavirin, hydroxyurea, deferoxamine, 5-fluorouracil, floxuridine, doxifluridine, raltitrexed, cytarabine, cytosine arabinoside, fludarabine, 6-mercaptopurine, thioguanine, raloxifen, megestrol, goserelin, leuprolide acetate, flutamide, bicalutamide, vertoporfin, phthalocyanine, photosensitizer Pc4, demethoxy-hypocrellin A, interferon-alpha, interferon-gamma, tumor necrosis factor, lovastatin, staurosporine, actinomycin D, bleomycin A2, bleomycin B2, peplomycin, daunorubicin, doxorubicin, N-(5,5-diacetoxypentyl)doxorubicin, morpholino doxorubicin, idarubicin, epirubicin, pirarubicin, zorubicin, mitoxantrone, thapsigargin, $N^8$-acetylspermidine, tallysomycin, esperamycin, butyric acid, retinoic acid, 1,8-dihydroxybicyclo[7.3.1]trideca-4-ene-2,6-diyne-13-one, anguidine, podophyllotoxin, combretastatin A-4, pancratistatin, tubulysin A, tubulysin D, carminomycin, streptonigrin, elliptmium acetate, maytansine, maytansinol, wherein the wavy line of V and VI indicates the covalent attachment site to a L, L', V, V', Y, Y', (RR'), R' or (C)$_n$ group of a compound (e.g. a compound of Formula I, II or IV), and independently at each location:

$R^2$ is selected from H and $C_1$-$C_8$ alkyl;

$R^3$ is selected from H, $C_1$-$C_8$ alkyl, $C_1$-$C_8$ carbocycle, aryl, $C_1$-$C_8$ alkyl-aryl, $C_1$-$C_8$ alkyl-($C_3$-$C_8$ carbocycle), $C_3$-$C_8$ heterocycle and $C_1$-$C_8$ alkyl-($C_3$-$C_8$ heterocycle);

$R^4$ is selected from H, $C_1$-$C_8$ alkyl, $C_3$-$C_8$ carbocycle, aryl, $C_1$-$C_8$ alkyl-aryl, $C_1$-$C_8$ alkyl-($C_3$-$C_8$ carbocycle), $C_3$-$C_8$ heterocycle and $C_1$-$C_8$ alkyl-($C_3$-$C_8$ heterocycle);

$R^5$ is selected from H and methyl;

or $R^4$ and $R^5$ jointly form a carbocyclic ring and have the formula —$(CR^aR^b)_n$— wherein $R^a$ and $R^b$ are independently selected from H, $C_1$-$C_8$ alkyl and $C_3$-$C_8$ carbocycle and n is selected from 2, 3, 4, 5 and 6;

$R^6$ is selected from H and $C_1$-$C_8$ alkyl;

$R^7$ is selected from H, $C_1$-$C_8$ alkyl, $C_3$-$C_8$ carbocycle, aryl, $C_1$-$C_8$ alkyl-aryl, $C_1$-$C_8$ alkyl-($C_3$-$C_8$ carbocycle), $C_3$-$C_8$ heterocycle and $C_1$-$C_8$ alkyl-($C_3$-$C_8$ heterocycle);

each $R^8$ is independently selected from H, OH, $C_1$-$C_8$ alkyl, $C_3$-$C_8$ carbocycle and O—($C_1$-$C_8$ alkyl);

$R^9$ is selected from H and $C_1$-$C_8$ alkyl;

$R^{10}$ is selected from aryl or $C_3$-$C_8$ heterocycle;

Z is O, S, NH, or $NR^{12}$ wherein $R^{12}$ is $C_1$-$C_8$ alkyl;

$R^{11}$ is selected from H, $C_1$-$C_{20}$ alkyl, aryl, C3-C8 heterocycle, —$(R^{13}O)_m$—$R^{14}$, or —$(R^{13}O)_m$—$CH(R^{15})_2$; m is an integer ranging from 1-1000;

$R^{13}$ is $C_2$-$C_8$ alkyl;

$R^{14}$ is H or $C_1$-$C_8$ alkyl;

each occurrence of $R^{15}$ is independently H, COOH, —$(CH_2)_n$—$N(R^{16})_2$, —$(CH_2)_n$—$SO_3$—$C_1$-$C_8$ alkyl;

each occurrence of $R^{16}$ is independently H, $C_1$-$C_8$ alkyl, or —$(CH_2)_n$—COOH;

$R^{18}$ is selected from —$C(R^8)_2$—$C(R^8)_2$-aryl, —$C(R^8)_2$—$C(R^8)_2$—($C_3$-$C_8$ heterocycle), and —$C(R^8)_2$—$C(R^8)_2$—($C_3$-$C_8$ carbocycle); and n is an integer ranging from 0 to 6.

In one embodiment, $R^3$, $R^4$ and $R^7$ are independently isopropyl or sec-butyl and $R^5$ is —H or methyl. In an exemplary embodiment, $R^3$ and $R^4$ are each isopropyl, $R^5$ is —H, and $R^7$ is sec-butyl.

In yet another embodiment, $R^2$ and $R^6$ are each methyl, and $R^9$ is —H.

In still another embodiment, each occurrence of $R^8$ is —OCH$_3$.

In an exemplary embodiment, $R^3$ and $R^4$ are each isopropyl, $R^2$ and $R^6$ are each methyl, $R^5$ is —H, $R^7$ is sec-butyl, each occurrence of $R^8$ is —OCH$_3$, and $R^9$ is —H.

In one embodiment, Z is —O— or —NH—.

In one embodiment, $R^{19}$ is aryl.

In an exemplary embodiment, $R^{19}$ is -phenyl.

In an exemplary embodiment, when Z is —O—, $R^{11}$ is —H, methyl or t-butyl.

In one embodiment, when Z is —NH, $R^{11}$ is —CH($R^{15}$)$_2$, wherein $R^{15}$ is —(CH$_2$)$_n$—N($R^{16}$)$_2$, and $R^{16}$ is —C$_1$-C$_8$ alkyl or —(CH$_2$)$_n$—COOH.

In another embodiment, when Z is —NH, $R^{11}$ is —CH($R^{15}$)$_2$, wherein $R^{15}$ is —(CH$_2$)$_n$—SO$_3$H.

One exemplary auristatin embodiment of formula V is MMAE, wherein the wavy line indicates the covalent attachment to a L, L', V, V', Y, Y', (RR'), R' or (C)$_n$ group of a compound (e.g. a compound of Formula I, II or IV):

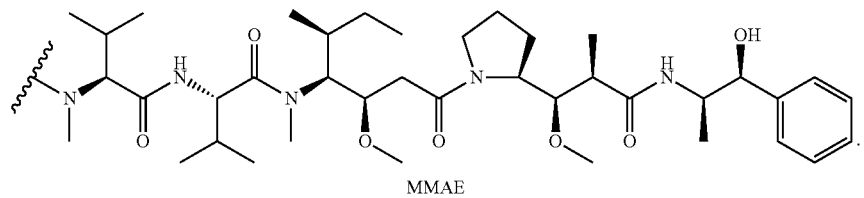 [SMILES: *N(C)[C@H](C(=O)N[C@H](C(=O)N(C)[C@@H]([C@@H](C)CC)[C@@H](CC(=O)N1CCC[C@H]1[C@H](OC)[C@@H](C)C(=O)N[C@H](C)[C@@H](O)c1ccccc1)OC)C(C)C)C(C)C]

MMAE

An exemplary auristatin embodiment of formula VI is MMAF, wherein the wavy line indicates the covalent attachment to a linker (L) of an antibody-drug conjugate (see US 2005/0238649 and Doronina et al. (2006) Bioconjugate Cfiem. 17: 1 14-124):

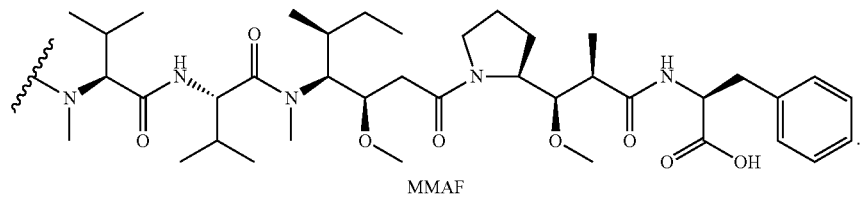

MMAF

Other exemplary Z embodiments include monomethylvaline compounds having phenylalanine carboxy modifications at the C-terminus of the pentapeptide auristatin drug moiety (WO 2007/008848) and monomethylvaline compounds having phenylalanine sidechain modifications at the C-terminus of the pentapeptide auristatin drug moiety (WO 2007/008603).

An example of a linker comprising a lysine residue as (C)$_n$ moiety, a valine-citrulline as the (V) moiety, a PAB as the (Y) moiety together with a MMAF as the (Z) moiety is shown below (corresponding to compound Ia-1):

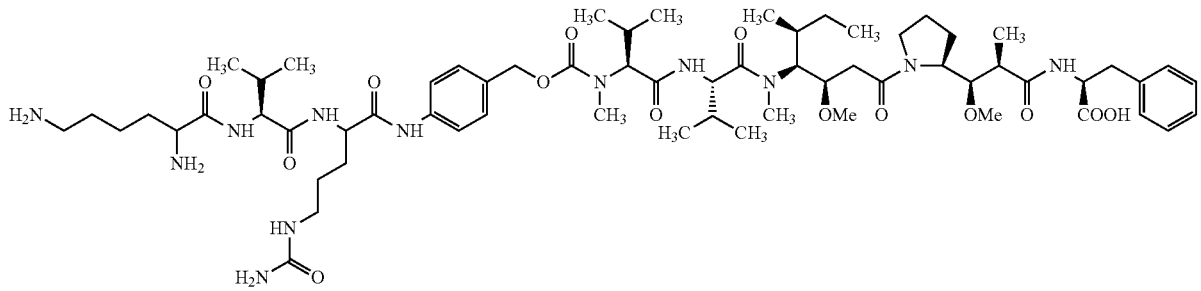 [SMILES: CC[C@H](C)[C@@H]([C@@H](CC(=O)N1CCC[C@H]1[C@H](OC)[C@@H](C)C(=O)N[C@@H](Cc1ccccc1)C(=O)O)OC)N(C)C(=O)[C@@H](NC(=O)[C@H](C(C)C)N(C)C(=O)OCc1ccc(NC(=O)C(CCCNC(N)=O)NC(=O)[C@@H](NC(=O)C(N)CCCCN)C(C)C)cc1)C(C)C]

In one embodiment, the Z moiety is an epothilone or epothilone derivative. An epothilone is a cyclic molecule with a 16-membered ring and variable substituents and pharmaceutical activity as a cytostatic agent that binds to tubulin. Various epothilone derivatives are known, including variants with 14-, 15- or 18-membered rings have also been developed (e.g. WO 2011085523; WO 2009105969). Examples of epothilones or epothilone analogs or derivative include epothilone A, epothilone B, epothilone C, 13-alkyl-epothilone C derivatives, epothilone D, trans-epothilone D, epothilone E, epothilone F, an effector conjugate of epothilone, Sagopilone, or any of the epothilones referred to in the literature as ixabepilone (BMS-247550), BMS-310705, EPO-906, Patupilone, Kos-862, Kos-1584, Kos-1803 and ABJ 879, and pharmaceutically active salts thereof. The production of epothilones, their precursors and derivatives is generally carried out according to the methods known to one skilled in the art. Suitable methods are, for example, described in DE 19907588, WO 98/25929, WO 99/58534, WO 99/2514, WO 99/67252, WO 99/67253, WO 99/7692, EP 99/4915, WO 00/485, WO 00/1333, WO 00/66589, WO 00/49019, WO 00/49020, WO 00/49021, WO 00/71521, WO 00/37473, WO 00/57874, WO 01/92255, WO 01/81342, WO 01/73103, WO 01/64650, WO 01/70716, U.S. Pat. Nos. 6,204,388, 6,387,927, 6,380,394, US 02/52028, US 02/58286, US 02/62030, WO 02/32844, WO 02/30356, WO 02/32844, WO 02/14323, and WO 02/8440. Further epothilones are described in WO 93/10102, WO 98/25929, WO 99/02514, WO 99/07692, WO 99/02514, WO 99/67252, WO 00/49021, WO 00/66589, WO 00/71521, WO 01/027308, WO 02/080846, WO 03/074053, WO 2004/014919.

Chelated metals include chelates of di- or tripositive metals having a coordination number from 2 to 8 inclusive. Particular examples of such metals include technetium (Tc), rhenium (Re), cobalt (Co), copper (Cu), gold (Au), silver (Ag), lead (Pb), bismuth (Bi), indium (In), gallium (Ga), yttrium (Y), terbium (Tb), gadolinium (Gd), and scandium (Sc). In general the metal is preferably a radionuclide. Particular radionuclides include $^{99m}$TC, $^{186}$Re, $^{188}$Re, $^{58}$Co, $^{69}$Co, $^{67}$Cu, $^{195}$Au, $^{199}$Au, $^{110}$Ag, $^{203}$Pb, $^{206}$Bi, $^{207}$Bi, $^{111}$In, $^{67}$Ga, $^{68}$Ga, $^{88}$Y, $^{90}$Y, $^{160}$Tb, $^{153}$Gd and $^{47}$Sc.

The chelated metal may be for example one of the above types of metal chelated with any suitable polydentate chelating agent, for example acyclic or cyclic polyamines, polyethers, (e.g. crown ethers and derivatives thereof); polyamides; porphyrins; and carbocyclic derivatives.

In general, the type of chelating agent will depend on the metal in use. One particularly useful group of chelating agents in conjugates, however, are acyclic and cyclic polyamines, especially polyaminocarboxylic acids, for example diethylenetriaminepentaacetic acid and derivatives thereof, and macrocyclic amines, e.g. cyclic tri-aza and tetra-aza derivatives (for example as described in PCT publication no. WO 92/22583); and polyamides, especially desferriox-amine and derivatives thereof.

Other effector molecules may include detectable substances useful for example in diagnosis. Examples of detectable substances include various enzymes, prosthetic groups, fluorescent materials, luminescent materials, bioluminescent materials, radioactive nuclides, positron emitting metals (for use in positron emission tomography), and nonradioactive paramagnetic metal ions. See generally U.S. Pat. No. 4,741,900 for metal ions which can be conjugated to antibodies for use as diagnostics. Suitable enzymes include horseradish peroxidase, alkaline phosphatase, beta-galactosidase, or acetylcholinesterase; suitable prosthetic groups include streptavidin, avidin and biotin; suitable fluorescent materials include umbelliferone, fluorescein, fluorescein isothiocyanate, rhodamine, dichlorotriazinylamine fluorescein, dansyl chloride and phycoerytbrin; suitable luminescent materials include luminol; suitable bioluminescent materials include luciferase, luciferin, and aequorin; and suitable radioactive nuclides include $^{125}$I, $^{131}$I, $^{111}$In and $^{99}$Tc.

Synthetic or naturally occurring polymers for use as effector molecules include, for example optionally substituted straight or branched chain polyalkylene, polyalkenylene, or polyoxyalkylene polymers or branched or unbranched polysaccharides, e.g. a homo- or hetero-polysaccharide such as lactose, amylose, dextran or glycogen.

Particular optional substituents which may be present on the above-mentioned synthetic polymers include one or more hydroxy, methyl or methoxy groups. Particular examples of synthetic polymers include optionally substituted straight or branched chain poly(ethyleneglycol), poly(propyleneglycol), poly(vinylalcohol) or derivatives thereof, especially optionally substituted poly(ethyleneglycol) such as methoxypoly(ethyleneglycol) or derivatives thereof. Such compounds, when used as a moiety Z can be employed as a moiety that improves the pharmacokinetic properties of the antibody.

The size of the polymer may be varied as desired, but will generally be in an average molecular weight range from 500 Da to 50,000 Da, preferably from 5,000 to 40,000 Da and more preferably from 10,000 to 40,000 Da and 20,000 to 40,000 Da. The polymer size may in particular be selected on the basis of the intended use of the product for example ability to localize to certain tissues such as tumors or extend circulating half-life (for review see Chapman, 2002, Advanced Drug Delivery Reviews, 54, 531-545). Thus, for example, where the product is intended to leave the circulation and penetrate tissue, for example for use in the treatment of a tumor, it may be advantageous to use a small molecular weight polymer, for example with a molecular weight of around 5,000 Da. For applications where the product remains in the circulation, it may be advantageous to use a higher molecular weight polymer, for example having a molecular weight in the range from 20,000 Da to 40,000 Da.

Particularly preferred polymers include a polyalkylene polymer, such as a poly(ethyleneglycol) or, especially, a methoxypoly(ethyleneglycol) or a derivative thereof, and especially with a molecular weight in the range from about 10,000 Da to about 40,000 Da.

In another embodiment, z' equals 1, each V, Y or V—Y (including whether any V and Y is a V' or Y') moiety contains a single attachment site for a functional group of Z. In another embodiment, a one V (or V'), Y, (or Y') or V—Y (or V'—Y', V—Y') moiety is attached to more than one Z moiety via multiple functional groups R on the said V, Y or V—Y moiety. Optionally, the one or more V (or V') moieties comprise a polymer, optionally an oligoethylene glycol or a polyethylene glycol or a derivative thereof.

Any one of the Z moieties disclosed herein can be utilized in Formula Ia, IIII, and IVa. Any one of the Z moieties described herein can be used in combination with any of the (C)$_n$, X, L, V, R, Y, Z, M, z, q, and r groups described herein. Any one of the Z moieties described herein can be used in combination with any of the R', L', V', Y', z', q', and r' groups described herein.

Antibody-Z Conjugates

In one embodiment, a linking reagent (e.g. of Formula Ia) is directly conjugated to an antibody, without requirement for a step of reaction involving reactive groups R and R'. In one aspect, an antibody comprises a functionalized glutamine residue of Formula IVa, below,

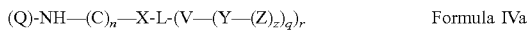  Formula IVa or a pharmaceutically acceptable salt thereof;
wherein:
Q is glutamine residue present in an antibody;
(C)$_n$ is a substituted or unsubstituted alkyl or heteroalkyl chain, wherein any carbon of the chain is optionally substituted with an alkoxy, hydroxyl, alkylcarbonyloxy, alkyl-S—, thiol, alkyl-C(O)S—, amine, alkylamine, amide, or alkylamide (e.g. a O, N or S atom of an ether, ester, thioether, thioester, amine, alkylamine, amide, or alkylamide);
n is an integer selected from among the range of 2 to 20;
X is NH, O, S, or absent;
L is a bond or a carbon comprising framework, preferably of 1 to 200 atoms substituted at one or more atoms, optionally wherein the carbon comprising framework is a linear hydrocarbon, a symmetrically or asymmetrically branched hydrocarbon monosaccharide, disaccharide, linear or branched oligosaccharide (asymmetrically branched or symmetrically branched), other natural linear or branched oligomers (asymmetrically branched or symmetrically branched), or a dimer, trimer, or higher oligomer (linear, asymmetrically branched or symmetrically branched) resulting from any chain-growth or step-growth polymerization process;
r is an integer selected among 1, 2, 3 or 4;
q is an integer selected among 1, 2, 3 or 4;
z is an integer selected among 1, 2, 3 or 4; and
V is independently absent, a non-cleavable moiety or a conditionally-cleavable moiety that can optionally be cleaved or transformed by a chemical, photochemical, physical, biological, or enzymatic process (e.g. cleavage of V ultimately leading to release of one or more moieties subsequently or ultimately linked to V, for example a Z moiety). In some embodiments, V is, preferably, a di-, tri-, tetra-, or oligopeptide as described below in the section entitled "The V Moiety";
Y is independently absent or a spacer (e.g., a self-eliminating spacer system or a non-self-elimination spacer system) which is comprised of 1 or more spacers; and
Z is a moiety-of-interest, optionally a moiety that improves the pharmacokinetic properties, or a therapeutic moiety or a diagnostic moiety. Preferably, Z is a cytotoxic anti-cancer agent, e.g. a compound selected from the group consisting of taxanes, anthracyclines, camptothecins, epothilones, mytomycins, combretastatins, *vinca* alkaloids, nitrogen mustards, maytansinoids, calicheamycins, duocarmycins, tubulysins, amatoxins, dolastatins and auristatins, enediynes, radioisotopes, therapeutic proteins and peptides, and toxins or fragments thereof.
Generally, each Z is directly coupled to either Y or V when Y is absent, or L when both Y and V are absent.
It will be appreciated that Formula IVa can for convenience also be expressed as (Ab)-NH—(C)$_n$—X-L-(V—(Y—(Z)$_z$)$_q$)$_r$ (Formula IVa), where (Ab) is an immunoglobulin (Ab) is conjugated via a glutamine (Q) residue to an NH of the linking reagent (e.g. the compound of Formula Ia).
Examples of an antibodies of Formula IVa include but are not limited to an antibodies attached via an amide bond (e.g. through an acceptor glutamine residue in the primary sequence of the antibody) to a compound selected from the group consisting of compounds Ia-1 to Ia-23 (wherein the terminal NH$_2$— of each of said compound Ia-1 to Ia-23 is replaced by a moiety ((Q)-NH—) when attached to the antibody, wherein Q is glutamine residue present in an antibody, e.g. in the CH2 domain or in a TGase recognition tag fused to the C-terminus of the CH3 domain.
The antibody conjugates resulting from the reaction of the compounds of Formula Ib or III with an antibody conjugated to a lysine-based linker will yield an antibody conjugate in which a moiety Z is connected to linker L (or L') when Y (or Y') and V (or V') are absent, to the spacer system Y (or Y') or, when Y (or Y') is absent, to V (or V). Optionally said connections are via linking group (RR') of M.
The conjugates resulting from the reaction yield an antibody which is conjugated (i.e., covalently attached) via an acceptor glutamine residue (Q) present on the antibody to a NH group of a lysine-based linker, and one or more moieties (Z) through optional linking group (RR'), optional linker (V or V') and/or optional spacer (Y or Y').
In one embodiment, the (RR') remains present in a conjugated antibody, in which case a Formula IV will comprise an (M) moiety. Such an antibody comprises a functionalized glutamine residue of Formula IVb, below,

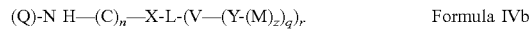  Formula IVb or a pharmaceutically acceptable salt or solvate thereof;
wherein:
Q is glutamine residue present in an antibody;
(C)$_n$ is a substituted or unsubstituted alkyl or heteroalkyl chain, wherein any carbon of the chain is optionally substituted with an alkoxy, hydroxyl, alkylcarbonyloxy, alkyl-S—, thiol, alkyl-C(O)S—, amine, alkylamine, amide, or alkylamide;
n is an integer selected from among the range of 2 to 20;
X is NH, O, S, or absent;
L is a bond or a carbon comprising framework, preferably of 1 to 200 atoms substituted at one or more atoms, optionally wherein the carbon comprising framework is a linear hydrocarbon, a symmetrically or asymmetrically branched hydrocarbon monosaccharide, disaccharide, linear or branched oligosaccharide (asymmetrically branched or symmetrically branched), other natural linear or branched oligomers (asymmetrically branched or symmetrically branched), or a dimer, trimer, or higher oligomer (linear, asymmetrically branched or symmetrically branched) resulting from any chain-growth or step-growth polymerization process;
r is an integer selected among 1, 2, 3 or 4;
q is an integer selected among 1, 2, 3 or 4;
z is an integer selected among 1, 2, 3 or 4; and
V is independently absent, a non-cleavable moiety or a conditionally-cleavable moiety that can optionally be cleaved or transformed by a chemical, photochemical, physical, biological, or enzymatic process (e.g. cleavage of V ultimately leading to release of one or more moieties subsequently or ultimately linked to V, for example a Z moiety). In some embodiments, V is, preferably, a di-, tri-, tetra-, or oligopeptide as described below in the section entitled "The V Moiety";
Y is independently absent or a spacer (e.g., a self-eliminating spacer system or a non-self-elimination spacer system) which is comprised of 1 or more spacers; and
M is independently: R or (RR')-L'-(V'—(Y'—(Z)$_z$)$_{q'}$)$_{r'}$, wherein each of L', V', Y', z', q', and r' are as defined in Formula III (or are defined as L, V, Y, z, q and r, respectively,
Z is a moiety-of-interest, optionally a moiety that improves the pharmacokinetic properties, or a therapeutic moiety or a diagnostic moiety, R is as defined in Formula I and wherein each (RR') is an addition product between an R of Formula I and its complementary R' of Formula III (see, for example, FIG. 1 and FIG. 2).

Thus, RR' can be for example an addition product of a thio-maleimide (or haloacetamide) addition, for example, a N,S-disubstituted-3-thio-pyrrolidine-2,5-dione; Staudinger ligation, for example, a N,3- or N,4-substituted-5-dipenyl-phosphinoxide-benzoic amide; Huisgen 1,3-cycloaddition (click reaction), for example, a N,S-disubstituted-3-thio-pyrrolidine-2,5-dione, 1,4-disubstituted-1,2,3-triazole, 3,5-disubstituted-isooxazole, or 3,5-disubstituted-tetrazole; Diels-Alder cycloaddition adduct, for example the 2,4-cycloaddition product between an O or N-substituted-5-norbornene-2-carboxylic ester or amide, N-substituted-5-norbornene-2,3-dicarboxylic imide, O or N-substituted-7-oxonorbornene-5-carboxylic ester or amide, or N-substituted-7-oxonorbornene-5,6-dicarboxylic imide and a 9-substituted anthracene or 3-substituted 1,2,4,5-tetrazine; or any high yield selective amidation or imidization reaction. Some reactions and the corresponding RR' reaction products are illustrated in FIGS. 1 and 2.

Examples of RR' include:

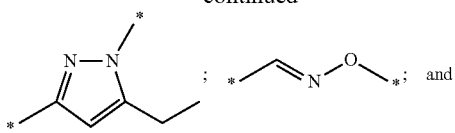

-continued

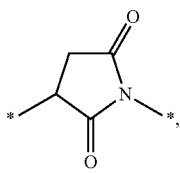

wherein (*) indicates the site of attachment of —(C)$_n$, X, L, L', V, V', Y, Y' or Z. RR' can be in either orientation with respect to their attachment to —(C)$_n$, X, L, L', V, V', Y, Y' or Z).

Optionally, the antibody conjugate comprises a group (RR') representing the remainder of a reactive moiety R when R has reacted with a reactive moiety R', wherein the group (RR') connects (a) an L to a Z, a V or a Y, (b) a V to a Z or a Y, or (c) a Y to a Z. For example, any V, Y and/or Z may be characterized as comprising a (RR') group. Any L, V, Y may be an L', V' or Y', respectively.

It will be appreciated that Formula IVb can for convenience also be expressed as (mFc)-NH—(C)$_n$—X-L-(V—(Y-(M)$_z$)$_q$)$_r$, where (mFc) is an antibody conjugated via a glutamine (Q) residue to an NH of the linking reagent (e.g. the compound of Formula Ib).

Examples of antibodies of Formula IVb include but are not limited to:

Compound IVb-1

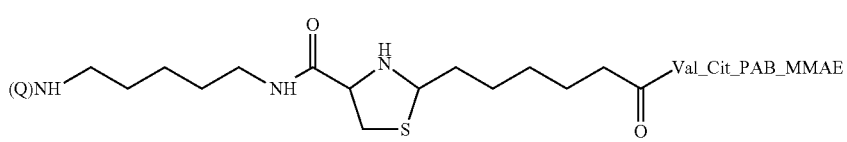

Compound IVb-2

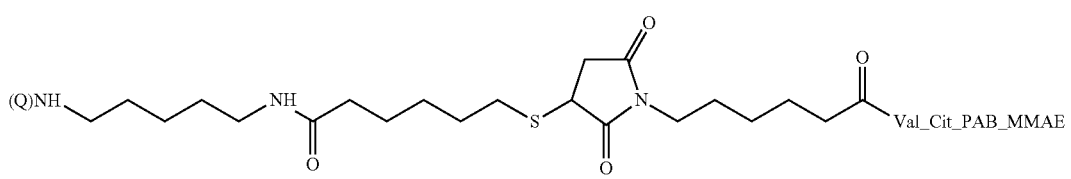

Compound IVb-3

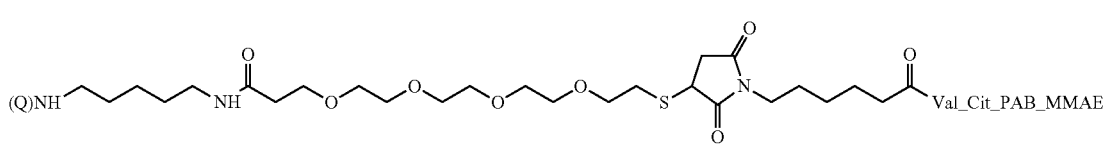

-continued
Compound IVb-4
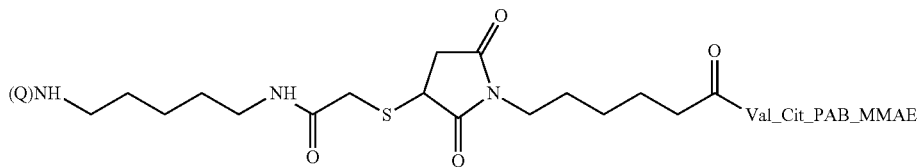
Compound IVb-5
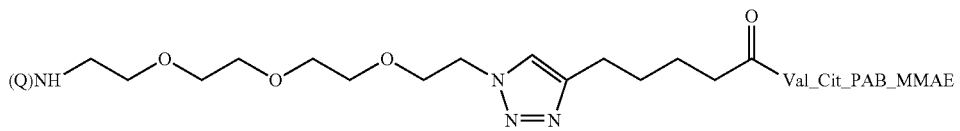
Compound IVb-6
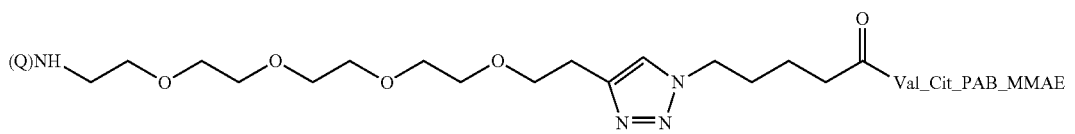
Compound IVb-7
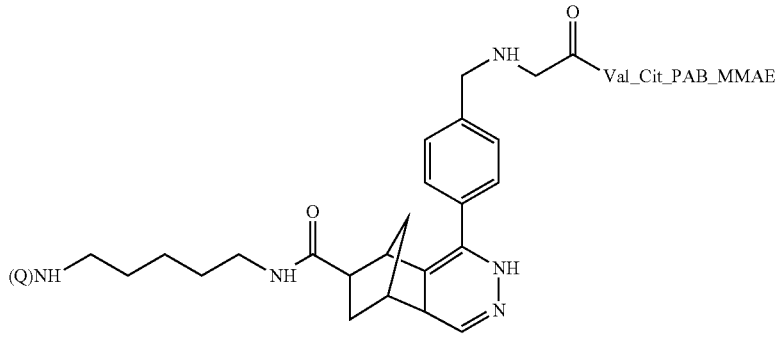
Compoound IVb-8
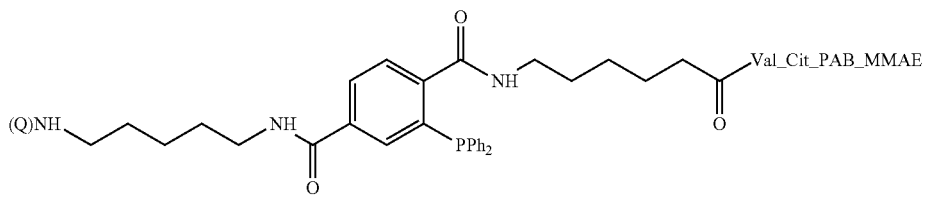
Compound IVb-9
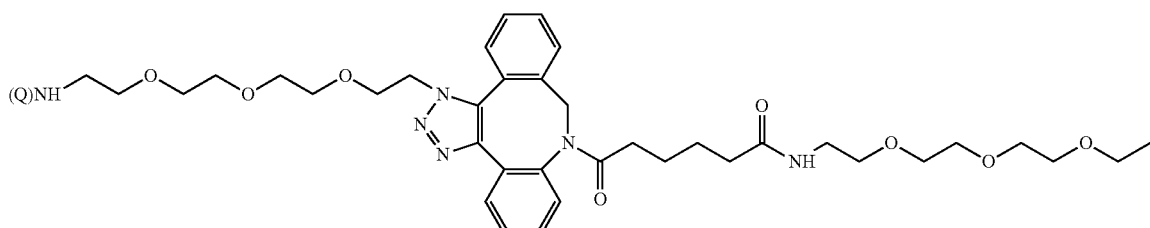
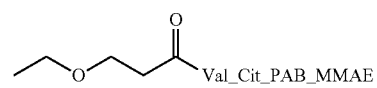
Compound IVb-10
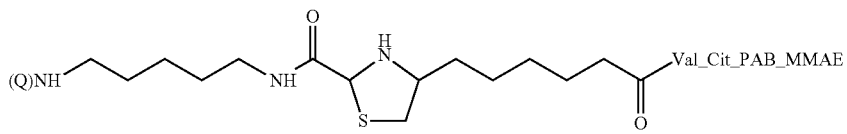
Compound IVb-11
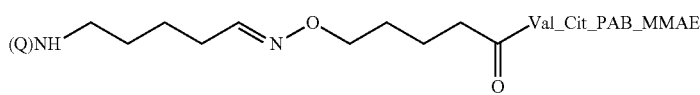

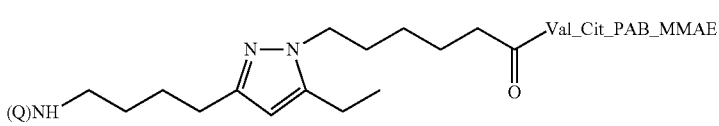

Compound IVb-12

In one embodiment, the glutamine (Q) is present in the CH2 of an antibody. In one embodiment, the glutamine (Q) is at position 295 (Kabat EU numbering). In one embodiment, an acceptor glutamine (Q) is at position 297 (e.g., a N297Q substitution). In one embodiment, the antibody comprises a substitution of an asparagine at position 297 with a non-asparagine, non-aspartic acid, non-glutamine, residue.

Exemplary lysine-based linker compounds can be prepared using known synthesis methods and starting reagents. In the examples below, all chemicals are purchased from Sigma-Aldrich, Fluka or Pierce Thermo scientific unless otherwise stated. All chemicals and solvents are used without further purification. Reactions are monitored by HPLC or by thin layer chromatography (TLC) using precoated silica gel 60 F aluminum sheets (Merck), and visualized by UV absorption or stained.

1. N-Succinimidyl-S-Acetylthioesters as Building Blocks

In a first step, mono-Boc-protected cadaverin is reacted with N-succinimidyl-S-acetylthioacetate (SATA) or succinimidyl acetyl(thiotetraethyleneglycol (SAT(PEG)4 or N-succinimidyl-S-acetylthiopropionate (SATP) to give the corresponding intermediates S-acetyl-cadaverin-Boc. Boc-deprotection is achieved in acidic conditions to give S-acetyl-cadaverin. Purification is achieved using reversed phase high performance liquid chromatography (RP-HPLC) to give the final product. The reaction scheme is shown in FIG. 3.

Figure 11:
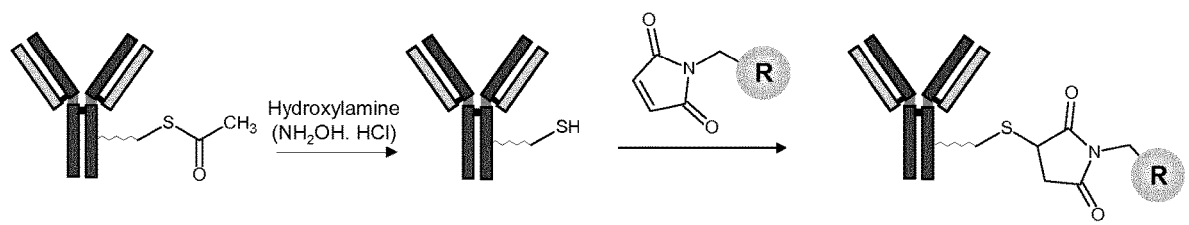
FIG. 11 shows a scheme for preparing an antibody conjugate from a S-acetyl-cadaverine linker of FIG. 3, where "R" in the figure is a moiety-of-interest Z.

The antibody conjugate is then prepared as shown in FIG. 11 ("R" is a moiety-of-interest Z). If glycosylated, enzymatic deglycosylation can be carried out using conditions such as: antibody (1 mg) in PBS buffer (0.1 mol/L NaCl and 0.05 mol/L sodium phosphate buffer, pH 7.4) are incubated with 100 units (0.2 μL) of N-glycosidase F (PNGase F) from *Flavobacterium meningosepticum* (New England BioLabs, Ipswich, UK) at 37° C. overnight to deglycosylate the antibody. The enzyme is then removed by centrifugation-dialysis (Vivaspin MWCO 50 kDa, Vivascience, Winkel, Switzerland). The product can be analyzed by LC/MS.

Antibody is reacted with S-acetyl-cadaverin in the presence of recombinant BTG (EC 2.3.2.13) from *streptomyces mobaraensis* (Zedira, Darmstadt, Germany) at a concentration of 1-20 U/mL in potassium-free phosphate buffered saline (PBS; pH 8) at 37° C. After 4 h to several days (depending on the antibody and the ligand), steady-state conditions are achieved. Excess ligand and enzyme are then removed using centrifugation-dialysis (Vivaspin MWCO 50 kDa, Vivascience, Winkel, Switzerland). Reactions are monitored by LC/MS.

De-protection (deacylation) of the S-acetyl-protected antibody to generate a free sulfhydryl is accomplished using hydroxylamine-HCl. Then, the antibody lysine-based linker conjugate is added to maleimide (or haloacetamide, e.g., bromoacetamide) containing compound at 4° C. for 1 h and the conjugation reaction is quenched by adding a 20-fold excess of cysteine. The reaction mixture is concentrated by centrifugal ultrafiltration and buffer-exchanged through Sephadex G-25 equilibrated with PBS at 4° C. The conjugate is then sterile filtered through a 0.2 μm filter.

2. Azide moieties

Mono-Boc-protected cadaverin is reacted with N-hydroxysuccinimide ester ethane azide (NHS-azide) or N-hydroxysuccinimide ester tetraoxapentadecane azide (NHS-PEG4-Azide) or N-hydroxysuccinimide ester dodecaoxanonatriacontane azide (NHS-PEG12-Azide) to give the intermediate azide-cadaverin-Boc. Boc-deprotection is achieved the presence of trifluoroacetic acid (TFA). Purification using RP-HPLC provides azide-cadaverin. The reaction scheme is shown in FIG. 5.

Figure 12:
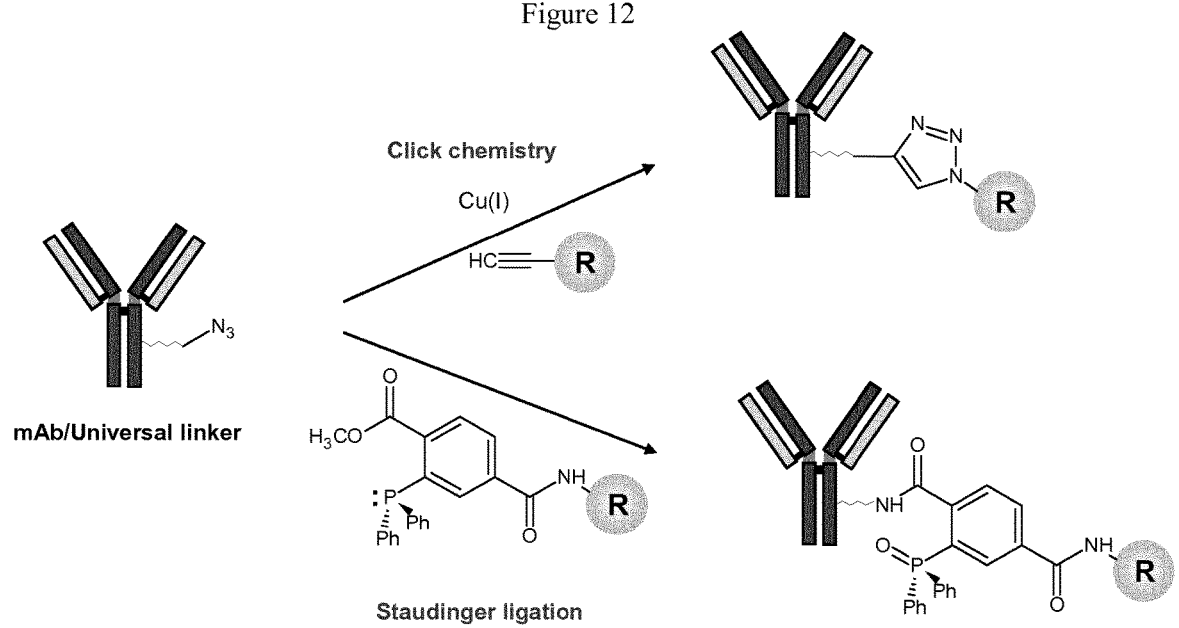
FIG. 12 shows a scheme for preparing an antibody conjugate from an azide-cadaverine linker of FIG. 5, where "R" in the figure is a moiety-of-interest Z.

The antibody conjugate is then prepared as shown in FIG. 12 ("R" is a moiety-of-interest Z). Antibody is deglycosylated and azide-cadaverin conjugates are prepared. The azide-modified antibody is reacted with the alkyne-reactive moiety compound using standard conditions for click chemistry.

3. Norbornene Moiety

In the first step, norbornene carboxylic acid is activated to a sulfo-NHS ester in the presence of 1-ethyl-3-(3-dimethylaminopropyl)carbodiimide (EDC). Then, mono-Boc-protected cadaverin is added and reacted with the reactive ester to give norbornyl-cadaverin-Boc. Deprotection of Boc is achieved by acidic treatment. Purification using RP-HPLC provides norbornyl-cadaverin. The reaction scheme is shown in FIG. 8.

Figure 13:
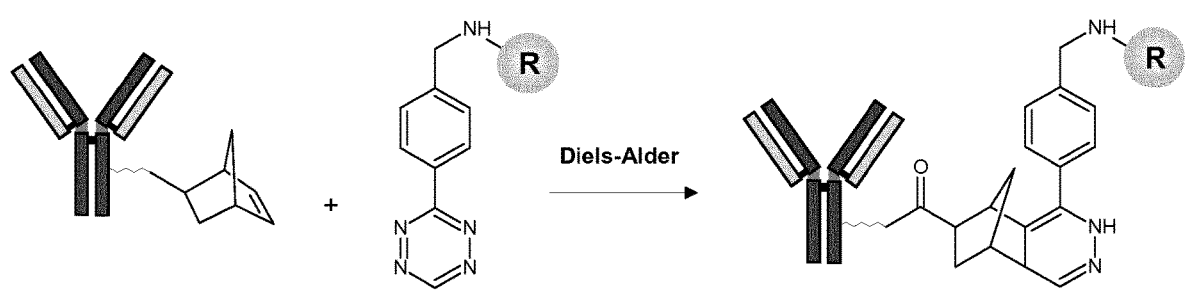
FIG. 13 shows a scheme for preparing an antibody conjugate from a norbornyl-cadaverine linker of FIG. 8, where "R" in the figure is a moiety-of-interest Z.

The antibody conjugate is then prepared as shown in FIG. 13 ("R" is a moiety-of-interest Z). Antibody is deglycosylated and azide-cadaverin conjugates are prepared. The norbornene-modified antibody (in PBS pH 7.4) is reacted with a molar excess of tetrazine reactive moiety compound (in DMSO or appropriate organic solvent) (molar excess is calculated based on initial norbornene reaction stoichiometry). The reaction is incubated at RT for 5 h and subsequently purified using centrifugal filtration to yield the completed antibody conjugate.

4. Alkyne Moiety

H-Lys-(Boc)-OMe is alkylated with propargyl glycine in the presence of Cs. Boc deprotection is achieved in a mixture of TFA (10%) and dichloromethane (DCM). Deprotection of the methyl ester with aqueous NaOH gives the glycan-lysine derivative in 50% yield. The reaction scheme is shown in FIG. 7.

Figure 14:
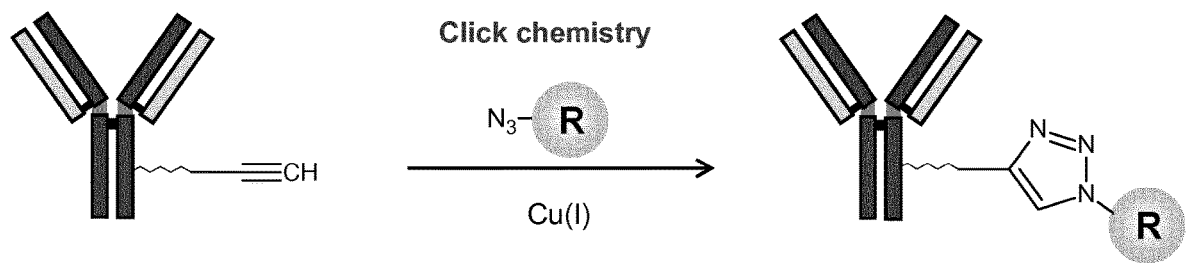
FIG. 14 shows a scheme for preparing an antibody conjugate from a glycan-lysine derivative linker of FIG. 7, where "R" in the figure is a moiety-of-interest Z.

The antibody conjugate is then prepared as shown in FIG. 14 ("R" is a moiety-of-interest Z). Antibody is deglycosylated and azide-cadaverin conjugates are prepared. The alkyne-modified antibody is reacted with the azide-reactive moiety compound using standard conditions for click chemistry. For conjugation by Staudinger ligation, the azido-derivated antibody is mixed with the phosphine-moiety compound and incubate at 37° C. for 2-4 hours, or at room temperature or 4° C. incubation during 16-24 hours. (final concentration of the antibody is preferably >2 mg/mL).

Further Processing of Antibodies

When the solid-support based methods are used for producing (e.g. manufacturing) an antibody conjugate, the antibody will generally be eluted from the solid support and subject to further processing steps (e.g. further reaction, purification, formulation with a pharmaceutically-acceptable excipient).

When the solid-support based methods are used in screening different antibodies or different components of a linker or different moieties of interest, a plurality of antibody-containing samples are thus provided thus and can then be conjugated to a moiety of interest and screened for a characteristic of interest. The phrase "a plurality of samples" refers to two or more samples. Because the methods provided herein are ideally suited for screening, the methods are performed simultaneously on at least 5, 10, tens or hundreds of samples. One of the strengths of the methods provided herein is that conjugation will be limited to acceptor glutamines in constant regions which can be readily defined, either because antibodies naturally contain a defined number of sites (e.g. one site per heavy chain in all antibodies of human isotype) or because antibodies are provided in a format where antibodies are engineered to contain the desired number of sites. In some preferred embodiments, a majority of the antibody-containing samples will comprise antibodies that immunospecifically bind to the same antigen.

Generally, it will be appreciated that once antibody conjugates have been obtained, they can be assessed for any characteristic of interest. In such assessment, antibodies may be eluted from the solid support or may remain bound to the solid support. In some embodiments, activity assays and/or other assays will be performed in order to characterize the antibody conjugates. In some embodiments, cell binding, affinity, and/or cytotoxicity assays will be performed. The characteristic that is assessed can be a property mediated by the variable region of the antibody, the constant region of the antibody and/or by the moiety-of-interest (Z).

In one example, the antibody conjugates can be assessed (e.g. compared) for their ability to inhibit the proliferation of, or, preferably, kill, target cells, e.g. using a cytotoxicity assay. Particularly, where moiety Z is a cytotoxic drug, the efficacy of the antibody as antibody-drug conjugates can be evaluated, e.g. as the ability of the antibodies to cause the death of tumor cells, infected cells, or generally any suitable target cells that express the antigen for which the antibody is specific.

In other example, moiety Z is a moiety that improves the pharmacokinetic properties of the antibody, and the pharmacokinetic properties of the antibody can be evaluated. In one embodiment, the pharmacokinetic property evaluated is stability of the antibody in a suitable environment, e.g. blood, pharmaceutical formulation, etc.

It will be appreciated that the antibodies conjugated to a moiety Z can be evaluated for any suitable pharmacokinetic property, irrespective of whether the moiety Z is a moiety that improves the pharmacokinetic properties of the antibody. For example, conjugation to an antibody of a large drug will affect the pharmacokinetic properties of the antibody. Thus, antibodies may be screened for any suitable pharmacokinetic property evaluated, e.g. aggregation of antibodies in formulation, stability of the antibody conjugate in an environment of interest, e.g. blood, pharmaceutical formulation, etc. In one embodiment, the method of evaluating antibodies is a method of evaluating and/or selecting antibodies conjugated to a moiety (Z) having a lower propensity to aggregate in solution, e.g. a pharmaceutical formulation.

Irrespective of the particular moiety Z, the antibody conjugates can be assessed (e.g. compared) for their ability to interact with and/or affect the activity of a target molecule (e.g. a predetermined antigen, a polypeptide). For example the antibody conjugates can be assessed for their ability to act as an agonist or antagonist of a target molecule. Exemplary target molecules include cell surface or soluble (poly) peptides. Binding, agonist or antagonist activity can be assessed by directly monitoring such binding or signaling activity, or can be assessed by any suitable indirect assay (e.g. effects on a cell or organism).

In general, well-known assays for detecting antibody binding to antigens, including competition-based assays, ELISAs, radioimmunoassays, Western blotting, BIACORE-based assays, and flow cytometry assays, can be equally applied to detect the interaction of antibodies, such as cytotoxic antibodies, with their target cells. Typically, target cells will be tumor or cancer cells.

Assessing the ability of the antibodies to inhibit the proliferation of, or, preferably, kill, target cells can be carried out using methods known in the art. For example, cell viability assays can be used to determine the cytotoxic effect of an ADC on a cell. See, for example, U.S. Pat. Nos. 7,659,241 and 7,498,298, each of which is incorporated herein in its entirety. In one embodiment, target cells (e.g. tumor or cancer cells, cells made to express a polypeptide specifically bound by an antibody) are introduced into plates, e.g., 96-well plates, and exposed to various amounts of the relevant antibodies. By adding a vital dye, i.e. one taken up by intact cells, such as AlamarBlue (BioSource International, Camarillo, Calif.), and washing to remove excess dye, the number of viable cells can be measured by virtue of the optical density (the more cells killed by the antibody, the lower the optical density). (See, e.g., Connolly et al. (2001) J Pharm Exp Ther 298:25-33, the disclosure of which is herein incorporated by reference in its entirety). Any other suitable in vitro cytotoxicity assay, assay to measure cell proliferation or survival, can equally be used, as can in vivo assays, e.g. administering the antibodies to animal models, e.g., mice, containing target cells expressing the relevant polypeptide bound by the antibody, and detecting the effect of the antibody administration on the survival or activity of the target cells over time. Also, where the antibody cross-reacts with a non-human polypeptide, e.g., a primate or murine ortholog, the antibodies can be tested on polypeptides or cells from such organism, for example to assess the ability of the antibody to bind to and/or kill target cells from the animal that expresses the relevant polypeptide, or to assess the ability of the antibody to cause side effects or other undesired biological effects in the animal that expresses the relevant polypeptide.

Any antibody can be selected that can detectably kill, slow, stop, or reverse the proliferation of target cells, in vitro or in vivo. Preferably, the antibody is capable of stopping the proliferation (e.g., preventing an increase in the number of cells in vitro or in vivo expressing the relevant polypeptide), and most preferably the antibody can reverse the proliferation, leading to a decrease in the total number of such cells. In certain embodiments, the antibody is capable of producing a 10%, 20%, 30%, 40%, 50%, 60%, 70%, 80%, 90%, 95%, 96%, 97%, 98%, 99%, or 100% decrease in the number of cells expressing the targeted polypeptide.

Preferably, in any the methods or compositions, a composition of a plurality of antibody conjugates is obtained wherein the antibodies have a uniform ratio of functionalized acceptor glutamines:antibody. In particular, the methods permit substantially complete conjugation of antibodies, for are range of moieties Z, including large, charged and/or hydrophobic drugs. In one aspect provided is a composition wherein a high portion of antibodies in the composition (e.g. at least 80%, 85%, 90%, 95% of the antibodies) comprise at least one moiety of interest, wherein the composition is substantially free of antibodies comprising a number of moieties of interest that is greater than 2 times, optionally 1.5 times, the mean number of conjugates per antibody (e.g., the mean DAR). In one embodiment provided is a composition comprising a plurality of antibodies of Formula II or IV, wherein at least 70%, 80%. 85%, 90%, 95%, 98% or 99% of the antibodies in the composition have the same number of functionalized acceptor glutamine residues (Q) (e.g., a functionalized acceptor glutamine of Formula II or IV) per antibody. Preferably at least 70%, 80%. 85%, 90%, 95%, 98% or 99% of the antibodies in said first antibody composition have no more or no less than (m) functionalized acceptor glutamine residues (Q) per antibody, wherein m is an integer, e.g. m=1, 2, 3 or 4. Optionally, at least 70%, 80%, 90%, 95%, 98% or 99% of the antibodies in the composition have the same q, r and z values. It can optionally be specified that the antibodies will share the same —NH—(C)$_n$—X, L, V, V', Y, Y', R, RR' and/or Z moieties.

Typically, a high portion of antibodies in an antibody sample (e.g. at least 80%, 85%, 90%, 95% of the antibodies) comprise at least one moiety of interest, wherein antibody sample compositions are preferably also free of antibodies having conjugated light chains. For example, an antibody sample may comprise tetrameric antibodies covalently linked to a moiety of interest (Z), wherein the composition is characterized by a mean DAR of close to 2 (e.g., between 1.4 and 2.0, or between 1.5 and 2.0, or between 1.7 and 2.0, between 1.8 and 2.0, or between 1.9 and 2.0), and wherein less than 10%, less than 5%, less than 2% or less than 1% of the antibodies in the composition comprise more than two moieties of interest (Z) per antibody. Preferably, less than 25%, 20%, 15% or preferably 10% of the antibodies in the composition comprise less than two moieties of interest (Z) per antibody. Optionally antibodies in an antibody sample are covalently linked to a moiety of interest (Z), wherein the composition is characterized by a mean DAR of close to 4 (e.g., between 3.0 and 4.0, or between 3.4 and 4.0, or between 3.6 and 4.0), wherein less than 10%, less than 5%, or less than 2% of the antibodies comprise more than four functionalized acceptor glutamines per antibody. Preferably, the composition is substantially free of antibodies having more than 4 moieties of interest (Z) per antibody.

The antibody-conjugates can be used for the manufacture of a pharmaceutical preparation and/or for the treatment or diagnosis of a mammal being in need thereof. In one embodiment, provided is the use of any of the methods or any compounds defined above for the manufacture of a pharmaceutical composition and/or for the treatment of a tumor or cancer in a mammal.

Also provided are methods of manufacturing the compounds defined above, for use as a medicament or an active component or active substance in a medicament. In a further aspect provided is a method for preparing a pharmaceutical composition containing a compound as defined above, to provide a solid or a liquid formulation for administration orally, topically, or by injection. Such a method or process at least comprises the step of mixing the compound with a pharmaceutically acceptable carrier.

Also provided are methods of manufacturing pharmaceutical compositions comprising the compounds as defined above. A compound may be administered in purified form together with a pharmaceutical carrier as a pharmaceutical composition. The preferred form depends on the intended mode of administration and therapeutic or diagnostic application. The pharmaceutical carrier can be any compatible, nontoxic substance suitable to deliver the compounds to the patient. Pharmaceutically acceptable carriers are well known in the art and include, for example, aqueous solutions such as (sterile) water or physiologically buffered saline or other solvents or vehicles such as glycols, glycerol, oils such as olive oil or injectable organic esters, alcohol, fats, waxes, and inert solids. A pharmaceutically acceptable carrier may further contain physiologically acceptable compounds that act for example to stabilize or to increase the absorption of the compounds. Such physiologically acceptable compounds include, for example, carbohydrates, such as glucose, sucrose or dextrans, antioxidants, such as ascorbic acid or glutathione, chelating agents, low molecular weight proteins or other stabilizers or excipients. One skilled in the art would know that the choice of a pharmaceutically acceptable carrier, including a physiologically acceptable compound, depends, for example, on the route of administration of the composition. Pharmaceutically acceptable adjuvants, buffering agents, dispersing agents, and the like, may also be incorporated into the pharmaceutical compositions.

EXAMPLES

Example 1

BTG-Mediated Coupling of Substrates to Protein G Bound Antibody

Deglycosylation of Antibody

Antibody in PBS buffer (1 mg/mL) was incubated with 100 Units/mg protein of N-glycosidase F (PNGase F) from *Elizabethkingia meningosepticum* (Sigma) overnight at 37° C. The enzyme was then removed by centrifugation-dialysis (Vivaspin MWCO 50 kDa, Sigma).

Surface Plasmon Resonance (SPR)

Biacore T100 General Procedure:

SPR experiments were performed on a Biacore T100 apparatus (Biacore GE Healthcare) at 25° C. In all Biacore experiments HBS-EP+ buffer (Biacore GE Healthcare) served as running buffer and sensorgrams were analyzed with Biaevaluation 4.1 and Biacore T100 Evaluation software.

Streptavidin-HRP was purchased from Beckman Coulter. Biotin-cadaverin and TGase (recombinant bacterial transglutaminase, gene derived from *streptomyces mobaraensis*, BTG) were purchased from Zedira, Darmstadt, Germany.

Immobilisation of Protein G on Sensor Chip CM5:

Immobilization of protein G on Sensor chip CM5: The chip surface was activated with EDC/NHS (N-ethyl-N'-(3-dimethylaminopropyl) carbodiimidehydrochloride and N-hydroxysuccinimide (Biacore GE Healthcare)). Protein G was diluted to 100 µg/ml in coupling buffer (10 mM acetate, pH 4.2) and injected until the appropriate immobilization level was reached (i.e. 2900 RU). Deactivation of the remaining activated groups was performed using 100 mM ethanolamine pH 8 (Biacore GE Healthcare).

Results

Figure 15:
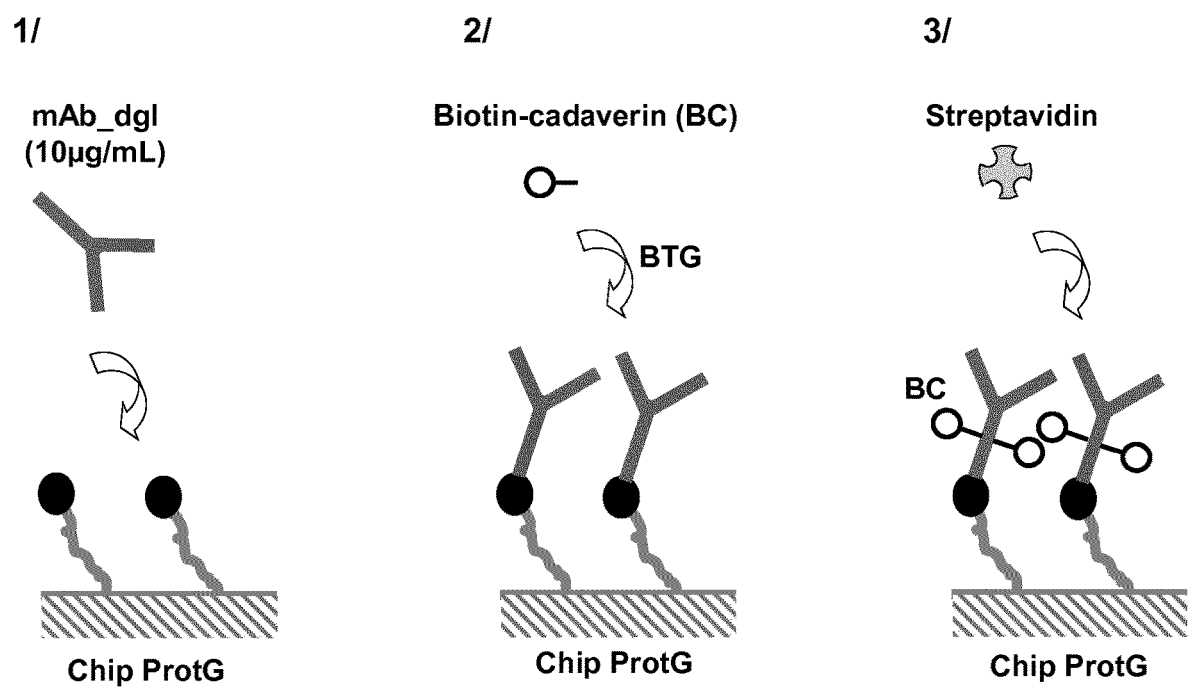
FIG. 15 shows the general strategy used in Example 1 for TGase-mediated coupling of antibodies to lysine-based linkers on solid supports.

An overview of the experimental process is shown in FIG. 15. Steps 1, 2 and 3 in FIG. 15 correspond to the steps 1, 2 and 3 below.

1. Capture of mAb_dgl on protein G:

Deglycosylated antibody (mAb_dgl) (diluted at a concentration of 10 µg/ml in the running buffer) was injected for 2 min at a constant flow rate of 10 µL/min on dextran layer containing immobilized protein G.

2. BTG coupling of biotin-cadaverin on immobilized mAb_dgl:

A solution of biotin-cadaverin (530 μM) and BTG (6U/mL) was injected for 6210s at a constant flow rate of 1 μL/min.

Figure 16:
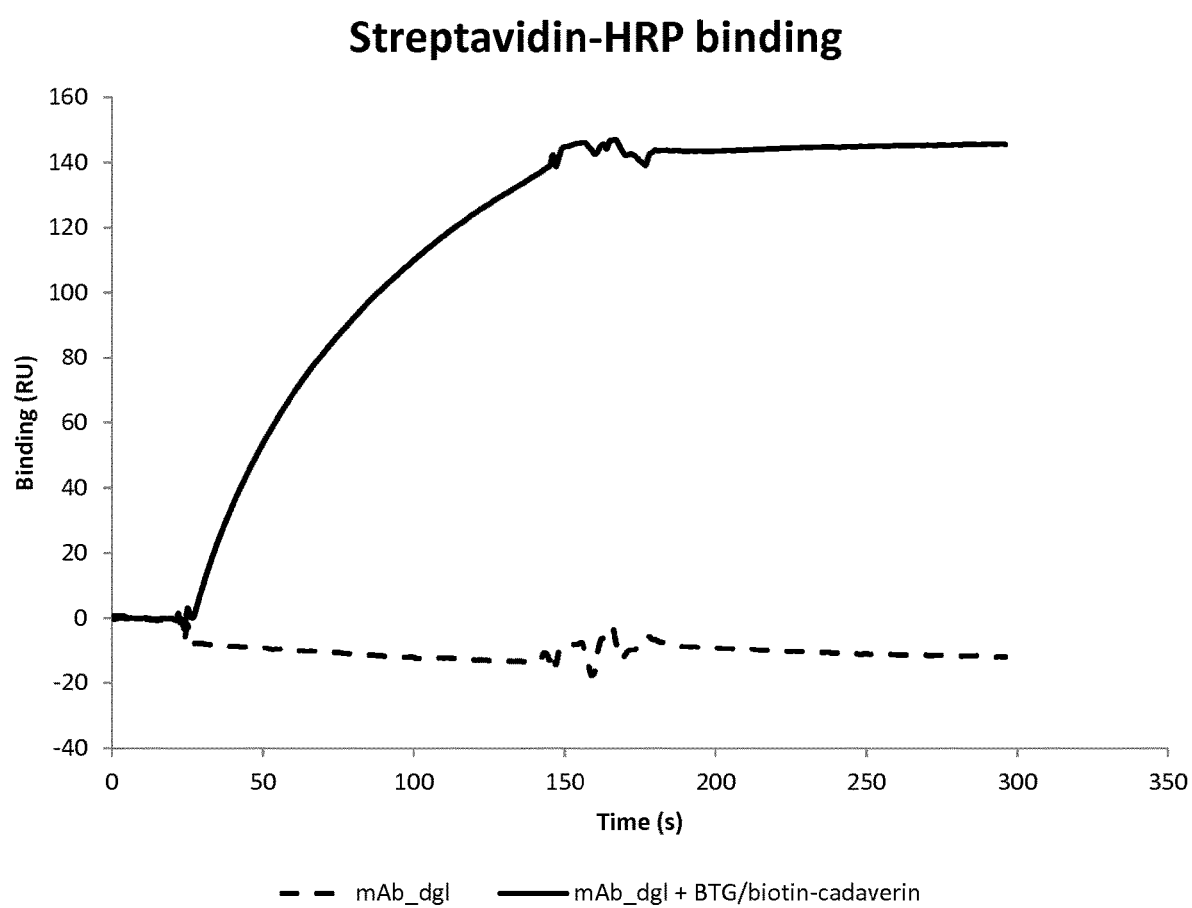
FIG. 16 shows the result of TGase-mediated coupling on solid supports as assessed by Biacore from Example 1.

3. Evaluation of the coupling:

Coupling of biotin-cadaverin was evaluated by injecting streptavidin-HRP on the surface. A binding level of 140 RU was detected after injection of SA-HRP on mAb_dgl treated with biotin-cadaverin/BTG, whereas no binding was detected before treatment. This confirms that biotin-cadaverin was successfully coupled to mAb_dgl captured on protein G. Results are shown in FIG. 16.

Example 2

BTG-Mediated Coupling of Substrates to Protein a Bound Antibody

Antibodies having either one acceptor glutamines within each of the two CH2 domains (having a N297S mutation to abolish glycosylation and an acceptor glutamine at position 295) or having two acceptor glutamines within each of the two CH2 domains (having a N297Q mutation to abolish glycosylation and provide for an acceptor glutamine at both positions 295 and 297) were immobilized on a solid support to test conjugation reactions with BTG.

Materials and Methods rProtA Sepharose was purchased from GEHealthcare. Azido-PEG-amine was purchased from Click Chemistry Tools (Scottsdale, Ariz., US), and bacterial TGase (recombinant bacterial transglutaminase, gene derived from *streptomyces mobaraensis*, BTG) was purchased from Zedira (Darmstadt, Germany).

Immobilization on prot A and BTG coupling reaction

Mutant antibody (N297S or N297Q, 1.25 mg) in PBS 1× was incubated with rProtA Sepharose FF (100 μL) during 4h30 at rt. Resulting mAb-rProtA resin were washed 3 times with PBS1×. The resin was re-suspended in PBS 1× buffer (pH 7.4, 230 μL).

Mutant antibody immobilized on rProtA resin (1.25 mg), substrate (Azido-PEG-amine, 75-150 μg) and bacterial transglutaminase (2 U/mL; Zedira, Darmstadt, Germany) were mixed together. The reaction was incubated on wheel at 37° C. overnight.

The resin was washed with PBS 1× (3×500 μL) and eluted with 50 mM NaOAc pH 3.5 (3×100 μL). The resulting mAb-linker was buffer-exchanged on ZEBA column pre-equilibrated with PBS1×.

Results

Figure 17:
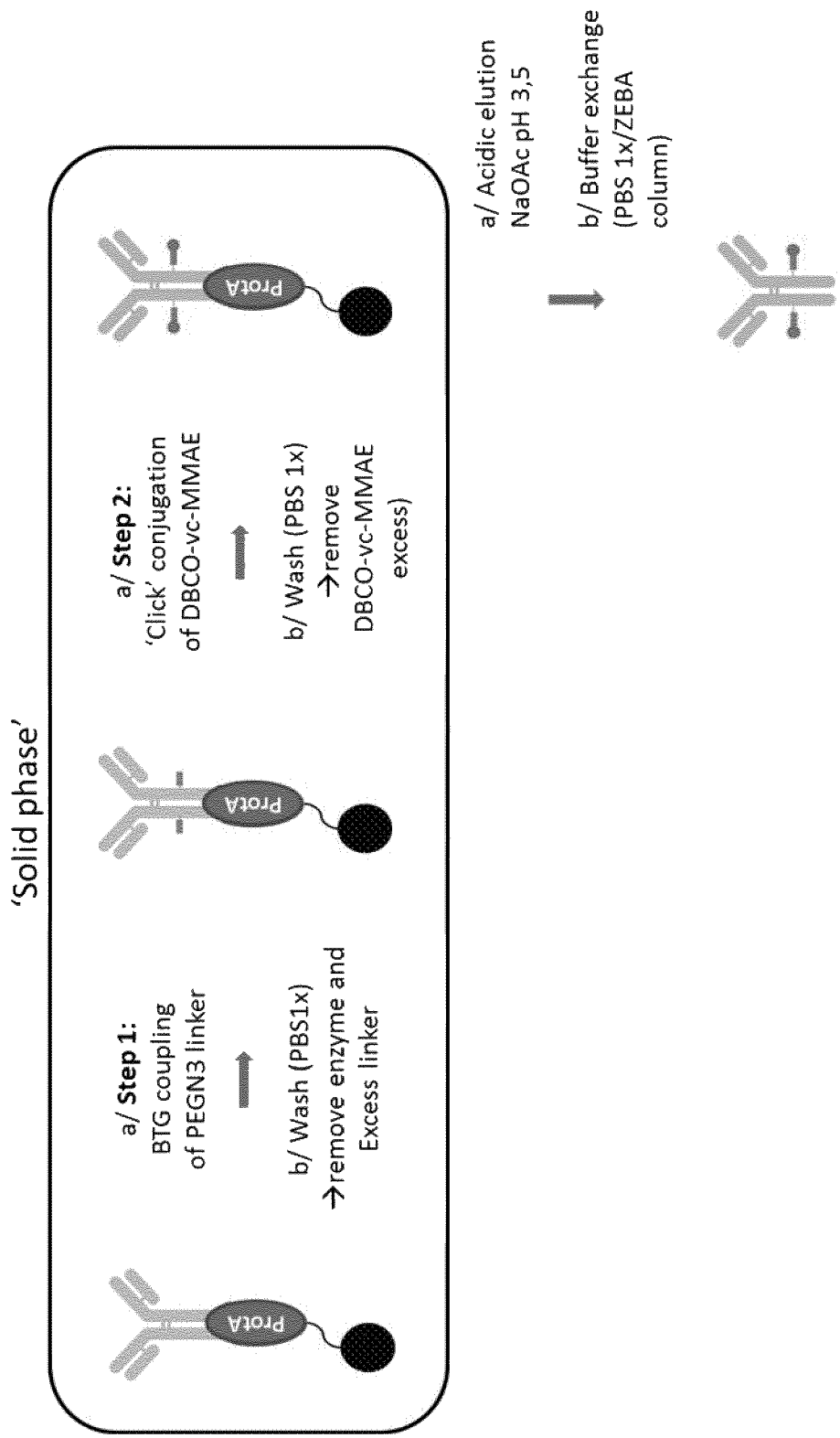
FIG. 17 shows an overview of a solid phase TGase coupling process.
Figure 18:
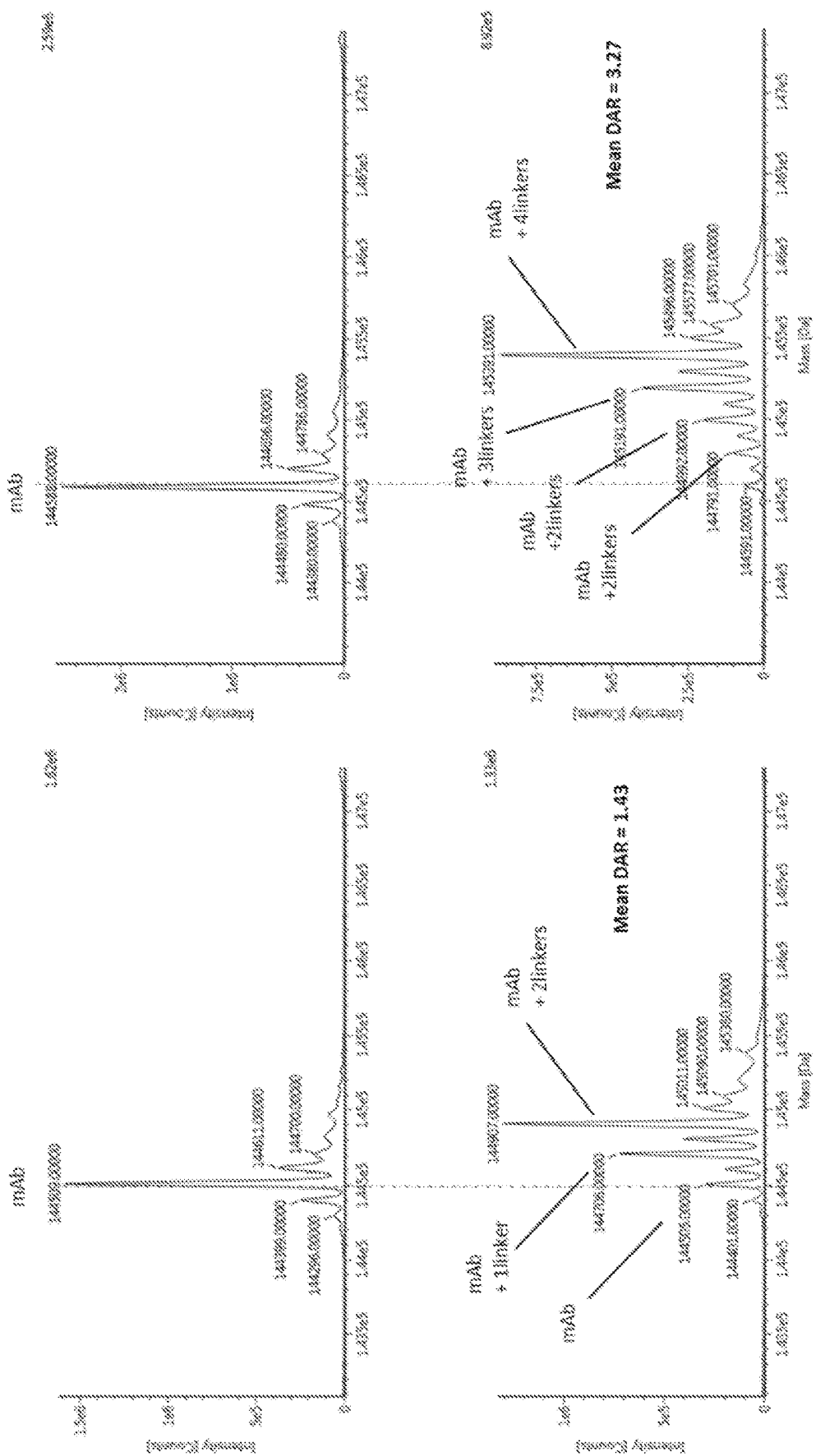
FIG. 18 shows results of TGase-mediated coupling on solid support as assessed by LC/MS.

An overview of the experimental process is shown in FIG. 17. Final compound are analyzed by LC/MS. Results are shown in FIG. 18. Successful coupling was observed, and in particular at DAR indicating that despite the antibody being bound by its Fc domain, the glutamines in both of heavy chains remained accessible to BTG for coupling, including for both the glutamines at position 295 and 297, as evidenced by a DAR above 1.0 for antibodies having two potential acceptor glutamines and above 2.0 for antibodies having four potential acceptor glutamines. A mean DAR of 1.43 was obtained following the BTG coupling step with the N297S antibody and 3.27 with the N297Q antibody, and it is expected that higher DARs can be obtained upon optimization of reaction conditions.

Example 3

BTG-Mediated Click Chemistry Reaction with Protein a Bound Antibody

Antibodies having one acceptor glutamines within each of the two CH2 domains (following enzymatic deglycosylation) were reacted in solution with a linker having a Click Chemistry reactive group, and upon completion of the conjugation reaction, the BTG- and coupled antibody-containing reaction mixture was immobilized on Protein A such that the antibody was bound by its Fc-region. The aim was to test whether Fc-immobilized conjugated antibody having a coupled glutamine at residue Q295 in the CH2 domain immobilized in such a way could be efficiently reacted using a complementary reactive group.

Materials and Methods rProtA Sepharose was purchased from GEHealthcare. Azido-PEG-amine was purchased from Click Chemistry Tools (Scottsdale, Ariz., US), and bacterial TGase (recombinant bacterial transglutaminase, gene derived from *streptomyces mobaraensis*, BTG) was purchased from Zedira (Darmstadt, Germany). DBCO-MMAE had the structure as follows:

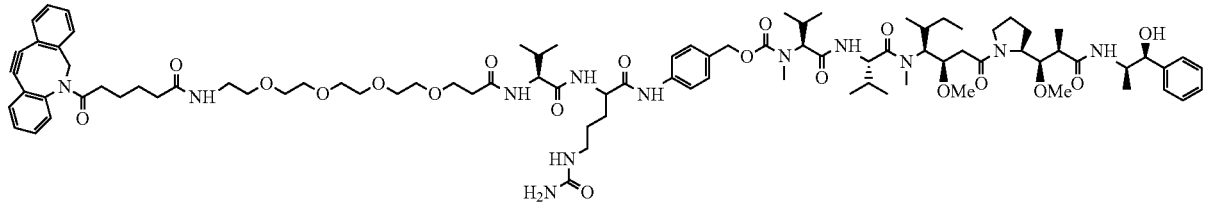 [SMILES: CCC(C)[C@@H]([C@@H](CC(=O)N1CCC[C@H]1[C@H](OC)[C@@H](C)C(=O)N[C@H](C)[C@@H](O)c1ccccc1)OC)N(C)C(=O)[C@@H](NC(=O)[C@H](C(C)C)N(C)C(=O)OCc1ccc(NC(=O)C(CCCNC(N)=O)NC(=O)[C@@H](NC(=O)CCOCCOCCOCCOCCNC(=O)CCCCC(=O)N2Cc3ccccc3C#Cc3ccccc32)C(C)C)cc1)C(C)C]

Deglycosylation of IgG1-mAb

Antibody of human IgG1 isotype in PBS buffer (1 mg, 6.3 mg/mL) was incubated with 10 Units/mg protein of N-glycosidase F (PNGase F) from *Elizabethkingia meningosepticum* (Sigma), 6 hours at +37° C.

BTG Coupling and Immobilization on rProtA

Deglycosylated mAb (1 mg, 2 mg/mL), substrate (Azido-PEG-amine, 120 μg) and bacterial transglutaminase (5 U/mL; Zedira, Darmstadt, Germany) were mixed in PBS buffer (pH 7.4). The reaction was heated at 37° C. overnight. Reactions are monitored by LC/MS.

The reaction mixture in PBS 1× was incubated with rProtA Sepharose FF (400 μL) for 2 h at room temperature. Resulting mAb-linker-rProtA resin were washed 3 times with PBS1×. The resin was re-suspended in PBS 1× buffer (pH 7.4, 400 μL).

'Click' Conjugation of DBCO-MMAE mAb-linker on rProtA resin (1 mg) was mixed together with DBCO-MMAE (46 μg). The reaction was incubated on wheel 2 h at rt.

The resin was washed with PBS 1× (10×400 μL) and eluted with 50 mM NaOAc pH 3.5 (2×200 μL). The resulting mAb-linker-MMAE was buffer-exchanged on ZEBA column pre-equilibrated with PBS1× yielding to final mAb-linker-MMAE (0.93 mg).

Results

Figure 19:
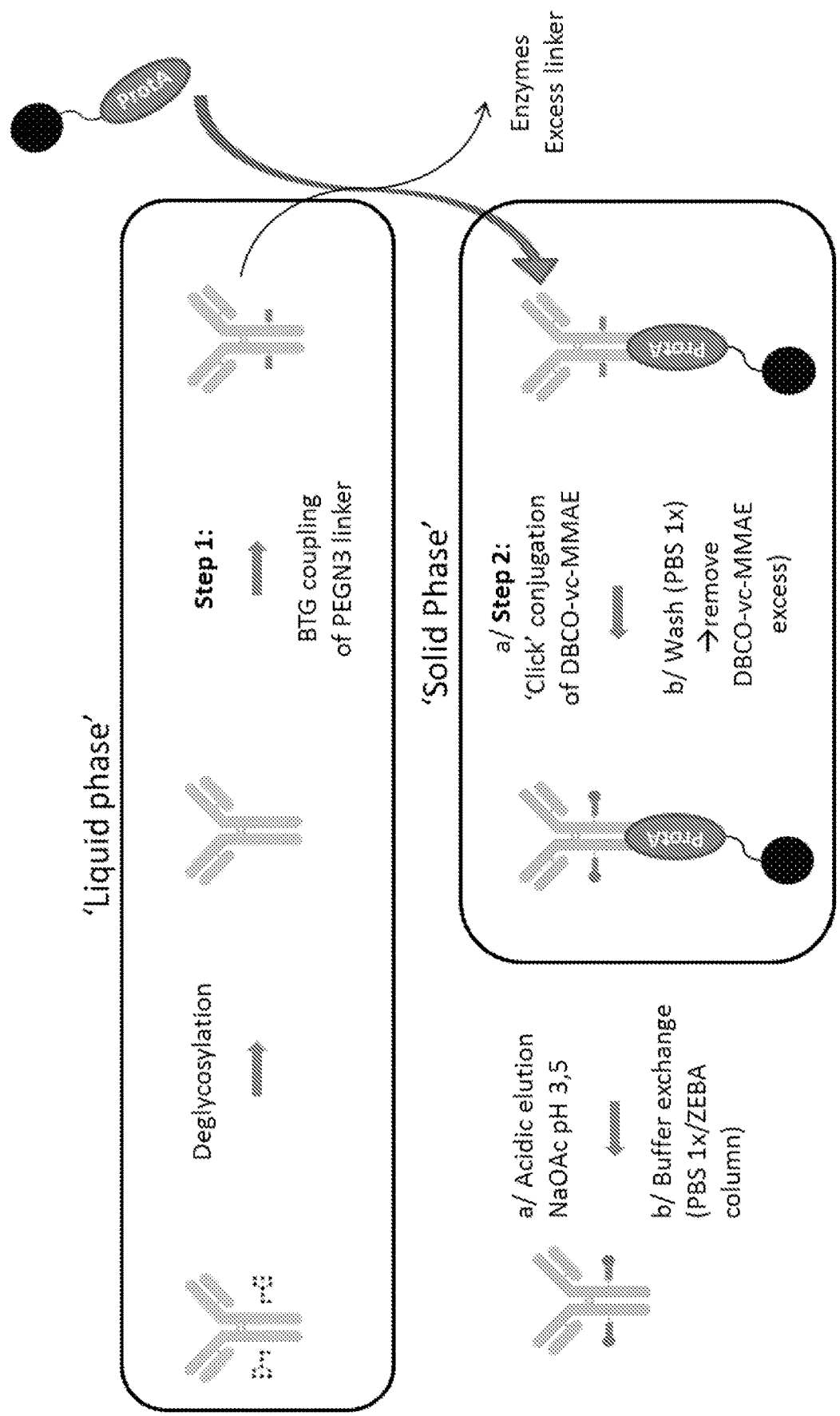
FIG. 19 shows an overview of a solid phase reaction process to generate antibody drug conjugates from antibodies having reactive linkers with click chemistry reactive groups conjugated thereteo. The TGase conjugation preceding the click chemistry reaction is carried out in liquid phase in this figure but can also be carried out on a solid support as shown in FIG. 17.
Figure 20:
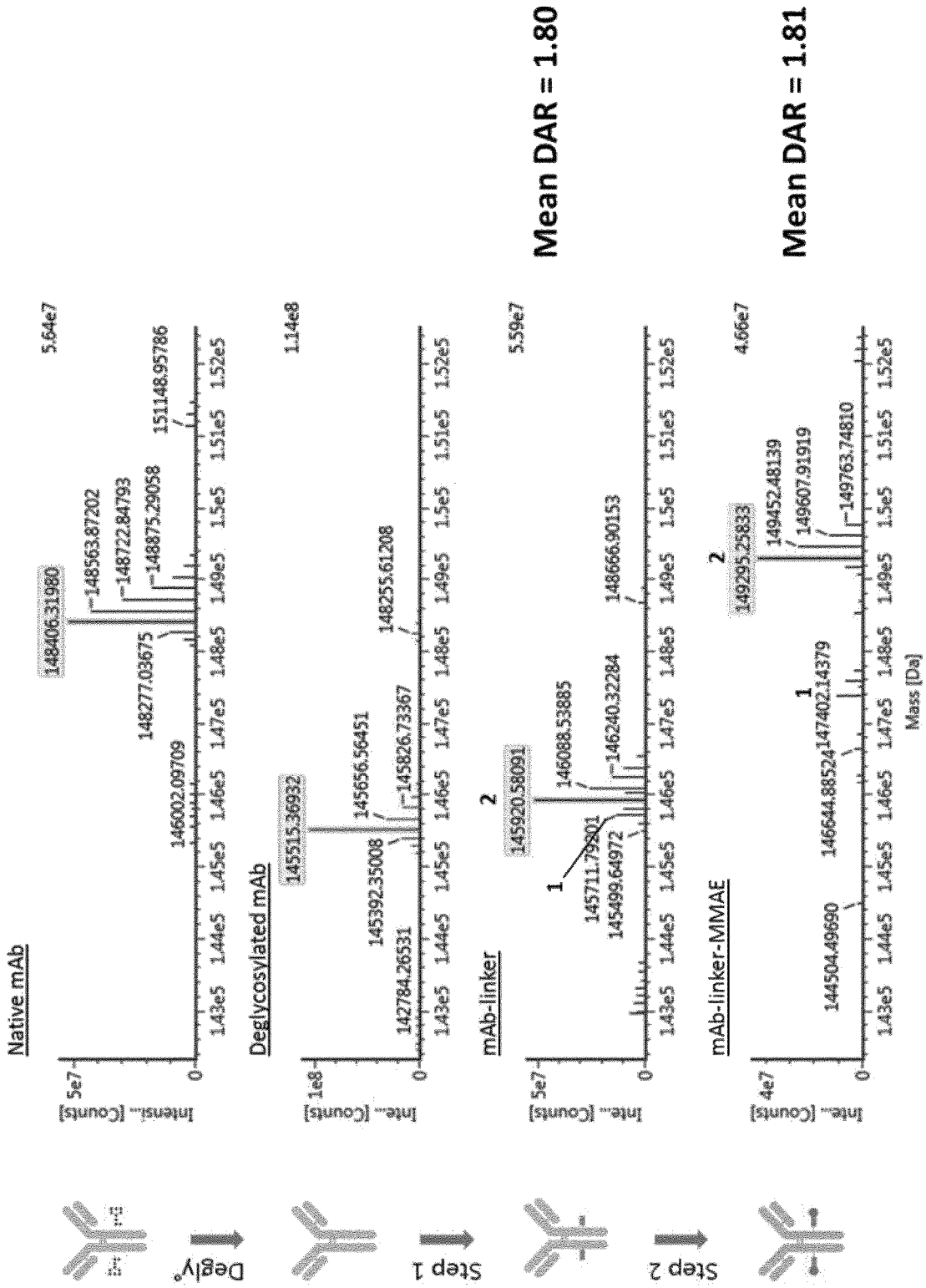
FIG. 20 shows results of TGase conjugation in liquid phase followed by click chemistry reaction on solid phase, as assessed by LC/MS.

An overview of the experimental process is shown in FIG. 19. Final compound was analyzed by LC/MS. Results are shown in FIG. 20. The antibody obtained was coupled at a high DAR. A mean DAR of 1.81 was obtained following the BTG coupling step, and a mean DAR of 1.80 was obtained following the Click Chemistry conjugation step. The reaction is of particularly high high efficiency when Click Chemistry reactive groups are used, despite the acceptor glutamines being within the CH2 domain of the antibody and the antibody being immobilized by its Fc domain.

All headings and sub-headings are used herein for convenience only and should not be construed as limiting the invention in any way. Any combination of the above-described elements in all possible variations thereof is encompassed by the invention unless otherwise indicated herein or otherwise clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. Unless otherwise stated, all exact values provided herein are representative of corresponding approximate values (e.g., all exact exemplary values provided with respect to a particular factor or measurement can be considered to also provide a corresponding approximate measurement, modified by "about," where appropriate).

All methods described herein can be performed in any suitable order unless otherwise indicated herein or otherwise clearly contradicted by context.

The use of any and all examples, or exemplary language (e.g., "such as") provided herein is intended merely to better illuminate the invention and does not pose a limitation on the scope of the invention unless otherwise indicated. No language in the specification should be construed as indicating any element is essential to the practice of the invention unless as much is explicitly stated.

The citation and incorporation of patent documents herein is done for convenience only and does not reflect any view of the validity, patentability and/or enforceability of such patent documents, The description herein of any aspect or embodiment of the invention using terms such as reference to an element or elements is intended to provide support for a similar aspect or embodiment of the invention that "consists of", "consists essentially of" or "substantially comprises" that particular element or elements, unless otherwise stated or clearly contradicted by context (e.g., a composition described herein as comprising a particular element should be understood as also describing a composition consisting of that element, unless otherwise stated or clearly contradicted by context).

This invention includes all modifications and equivalents of the subject matter recited in the aspects or claims presented herein to the maximum extent permitted by applicable law.

All publications and patent applications cited in this specification are herein incorporated by reference in their entireties as if each individual publication or patent application were specifically and individually indicated to be incorporated by reference.

Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or scope of the appended claims.

The invention claimed is:

1. A method for conjugating a moiety of interest (Z) to an antibody, comprising:
   (a) immobilizing an antibody comprising an acceptor glutamine at Kabat residue 295 and/or 297 on a solid support comprising a protein A or G affinity medium via the Fc region of the antibody to provide an immobilized antibody, wherein the acceptor glutamine is present within or appended to a constant region of the antibody;
   (b) reacting the immobilized antibody of process (a) with a linking reagent comprising a reactive group (R), in the presence of a transglutaminase (TGase), under conditions sufficient to obtain an antibody comprising the acceptor glutamine linked to a reactive group (R) via a linker;
   (c) a washing process to remove any unreacted materials; and
   (d) applying a compound comprising a moiety Z and a reactive group R' that is reactive with reactive group (R) to a solid support, to generate an antibody-moiety-of-interest (Z) conjugate.

2. The method of claim 1, further comprising recovering unreacted compound comprising a moiety Z and a reactive group R' and re-applying said recovered compound to the solid support to provide for higher completion of the reaction between antibody comprising reactive group (R) and compound comprising reactive group (R').

3. The method of claim 1, further comprising eluting immobilized antibody conjugates from the solid support to provide antibody conjugate compositions.

4. The method of claim 1, wherein the linking agent comprising a reactive group R is a compound having a structure of formula Ib:

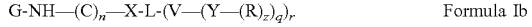

$$G-NH-(C)_n-X-L-(V-(Y-(R)_z)_q)_r \qquad \text{Formula Ib}$$

or a pharmaceutically acceptable salt or solvate thereof wherein:

G is an H, amine protecting group, or an antibody attached via an amide bond;

$(C)_n$ is a substituted or unsubstituted alkyl or heteroalkyl chain, optionally where the carbon adjacent to the nitrogen is unsubstituted, optionally wherein any carbon of the chain is substituted alkoxy, hydroxyl, alkylcarbonyloxy, alkyl-S—, thiol, alkyl-C(O)S—, amine, alkylamine, amide, or alkylamide;

n is an integer selected from among the range of 2 to 20, preferably 3 to 6;

X is NH, O, S, or absent;

L is a bond or a carbon comprising framework of 1 to 200 atoms substituted at one or more atoms, optionally wherein the carbon comprising framework is selected from the group consisting of a linear hydrocarbon, a symmetrically branched hydrocarbon, an asymmetrically branched hydrocarbon, a monosaccharide, a disaccharide, a linear oligosaccharide, a symmetrically branched oligosaccharide, an asymmetrically branched oligosaccharide, an amino acid, a dipeptide, a tripeptide, a tetrapeptide, an oligopeptide, a natural linear oligomer, a symmetrically branched oligomer, an asymmetrically branched oligomer, a dimer, a trimer, a linear higher oligomer, an asymmetrically branched higher oligomer, and a symmetrically branched higher oligomer, wherein the carbon comprising framework results from any chain-growth or step-growth polymerization process;

r is an integer selected from among 1, 2, 3 or 4;

q is an integer selected from among 1, 2, 3 or 4; and z is an integer selected from among 1, 2, 3 or 4;

V is independently absent, a bond or a continuation of a bond if L is a bond, a non-cleavable moiety or a conditionally-cleavable moiety, optionally following prior conditional transformation, which can be cleaved or transformed by a chemical, photochemical, physical, biological, or enzymatic process;

Y is independently absent, a bond or a continuation of a bond if V is a bond or continuation of a bond, or a spacer system which is comprised of 1 or more spacers; and R is a reactive moiety.

5. The method of claim 1, wherein the antibody-moiety-of-interest (Z) conjugate obtained is an antibody or antibody fragment comprising a functionalized acceptor glutamine residue having a structure of formula IVb:

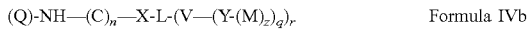  Formula IVb or a pharmaceutically acceptable salt or solvate thereof; wherein:

Q is glutamine residue present in an antibody;

$(C)_n$ is a substituted or unsubstituted alkyl or heteroalkyl chain, wherein any carbon of the chain is optionally substituted with an alkoxy, hydroxyl, alkylcarbonyloxy, alkyl-S—, thiol, alkyl-C(O)S—, amine, alkylamine, amide, or alkylamide;

n is an integer selected from among the range of 2 to 20;

X is NH, O, S, or absent;

L is a bond or a carbon comprising framework, preferably of 1 to 200 atoms substituted at one or more atoms, optionally wherein the carbon comprising framework is selected from the group consisting of a linear hydrocarbon, a symmetrically branched hydrocarbon, an asymmetrically branched hydrocarbon, a monosaccharide, a disaccharide, a linear oligosaccharide, a symmetrically branched oligosaccharide, an asymmetrically branched oligosaccharide, a natural linear oligomer, a symmetrically branched oligomer, an asymmetrically branched oligomer, a dimer, a trimer, a linear higher oligomer, an asymmetrically branched higher oligomer, and a symmetrically branched higher oligomer, wherein the carbon comprising framework results from any chain-growth or step-growth polymerization process;

r is an integer selected among 1, 2, 3 or 4;

q is an integer selected among 1, 2, 3 or 4;

z is an integer selected among 1, 2, 3 or 4; and

V is independently absent, a non-cleavable moiety or a conditionally-cleavable moiety;

Y is independently absent or a spacer system which is comprised of 1 or more spacers; and M is $(RR')\text{-}L'\text{-}(V'\text{—}(Y'\text{—}(Z)_{z'})_{q'})_{r'}$, wherein each of L', V', Y', z', q', and r' are defined as L, V, Y, z, q and r, and wherein (RR') is an addition product between an R and a complementary reactive group R';

Z is a moiety-of-interest, optionally a moiety that improves the pharmacokinetic properties, or a therapeutic moiety or a diagnostic moiety.

6. The method of claim 1, further comprising applying an antibody-containing sample to the solid support.

* * * * *